United States Patent
Wang et al.

(10) Patent No.: US 12,037,358 B2
(45) Date of Patent: *Jul. 16, 2024

(54) COMPOSITIONS COMPRISING REVERSIBLY MODIFIED OLIGONUCLEOTIDES AND USES THEREOF

(71) Applicant: Dicerna Pharmaceuticals, Inc., Lexington, MA (US)

(72) Inventors: Weimin Wang, Newton, MA (US); Venkata Krishnamurthy, Ashland, MA (US)

(73) Assignee: DICERNA PHARMACEUTICALS, INC., Lexington, MA (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/836,209

(22) Filed: Jun. 9, 2022

(65) Prior Publication Data

US 2023/0101227 A1  Mar. 30, 2023

Related U.S. Application Data

(63) Continuation of application No. 16/325,979, filed as application No. PCT/US2017/048239 on Aug. 23, 2017, now Pat. No. 11,390,642.

(60) Provisional application No. 62/378,635, filed on Aug. 23, 2016.

(51) Int. Cl.
| | |
|---|---|
| *C07H 19/06* | (2006.01) |
| *A61K 9/107* | (2006.01) |
| *A61K 31/712* | (2006.01) |
| *C07H 21/00* | (2006.01) |
| *C12N 15/11* | (2006.01) |
| *C12N 15/113* | (2010.01) |

(52) U.S. Cl.
CPC ............. *C07H 19/06* (2013.01); *A61K 9/107* (2013.01); *A61K 31/712* (2013.01); *C07H 21/00* (2013.01); *C12N 15/11* (2013.01); *C12N 15/113* (2013.01); *C12N 2310/11* (2013.01); *C12N 2310/113* (2013.01); *C12N 2310/12* (2013.01); *C12N 2310/14* (2013.01); *C12N 2310/141* (2013.01); *C12N 2310/20* (2017.05); *C12N 2310/314* (2013.01)

(58) Field of Classification Search
None
See application file for complete search history.

(56) References Cited

U.S. PATENT DOCUMENTS

| | | |
|---|---|---|
| 6,265,558 B1 | 7/2001 | Cook et al. |
| 7,282,590 B2 | 10/2007 | Ojima |
| 7,847,119 B2 | 12/2010 | Ojima |
| 8,927,513 B2 | 1/2015 | Manoharan et al. |
| 9,376,700 B2 | 6/2016 | Petersson |
| 9,744,183 B2 | 8/2017 | Verdine et al. |
| 9,884,886 B2 | 2/2018 | Butora |
| 10,307,434 B2 | 6/2019 | Verdine et al. |
| 2005/0232928 A1 | 10/2005 | Ojima |
| 2011/0008395 A1 | 1/2011 | Torchilin et al. |
| 2012/0316224 A1 | 12/2012 | Verdine et al. |
| 2015/0315226 A1 | 11/2015 | Butora |

FOREIGN PATENT DOCUMENTS

| | | |
|---|---|---|
| CA | 2767253 A1 | 1/2011 |
| JP | 2010532786 A | 10/2010 |
| WO | 91/14696 A1 | 10/1991 |
| WO | 2010/039543 A2 | 4/2010 |
| WO | 2014/088920 A1 | 6/2014 |
| WO | 2014/088923 A1 | 6/2014 |
| WO | 2015/032968 A1 | 3/2015 |
| WO | 2015/069932 A1 | 5/2015 |
| WO | 2015/188197 A2 | 12/2015 |

OTHER PUBLICATIONS

Sigurdsson, Snorri Th, and Fritz Eckstein. "Site specific labelling of sugar residues in oligoribonucleotides: reactions of aliphatic isocyanates with 2' amino groups." Nucleic acids research 24.16 (1996): 3129-3133.*
International Search Report and Written Opinion dated Jan. 9, 2018 from International Application No. PCT/US2017/048239 (Authorized Officer, Lee W. Young), 14 Pages.
Ochi et al., "Gene silencing by 2'-O-methyldithiomethyl-modified siRNA, a prodrug-type siRNA responsive to reducing environment", Bioorganic & Medicinal Chemistry Letters, Feb. 1, 2016, vol. 26, pp. 845-848.
Kock et al., "Disulfide reshuffling triggers the release of a thiol-free anti-HIV agent to make up fast-acting, potent macromolecular prodrugs", Chem. Commun., Dec. 24, 2014, vol. 50, No. 93, pp. 14498-14500.
Bazzanini et al., "Synthetic Approaches to a Mononucleotide Prodrug of Cytarabine", Nucleosides, Nucleotides, and Nucleic Acids, 2005, vol. 24, No. 10-12, pp. 1635-1649.
Ruiz-Sanchis et al., "Highly Active Macromolecular Prodrugs Inhibit Expression of the Hepatitis C Virus Genome in the Host Cells", Advanced Healthcare Materials, 2015, vol. 4, pp. 65-68.

(Continued)

*Primary Examiner* — Patrick T Lewis
(74) *Attorney, Agent, or Firm* — MH2 TECHNOLOGY LAW GROUP, LLP

(57) ABSTRACT

Disclosed herein are glutathione-sensitive oligonucleotides and methods of using the same. Any oligonucleotide of interest may be modified with a glutathione-sensitive moiety, including oligonucleotides used for in vivo delivery, such as nucleic acid inhibitor molecules. Typically, the glutathione-sensitive moiety is used to reversibly modify the 2'-carbon of a sugar moiety in one or more nucleotides in the oligonucleotide, although other carbon positions may also be modified with the glutathione-sensitive moiety. Also disclosed are glutathione-sensitive nucleotide and nucleoside monomers, including glutathione-sensitive nucleoside phosphoramidites that can be used, for example, in standard oligonucleotide synthesis methods. In addition, glutathione-sensitive nucleotide and nucleoside monomers without a phosphoramidite can be used therapeutically, for example, as anti-viral agents.

18 Claims, 7 Drawing Sheets

(56) References Cited

OTHER PUBLICATIONS

Lambert et al., "Ado-trastuzumab Emtansine (T-DM1): An Antibody-Drug Conjugate (ADC) for HER2-Positive Breast Cancer", J. Med. Chem., 2014, vol. 57, pp. 6949-6964.

Alouane et al., "Self-Immolative Spacers: Kinetic Aspects, Structure-Property Relationships, and Applications", Angew. Chem. Int. Ed., 2015, vol. 54, pp. 7492-7509.

Pira et al., "Synthesis of Peptide Thioacids at Neutral pH Using Bis(2-sulfanylethyl)amido Peptide Precursors", Organic Letters, 2013, vol. 15, No. 20, pp. 5346-5349.

Coughlin et al., "Metabolism, Pharmacokinetics, Tissue Distribution, and Stability Studies of the Prodrug Analog of an Anti-Hepatitis B Virus Dinucleoside Phosphorothioate", Drug Metabolism and Disposition, 2012, vol. 40, No. 5, pp. 970-981.

Butora et al., "Cyclic-Disulfide-Based Prodrugs for Cytosol-Specific Drug Delivery", Angew. Chem. Int. Ed., 2014, vol. 53, pp. 14046-14050.

Biscans et al., "A versatile post-synthetic method on a solid support for the synthesis of RNA containing reduction-responsive modifications", Org. Biomol. Chem., 2016, vol. 14, pp. 7010-7017.

Meade et al.,"Efficient delivery of RNAi prodrugs containing reversible charge-neutralizing phosphotriester backbone modifications", Nature Biotechnology, Dec. 2014, vol. 32, No. 12, 8 pages.

Meade et al.,"Efficient delivery of RNAi prodrugs containing reversible charge-neutralizing phosphotriester backbone modifications", Nature Biotechnology, Dec. 2014, vol. 32, No. 12, siRNN Supplementary Figures, 36 pages.

Christian Ducho, "Enzymatically Cleavable siRNA Prodrugs: a New Paradigm for the Intracellular Delivery of RNA-Based Therapeutics", ChemMedChem, 2015, vol. 10, pp. 1625-1627.

Lima et al., "Binding and Cleavage Specificities of Human Argonaute2", The Journal of Biological Chemistry, Sep. 18, 2009, vol. 284, No. 38, pp. 26017-26028.

Johnsson et al., "New light labile linker for solid phase synthesis of 2'-O-acetalester oligonucleotides and applications to siRNA prodrug development", Bioorganic & Medicinal Chemistry Letters, 2011, vol. 21, pp. 3721-3725.

Lavergne et al., "Synthesis and Preliminary Evaluation of pro-RNA 2'-O-Masked with Biolabile Pivaloyloxymethyl Groups in an RNA Interference Assay", J. Org. Chem., 2011, vol. 76, pp. 5719-5731.

Martin et al., "Assessment of new 2'-O-acetalester protecting groups for regular RNA synthesis and original 2'-modified proRNA", Bioorganic & Medicinal Chemistry Letters, 2009, vol. 19, pp. 4046-4049.

Peyrottes et al.,"A step further in the SATE mononucleotide prodrug approach", Nucleic Acids Symposium Series, Sep. 8, 2008, No. 52, pp. 539-540.

Pradere et al., "Synthesis of Nucleoside Phosphate and Phosphonate Prodrugs", Chem. Rev., 2014, vol. 114, pp. 9154-9218.

Ochi et al., "A post-synthetic approach for the synthesis of 2'-O-methyldithiomethyl-modified oligonucleotides responsive to a reducing environment", Chem. Commun., 2013, vol. 49, pp. 7620-7622.

Ochi et al., "A New Nucleic Acid Prodrug Responsive to High Thiol Concentration: Synthesis of 2'-O-thyldithiomethyl-Modified Oligonucleotides by Post-Synthetic Modification", Current Protocols in Nucleic Acid Chemistry, Sep. 2015, Supplement 62, pp. 4.63.1-4.63.20.

Zheng et al., "Single modification at position 14 of siRNA strand abolishes its gene-silencing activity by decreasing both RISC loading and target degradation", The FASEB Journal, Oct. 2013, vol. 27, pp. 1-10.

Extended European Search Report dated Aug. 25, 2020 from corresponding European Application No. 17844358.6, 15 Pages.

Sawyer et al., "Distances between DNA and ATP Binding Sites in the TyrR-DNA Complex", Biochemistry, 2000, vol. 39, No. 19, pp. 5653-5661.

Office Action dated Jul. 20, 2021 for corresponding Japanese Patent Application No. 2019-508973, 12 pages with English translation.

Nakagawa et al., "Development of an efficient synthesis method of 2'-O-methyldithiomethyl modified RNA using a post-synthetic approach", Proceedings of Symposium on Progress of Reaction and Synthesis, 2013, vol. 39, p. 102, with English translation.

Ochi et al., "Synthesis of Prodrug-Type Nucleic Acids Responsive to Reducing Environment and Evaluation of Their Duplex Stabilities", Proceedings of Symposium on Antisense, 2014, vol. 24, p. 72.

* cited by examiner

*In Vivo* Potency and Duration Studies of Test Compound 1

*In Vivo* Potency and Duration Studies of Test Compound 2

COMPOSITIONS COMPRISING REVERSIBLY MODIFIED OLIGONUCLEOTIDES AND USES THEREOF

CROSS REFERENCE TO RELATED APPLICATIONS

This application is a continuation of U.S. patent application Ser. No. 16/325,979 filed 15 Feb. 2019, which is a U.S. National Stage application of PCT/US2017/048239 filed 23 Aug. 2017, which claims the benefit of, and relies on the filing date of, U.S. provisional patent application No. 62/378,635, filed 23 Aug. 2016, the entire disclosure of which is incorporated herein by reference.

BACKGROUND

Oligonucleotides have various uses in molecular biology, including, for example, use as probes, primers, or linkers. Oligonucleotides can also be used therapeutically, for example, to edit genomic DNA sequences (e.g., Clustered Regularly Interspaced Short Palindromic Repeats "CRISPR"), to restore defective or missing genes using gene therapy techniques, or as nucleic acid inhibitor molecules to modulate intracellular RNA levels through a diverse set of mechanisms. Small interfering RNA ("siRNA"), antisense oligonucleotides, ribozymes, microRNA, antagomirs, and aptamers are all examples of nucleic acid molecules that have demonstrated early promise in the treatment of cancers, viral infections, and genetic disorders. Nucleoside and nucleotide analogs are also commonly used therapeutically, particularly as antiviral or anticancer agents.

Like other drugs, therapeutic oligonucleotides need, among other things, stability in biological systems and sufficient potency at the intended site of action. The in vivo environment presents challenges to the stability of therapeutic oligonucleotides because of the conditions that these molecules experience as they navigate their way through the body and into the cytosol of a target cell. For example, oligonucleotides are susceptible to degradation by nucleases in the serum, including 3'-exonucleases. See Behlke, M. A., *Oligonucleotides*, 2008, 18:305-320. Nucleic acid inhibitor molecules having a single-stranded 3'-overhang, such as certain canonical 21-mer siRNA and other siRNA designs known in the art and described herein may, consequently, be particularly susceptible to degradation by such 3'-exonucleases. Behlke, M. A., *Oligonucleotides*, 2008, 18:305-320. In addition, an RNase A-like activity has been implicated in the degradation of siRNAs in serum.

Furthermore, even if an oligonucleotide makes it through the environment of the serum and enters a target cell of interest, it may still be exposed to enzymes or conditions (e.g., pH) that impair the stability of the oligonucleotide. For example, pH-dependent ribonucleases and deoxyribonucleases are present in the vesicles of cells, e.g., lysosomes, endosomes and fused endosomal/lysosomal vesicles.

Over the years, different approaches have been pursued in an attempt to protect therapeutic oligonucleotides from these environmental conditions. A major approach to addressing problems associated with in vivo administration of nucleic acid inhibitor molecules has been to introduce certain irreversible, covalent chemical modification to one or more nucleotides in the nucleic acid molecule. Many types of irreversible nucleotide chemical modification have been reported over the years. See e.g., Bramsen et al., *Nucleic Acids Res.*, 2009, 37:2867-2881. Such irreversible chemical modifications often involve changes to the sugar moiety of a nucleotide.

Commonly, the 2'-carbon (C2') of the sugar moiety of a nucleotide has been irreversibly modified because the 2'-hydroxyl (2'-OH) group makes the ribonucleotide more susceptible to certain ribonucleases. For example, many groups have modified the 2' position of the sugar moiety from a hydroxyl group to a 2'-fluoro (2'-F) or a 2'-O-methyl (2'-OMe), and such changes have effectively increased nuclease resistance of RNA oligonucleotides. See Behlke, M. A., *Oligonucleotides*, 2008, 18:305-320.

The 5'-end of the oligonucleotide is another position that has been commonly modified in an irreversible manner. Typical irreversible modifications at the 5'-end of the nucleic acid inhibitor molecule include a phosphoramidate or a chemical moiety that mimics the electrostatic and steric properties of a phosphate group ("phosphate mimic"). See Prakash et al., 2015, 43(6):2993-3011. Typically, these 5'-phosphate mimics contain phosphatase-resistant linkages.

It is also possible to irreversibly modify the backbone of an oligonucleotide. For example, the phosphorothioate (PS) backbone modification replaces a non-bridging oxygen atom with a sulfur atom and may extend the half-life of oligonucleotides in plasma from minutes to days. See Shen et al. *Nucleic Acids Res.*, 2015, 43:4569-4578; Eckstein, F. *Nucleic Acid Thera.*, 2014, 24(6):374-387.

Often it is desirable to irreversibly modify one or more nucleotide positions in the same nucleic acid inhibitor molecule with more than one type of irreversible modification. For example, it is common to modify a siRNA molecule with multiple 2'-F, 2'-OMe, and phosphorothioate modifications. See Podbevsek et al., *Nucleic Acid Res.*, 2010, 38(20):7298-7307.

While these irreversible modifications may help to improve the stability of a nucleic acid and/or protect it from enzymes in the serum or in a cell, depending on the position of the modified nucleotide and/or the number of modifications, these irreversible modifications can also reduce the potency or activity of the nucleic acid inhibitor molecule once it reaches the cytosol of the cell. See Behlke, M. A., *Oligonucleotides*, 2008, 18:305-320. Furthermore, because these modifications are irreversible under intracellular conditions, they are not removed from the nucleic acid inhibitor molecule before it exerts its biological activity in the cytosol of the cell. If the irreversible modifications result in reduced potency or activity, they can limit the therapeutic efficacy of nucleic acid inhibitor molecules containing them.

While research and drug development efforts have focused on irreversible modifications to protect nucleic acid inhibitor molecules, there have also been, on a smaller scale, reports of oligonucleotides containing a chemical modification that is reversible and can be removed after an oligonucleotide enters a cell. The reversible modifications can be removed, for example, by the action of an intracellular enzyme or by the chemical conditions inside a cell (e.g., through reduction by intracellular glutathione). Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., *Nature Biotechnology*, 2014, 32:1256-1263 ("Meade"), PCT Publication No. WO 2014/088920 to Merck Sharp & Dohme Corp. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. J. Am. Chem. Soc. 2003, 125:940-950).

There has been less effort in the art to reversibly modify other positions in the sugar moiety of nucleotides, such as the 2'-carbon (also referred to as C2'). C2' has been reversibly modified using modifications that are sensitive to enzymatic cleavage (Lavergne et al., *J. Org. Chem.,* 2011, 76:5719-5731) and light-stimulated cleavage (Johnsson et al., *Bioorganic & Med. Chem. Letters,* 2011, 21:3721-25). Very recently, a reversible disulfide modification was applied to RNA molecules at the 2' carbon. More particularly, a specific, 2'-O-methyldithiomethyl (2'-O MDTM) RNA was designed with a disulfide bridge cleavable intracellularly by glutathione and was shown in vitro to be able to inhibit the expression of an exogenously added luciferase gene in isolated A549 cells. See Ochi et al., *Bioorganic Medicinal Chemistry Letters,* 2016, 26:845-848. However, the authors in Ochi found that nucleoside phosphoramidites containing the 2'-O-MDTM group are incompatible with standard oligonucleotide solid phase synthesis. See Ochi 2016; see also, Ochi et al., *Curr. Protoc. Nucleic Acid Chem.,* 2015, (62):4.63.1-4.63.20. Thus, Ochi had to use a post-synthetic approach to synthesize their 2'-O-MDTM-modified RNA molecules. See Ochi 2016; see also Biscans et al., *Org. Biomol. Chem.,* 2016, 14:7010-17, recognizing Ochi's post-synthetic approach to prepare 2'-O-MDTM-modified RNA molecules as a way to avoid the instability of the disulfide bond in nucleoside phosphoramidites containing the 2'-O-MDTM group and proposing alternative post-synthetic approaches for preparing RNA containing various 2'-alkyldithiomethyl groups.

Notwithstanding the advances that have been made in the art to improve the stability of oligonucleotides and/or protect them from enzymes in the serum or in a cell, there remains a need in the art for improved strategies for the reversible modification of nucleic acid molecules, particularly reversible modifications that are compatible with standard, phosphoramidite oligonucleotide synthesis.

SUMMARY

This application discloses various new glutathione-sensitive, reversibly modified nucleotides and nucleosides that can be incorporated into any oligonucleotide of interest, including nucleic acid inhibitor molecules, such as siRNA, antisense oligonucleotides, microRNA, ribozymes, antagomirs, and aptamers. They can also be incorporated into other oligonucleotides, such as, Clustered Regularly Interspaced Short Palindromic Repeats (CRISPR) nucleic acids, nucleic acids for gene therapy, nucleic acids for DNA editing, probes, or any other oligonucleotide that is susceptible to degradation by nucleases and/or harsh environmental conditions (e.g., pH), including other oligonucleotides that are to be administered in vivo.

The glutathione-sensitive reversible modifications of the invention can also be used to reversibly modify nucleotide and nucleoside monomers, including glutathione-sensitive nucleoside phosphoramidites that can be used, for example, in standard oligonucleotide synthesis methods. In addition, glutathione-sensitive nucleotide and nucleoside monomers without a phosphoramidite can be used therapeutically, for example as anti-viral agents.

Typically, the glutathione-sensitive moiety is used to reversibly modify the 2'-carbon of a sugar moiety in the nucleotide, although other carbon positions may also be modified with the glutathione-sensitive moiety. One or more glutathione-sensitive nucleotides can be incorporated into an oligonucleotide to help protect the oligonucleotide during in vivo administration (e.g., transit through the blood and/or the lysosomal/endosomal compartments of a cell) where the oligonucleotide will be exposed to nucleases and other harsh environmental conditions (e.g., pH). When the reversibly modified oligonucleotide is released into the cytosol, the intracellular conditions, including a high level of glutathione, cause the glutathione-sensitive moiety to be removed from the oligonucleotide. In certain embodiments, the removal of the glutathione-sensitive moiety yields a hydroxyl group at the 2'-carbon position, which is the natural substituent for a ribonucleotide at that position (see, e.g., Scheme 7 in Example 3).

Using reversible, glutathione-sensitive moieties according to the teachings of the instant application, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

Moreover, the present reversibly modified, glutathione-sensitive oligonucleotides, can be synthesized using conventional solid-phase synthesis. Accordingly, these reversibly modified, glutathione-sensitive oligonucleotides are readily prepared and are suitable for use in therapeutic applications. In addition, because the nucleic acids can be synthesized using conventional solid-phase synthesis, the glutathione-sensitive nucleotides can be incorporated into a nucleic acid molecule at selected positions in the oligonucleotide depending on the desired effect. The incorporation of the glutathione-sensitive moiety at specific positions of an oligonucleotide, such as a nucleic acid inhibitor molecule, can affect the properties of the oligonucleotide. For example, the glutathione-sensitive moiety can be incorporated at nucleotide position 1 (i.e., the 5'-terminal nucleotide) of a nucleic acid inhibitor molecule, which increases the stability of the molecule as compared to a molecule that has a 2'-F at nucleotide position 1.

With this technology, it is now possible to readily synthesize therapeutically useful, glutathione-sensitive oligonucleotides having the glutathione-sensitive moiety incorporated at one or more nucleotide positions of interest. Thus, in one aspect, the glutathione-sensitive oligonucleotides described herein can be used as pharmaceuticals and formulated with a pharmaceutically acceptable excipient as a pharmaceutical composition and used, for example, to edit genomic DNA or to modulate the expression of target genes and to treat patients in need thereof.

In certain aspects, the present disclosure is directed to oligonucleotides that contain one or more reversibly modified nucleotides, where the reversibly modified nucleotide comprises a glutathione-sensitive moiety attached to the 2'-carbon of the sugar ring (or analog thereof). In certain embodiments, the glutathione-sensitive moiety is represented by Formula II, III, or IV, or any of the sub genera thereof, as described herein, including, for example, Formula IIa, IIIa, IIIa(i), IIIb, and IIIb(i); Formula IVa, IVb, IVc, IVd, or IVe; Formula IVa(i), IVb(i), IVb(ii), IVc(i), or IVd(i); or Formula IVe(i), IVe(ii), IVe(iii), IVe(iv), IVe(v), IVe(vi), IVe(vii), IVe(viii), IVe(ix), IVe(x), or IVe(xi). In embodiments where the oligonucleotide contains more than one reversibly modified nucleotide, each reversibly modified nucleotide may comprise the same glutathione-sensitive moiety or at least one of the reversibly modified nucleotides may contain a glutathione-sensitive moiety that is different from the at least one glutathione-sensitive moiety in the other reversibly modified nucleotides of the oligonucleotide. In certain embodiments, each reversibly modified nucleotide of the oligonucleotide comprises a different glutathione-sensitive moiety.

In certain aspects, the present disclosure is directed to a pharmaceutical composition comprising a pharmaceutically acceptable carrier and a therapeutically effective amount of a glutathione-sensitive oligonucleotide comprising at least one nucleotide comprising a glutathione-sensitive moiety attached to the 2'-carbon of the sugar moiety (or analog thereof).

In certain embodiments, the glutathione-sensitive oligonucleotide comprises at least one nucleotide represented by Formula I, as described herein, wherein L is a glutathione-sensitive moiety selected from Formula II, III, or IV, as described herein, or any of the sub genera thereof, as described herein, including, for example, Formula IIa, IIIa, IIIa(i), IIIb, and IIIb(i); Formula IVa, IVb, IVc, IVd, or IVe; Formula IVa(i), IVb(i), IVb(ii), IVc(i), or IVd(i); or Formula IVe(i), IVe(ii), IVe(iii), IVe(iv), IVe(v), IVe(vi), IVe(vii), IVe(viii), IVe(ix), IVe(x), or IVe(xi).

In certain embodiments of the glutathione-sensitive oligonucleotide, L is represented by Formula II, as described herein, wherein Y is O; wherein Z is NR', wherein R' is hydrogen or substituted or unsubstituted aliphatic; and wherein V is C and optionally wherein $X_2$ and $X_3$ are independently selected from hydrogen, halogen, nitro or amino.

In certain embodiments, L is represented by Formula IIa, as described herein.

In certain embodiments of the glutathione-sensitive oligonucleotide, L is represented by Formula III, as described herein, wherein Y is O, S or NH; wherein $Z_1$ is N or CH; wherein V is C; and optionally, wherein $M_1$ and $M_2$ are substituted or unsubstituted $C_2$ to $C_6$ alkyl or are taken together with $P_1$ to $Q_1$ to form a 5-8 membered ring, wherein the ring is substituted or unsubstituted cycloalkyl.

In certain embodiments, L is represented by Formula IIIa, as described herein, wherein Y is O, S or NH; and $Z_1$ is N or CR', wherein R' is selected from hydrogen, halogen, substituted or unsubstituted aliphatic, substituted or unsubstituted aryl, substituted or unsubstituted heteroaryl, substituted or unsubstituted heterocycle. In one embodiment, Y is O and $Z_1$ is N (see Formula IIIa(i)).

In certain embodiments, L is represented by Formula IIIb, as described herein, wherein Y is O, S or NH; $Z_1$ is N or CR', wherein R' is selected from hydrogen, halogen, substituted or unsubstituted aliphatic, substituted or unsubstituted aryl, substituted or unsubstituted heteroaryl, substituted or unsubstituted heterocycle; and $T_a$ and $T_b$ are each independently absent or selected from $CH_3$, substituted or substituted aliphatic, substituted or unsubstituted aryl, substituted or unsubstituted heteroaryl, substituted or unsubstituted hetero- cycle or a ligand optionally connected via spacer to a sulfur atom. In one embodiment, L is represented by Formula IIIb(i), as described herein.

In certain embodiments of the glutathione-sensitive oligonucleotide, L is represented by Formula IV, as described herein, wherein Y is O, S or NH; wherein Z is NH or $NCH_3$; wherein V is C; wherein G is $CH_2$ and E is absent or G is absent and E is $CH_2$; and optionally wherein $M_3$ and $M_4$ are independently substituted or unsubstituted $C_2$ to $C_6$ alkyl or taken together to form a 5-8 membered ring, wherein the ring is substituted or unsubstituted cycloalkyl.

In certain embodiments, L is represented by Formula IVa, as described herein, wherein Y is O, S, NH; wherein Z is O, S or NH, wherein $R_5$, $R_6$, and $R_7$ are each independently selected from OAcyl, NHR', NR', CR'R", wherein R' and R" are each independently selected from hydrogen, halogen, $CH_2$, CH, substituted aliphatic or unsubstituted aliphatic, aryl, heteroaryl, heterocyclic, or can be taken together to form a heterocyclic ring; and wherein T is a branched or unbranched $C_2$-$C_6$ alkyl or a ligand optionally connected via a spacer to a sulfur atom. In one embodiment, L is represented by Formula IVa(i), as described herein.

In certain embodiments, L is represented by Formula IVb wherein Y is O, S, NH; Z is O, S or NH; V is C; $M_3$ and $M_4$ are hydrogen; K is CH or a substituted or unsubstituted aliphatic; E is NH or NR', wherein R' is substituted or unsubstituted aliphatic; n is 0-5; T is substituted or unsubstituted $C_2$ to $C_6$ alkyl, substituted or unsubstituted aryl, substituted or unsubstituted heteroaryl or T is a ligand optionally connected via a spacer to a sulfur atom. In certain embodiments, L is represented by Formula IVb(i) or IVb(ii), as described herein, wherein R is selected from hydrogen, $CH_3$, substituted or unsubstituted aliphatic, aryl, heteroaryl, cycloalkyl or a heterocycle or R is a targeting ligand optionally connected via a spacer.

In certain embodiments, L is represented by Formula IVc, as described herein, wherein Y is O, S, NH; Z is selected from O, S, or NR', wherein R' is selected from hydrogen, halogen, $CH_3$, substituted or unsubstituted aliphatic, substituted or unsubstituted aryl, substituted or unsubstituted heteroaryl, substituted or unsubstituted heterocycle; V is C; $M_3$ and $M_4$ are taken together to form a 5-8 membered ring, wherein the ring is a substituted or unsubstituted cycloalkyl, optionally substituted with a heteroatom; K is a branched or unbranched substituted or unsubstituted $C_2$ to $C_6$ alkyl; n is 0-5; T is substituted or unsubstituted $C_2$ to $C_6$ alkyl, substituted or unsubstituted aryl, substituted or unsubstituted heteroaryl or T is a ligand optionally connected via a spacer; wherein R is selected from hydrogen, $CH_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via a spacer. In one embodiment, L is represented by Formula IVc(i), as described herein, wherein R is selected from hydrogen, $CH_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via a spacer.

In certain embodiments, L is represented by Formula IVd, as described herein, wherein Y is O, S, NH; Z is selected from O, S, NH, or $NCH_3$; T is substituted or unsubstituted $C_2$ to $C_6$ alkyl, substituted or unsubstituted aryl, substituted or unsubstituted heteroaryl or T is a ligand optionally connected via a spacer to a sulfur atom; and R is selected from hydrogen, CH$_3$ or a substituted or unsubstituted C$_2$ to C$_6$ alkyl. In one embodiment, L is represented by Formula IVd(i), as described herein.

In certain embodiments of the glutathione-sensitive oligonucleotide, L is represented by Formula IVe, as described herein, wherein Y is O, S, NH; Z is selected from O, S, or NR', wherein R' is selected from hydrogen, halogen, CH$_3$, substituted or unsubstituted aliphatic, substituted or unsubstituted aryl, substituted or unsubstituted heteroaryl, substituted or unsubstituted heterocycle; V is C or SO; G and E can be each independently absent, or selected from CH$_2$, CHR', CR'R", NH, NR', wherein R' and R" are each independently selected from hydrogen, halogen, a substituted or unsubstituted aliphatic, a substituted or unsubstituted aryl, a substituted or unsubstituted heteroaryl, a substituted or unsubstituted heterocycle or R' and R" are taken together to form a heterocyclic ring; K is C or CH; n is 0-5; T is substituted or unsubstituted C$_2$ to C$_6$ alkyl, substituted or unsubstituted aryl, substituted or unsubstituted heteroaryl or T is a ligand optionally connected via a spacer; wherein R is selected from hydrogen, CH$_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via a spacer. In certain embodiments, Z is NH or NCH$_3$ and one or both of G and E are absent, CH$_2$, or CR'R", NH, NR', wherein R' and R" are each independently selected from hydrogen or substituted or unsubstituted aliphatic. In certain embodiments, L is represented by Formula IVe(i), IVe(ii), IVe(iii), IVe(iv), IVe(v), IVe(vi), IVe(vii), IVe(viii), IVe(ix), IVe(x), or IVe (xi), as described herein, wherein R is selected from hydrogen, CH$_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via a spacer.

In certain embodiments, the glutathione-sensitive oligonucleotide comprises at least one nucleotide represented by Formula VIIe(ix), wherein A is absent, a hydrogen, a phosphate group, or a phosphate mimic; wherein U$_1$ is O or an internucleotide linking group attaching the at least one nucleotide represented by Formula VIIe(ix) to a nucleotide or an oligonucleotide; wherein B is a natural nucleobase; wherein U$_2$ is O; wherein W is hydrogen or an internucleotide linking group attaching the at least one nucleotide represented by Formula VIIe(ix) to a nucleotide or an oligonucleotide, wherein at least one of U$_1$ or W is an internucleotide linking group attaching the at least one nucleotide represented by Formula VIIe(ix) to an oligonucleotide and provided that if U$_1$ is an internucleotide linking group, A is absent; and wherein the glutathione-sensitive oligonucleotide is a double-stranded RNAi inhibitor molecule comprising a sense strand and an antisense strand.

In certain embodiments, A is hydrogen and W is an internucleotide linking group attaching the at least one nucleotide represented by Formula VIIe(ix) to an oligonucleotide and the at least one nucleotide represented by Formula VIIe(ix) is located at nucleotide position 1 of the antisense strand.

In certain embodiments, A is absent; W is a internucleotide linking group attaching the at least one nucleotide represented by Formula VIIe(ix) to a first oligonucleotide; and U$_1$ is a internucleotide linking group attaching the at least one nucleotide represented by Formula VIIe(ix) to a second oligonucleotide; and the at least one nucleotide represented by Formula VIIe(ix) is located at nucleotide position 14 of the antisense strand.

In certain embodiments, the glutathione-sensitive oligonucleotide comprises at least one nucleotide represented by Formula VIIe(xi), wherein A is absent, a hydrogen, a phosphate group, or a phosphate mimic; wherein U$_1$ is O or an internucleotide linking group attaching the at least one nucleotide represented by Formula VIIe(xi) to a nucleotide or an oligonucleotide; wherein B is a natural nucleobase; wherein U$_2$ is O; wherein W is hydrogen or an internucleotide linking group attaching the at least one nucleotide represented by Formula VIIe(xi) to a nucleotide or an oligonucleotide, wherein at least one of U$_1$ or W is an internucleotide linking group attaching the at least one nucleotide represented by Formula VIIe(xi) to an oligonucleotide and provided that if U$_1$ is an internucleotide linking group, A is absent; and wherein the glutathione-sensitive oligonucleotide is a double-stranded RNAi inhibitor molecule comprising a sense strand and an antisense strand.

In certain embodiments, the internucleotide linking group contains a phosphorous atom.

In certain embodiments, the oligonucleotide is a double-stranded oligonucleotide comprising a first strand and a second strand.

In certain embodiments, the double stranded oligonucleotide is a double-stranded RNAi inhibitor molecule and the first strand and comprises a sense strand and the second strand comprises an antisense strand. In certain embodiments, the double stranded RNAi inhibitor molecule comprises a region of complementarity between the sense strand and the antisense strand of about 15 to 45, 20 to 30, 21 to 26, 19 to 24, or 19 to 21 nucleotides.

In certain embodiments, the at least one nucleotide represented by Formula I is located on the antisense strand. In certain embodiments, the at least one nucleotide represented by Formula I is located on the sense strand.

In certain embodiments, the at least one nucleotide represented by Formula I is located at nucleotide position 1 of the antisense strand. In certain embodiments, the at least one nucleotide represented by Formula I is located at nucleotide position 14 of the antisense strand. In certain embodiments, the at least one nucleotide represented by Formula I is located at one or more nucleotide positions at or adjacent to the Ago2 cleavage site of the sense strand. In certain embodiments, the at least one nucleotide represented by Formula I is located at one, two, or three nucleotides that are immediately 5' or 3' of the Ago2 cleavage site. In certain embodiments, the at least one nucleotide represented by Formula I is located on both sides of the Ago2 cleavage site, e.g., at one or more nucleotides that are immediately 5' of the Ago2 cleavage site and at one or more nucleotides that are immediately 3' of the Ago2 cleavage site.

In certain embodiments, the double stranded RNAi inhibitor molecule contains a tetraloop.

In certain embodiments, the glutathione-sensitive oligonucleotide is a single stranded oligonucleotide. In certain embodiments, the single stranded oligonucleotide is a single stranded RNAi inhibitor molecule. In certain embodiments, the single-stranded oligonucleotide is a conventional antisense oligonucleotide, a ribozyme, microRNA, antagomir, or an aptamer. In certain embodiments, the single stranded RNAi inhibitor molecule is about 14-50, 16-30, 18-22, or 20-22 nucleotides in length.

In certain embodiments, the glutathione-sensitive oligonucleotide contains 1-5 nucleotides represented by Formula I. In certain embodiments, every nucleotide of the glutathione-sensitive oligonucleotide is modified and wherein every nucleotide that is not modified with the glutathione-sensitive moiety is modified with an irreversible modification.

In certain embodiments, the glutathione-sensitive oligonucleotide further comprises a delivery agent, wherein the delivery agent facilitates transport of the glutathione-sensitive oligonucleotide across an outer membrane of a cell. In certain embodiments, the delivery agent is selected from the group consisting of carbohydrates, peptides, lipids, vitamins and antibodies. In certain embodiments, the delivery agent is selected from N-Acetylgalactosamine (GalNAc), mannose-6-phosphate, galactose, oligosaccharide, polysaccharide, cholesterol, polyethylene glycol, folate, vitamin A, vitamin E, lithocholic acid and a cationic lipid.

In certain embodiment, the glutathione-sensitive oligonucleotide is contained in a lipid nanoparticle. In certain embodiments, the glutathione-sensitive oligonucleotide is a naked, glutathione-sensitive oligonucleotide.

In certain embodiments, the glutathione-sensitive oligonucleotide comprises at least one nucleotide having a glutathione-sensitive moiety bound to an oxygen atom that is covalently bound to a 2'-carbon of a sugar moiety of the nucleotide, wherein the glutathione-sensitive oligonucleotide is prepared by a phosphoramidite-based oligonucleotide synthesis method using a nucleoside phosphoramidite having a glutathione-sensitive moiety.

In certain embodiments, the glutathione-sensitive oligonucleotide is a Clustered Regularly Interspaced Short Palindromic Repeats "CRISPR" nucleic acid sequence having a crRNA sequence having a first portion capable of hybridizing to a target sequence in a cell and/or a tracrRNA sequence that hybridizes with a second portion of the crRNA sequence to form a guide sequence. In certain embodiments, the guide sequence is a chimeric guide sequence, wherein the crRNA sequence is fused to the tracrRNA sequence.

In certain aspects, the present disclosure is directed to a pharmaceutical composition comprising a glutathione-sensitive oligonucleotide as described herein and a pharmaceutically acceptable excipient and methods of using the same. In certain embodiments, the glutathione-sensitive oligonucleotide comprises at least one glutathione-sensitive nucleotide, wherein the at least one glutathione-sensitive nucleotide comprises a substitution of a hydroxyl group at the 2'-carbon of a ribose or analog thereof with a glutathione-sensitive moiety. In certain embodiments, the glutathione-sensitive oligonucleotide is a double stranded RNAi inhibitor molecule. In certain aspects, the present disclosure is directed to a method for reducing expression of a target gene in a subject comprising administering a pharmaceutical composition comprising a glutathione-sensitive double-stranded RNAi inhibitor molecule to a subject in need thereof in an amount sufficient to reduce expression of the target gene. In certain embodiments, the administering comprises systemic administration.

In certain aspects, the present disclosure is directed to a nucleoside comprising a phosphoramidite and a glutathione-sensitive moiety, wherein the nucleoside is compatible with phosphoramidite-based oligonucleotide synthesis. In certain embodiments, the phosphoramidite is bound to the 5'- or 3'-carbon of the sugar moiety of the nucleoside and the glutathione-sensitive moiety is bound to an oxygen atom that is covalently bound to the 2'-carbon of the sugar moiety of the nucleoside. In certain embodiments of the nucleoside phosphoramidite, the glutathione-sensitive moiety is represented by Formula II, Formula III, or Formula IV or any subgenera thereof, including Formula IIa, IIIa, IIIb, IIIa(i), IIIb(i), IVa, IVb, IVc, IVd, IVe, IVa(i), IVb(i), IVb(ii), IVc(i), IVd(i), IVe(i), IVe(ii), IVe(iii), IVe(iv), IVe(v), IVe (vi), IVe(vii), IVe(viii), IVe(ix), IVe(x), or IVe(xi), as described herein.

In certain aspects, the present disclosure is directed to a glutathione-sensitive nucleoside phosphoramidite, wherein the nucleoside phosphoramidite is represented by Formula VIII, as described herein. In certain embodiments, the nucleoside phosphoramidite is represented by Formula IX. In certain embodiments, the glutathione-sensitive moiety ($L_1$) comprises a disulfide bridge or a sulfonyl group.

In certain embodiments, the nucleoside phosphoramidite is represented by Formula VIII, wherein J is O; B is a natural nucleobase; $U_2$ is O; I is $CH_2$; $W_1$ is a phosphoramidite; $A_1$ is a protecting group, hydrogen, or solid support; and $U_3$ is O and optionally, wherein X is O and $R_1$, $R_2$, $R_3$ and $R_4$ are hydrogen.

In certain embodiments, the nucleoside phosphoramidite is represented by Formula VIII, wherein J is O; B is a natural nucleobase; $U_2$ is O; I is $CH_2$; $W_1$ is a protecting group, hydrogen or solid support; $A_1$ is a phosphoramidite, and $U_3$ is O and optionally, wherein X is O and $R_1$, $R_2$, $R_3$ and $R_4$ are hydrogen.

In certain embodiments, the nucleoside phosphoramidite is represented by Formula X, wherein $R_8$ is H or a protecting group; $R_7$ is a phosphoramidite; B is a natural nucleobase; X is O; and wherein $L_1$ is represented by Formula IVe(ix).

In certain embodiments, the nucleoside phosphoramidite is represented by Formula X, wherein $R_8$ is H or a protecting group; $R_7$ is a phosphoramidite; B is a natural nucleobase; and X is O; and wherein $L_1$ is represented by Formula IVe(xi).

In certain embodiments, the phosphoramidite has the formula —P(OR$^x$)—N(R$^y$)$_2$, wherein R$^x$ is selected from the group consisting of an optionally substituted methyl, 2-cyanoethyl and benzyl, wherein each of R$^y$ is selected from the group consisting of an optionally substituted ethyl and isopropyl.

In certain aspects, the present disclosure is directed to a method for preparing a glutathione-sensitive oligonucleotide comprising: (a) attaching a nucleoside to a solid support via a covalent linkage; (b) coupling the glutathione-sensitive nucleoside phosphoramidite, as described herein, to a hydroxyl group on the nucleoside of step (a) to form a phosphorus nucleoside linkage therebetween, wherein any uncoupled nucleoside on the solid support is capped with a capping reagent; (c) oxidizing said phosphorus nucleoside linkage with an oxidizing reagent; and (d) repeating steps (b) to (d) iteratively with one or more subsequent glutathione-sensitive nucleoside phosphoramidites, as described herein, or one or more subsequent nucleoside phosphoramidites that do not contain a glutathione-sensitive moiety, to form the glutathione-sensitive oligonucleotide; and (f) optionally removing said glutathione-sensitive oligonucleotide from said solid support. In another aspect, the present disclosure is directed to an oligonucleotide made by the method. In certain embodiments, the glutathione-sensitive moiety comprises a disulfide bridge or sulfonyl group, including, for example, the glutathione-sensitive moiety represented by Formula II, III, or IV, as described herein, or any of the subgenera thereof, including Formula IIa, IIIa, IIIb, IIIa(i), IIIb(i), IVa, IVb, IVc, IVd, IVe, IVa(i), IVb(i), IVb(ii), IVc(i), IVd(i), IVe(i), IVe(ii), IVe(iii), IVe(iv), IVe(v), IVe (vi), IVe(vii), IVe(viii), IVe(ix), IVe(x), or IVe(xi), as described herein. In certain aspects, the present disclosure is directed to a glutathione-sensitive nucleoside or nucleotide that does not contain a phosphoramidite, wherein the glutathione-sensitive nucleoside or nucleotide comprises a glutathione-sensitive moiety that is bound to an oxygen atom that is covalently bound to the 2'-carbon of the sugar moiety of the nucleotide or nucleoside; and wherein the glutathione-sensitive moiety is represented by Formula II, Formula III, or Formula IV, as described herein, or any subgenera thereof.

In certain embodiments, the glutathione-sensitive nucleoside or nucleotide is represented by Formula XI, as described herein. In certain embodiments, J is O; X is O; $L_2$ is a glutathione-sensitive moiety represented by Formula II, III, or IV; $W_2$ is hydrogen, halogen, OR', SR', NR'R'', a substituted or unsubstituted aliphatic, a substituted or unsubstituted aryl, a substituted or unsubstituted heteroaryl, a substituted or unsubstituted cycloalkyl, a substituted or unsubstituted heterocycle, wherein R' and R'' are each independently selected from hydrogen, halogen, a substituted or unsubstituted aliphatic, an aryl, a heteroaryl, a heterocycle or are taken together to form a heterocyclic ring; and $A_2$ is absent, hydrogen, a phosphate group, a phosphate mimic, or a phosphoramidate; and optionally wherein $R_1$, $R_2$, $R_3$, and $R_4$ are hydrogen; $U_2$ is oxygen; $W_2$ is hydrogen; I is $CH_2$; $U_3$ is O; and $A_2$ is hydrogen or a phosphate group.

DETAILED DESCRIPTION

Definitions

Figure 1A:
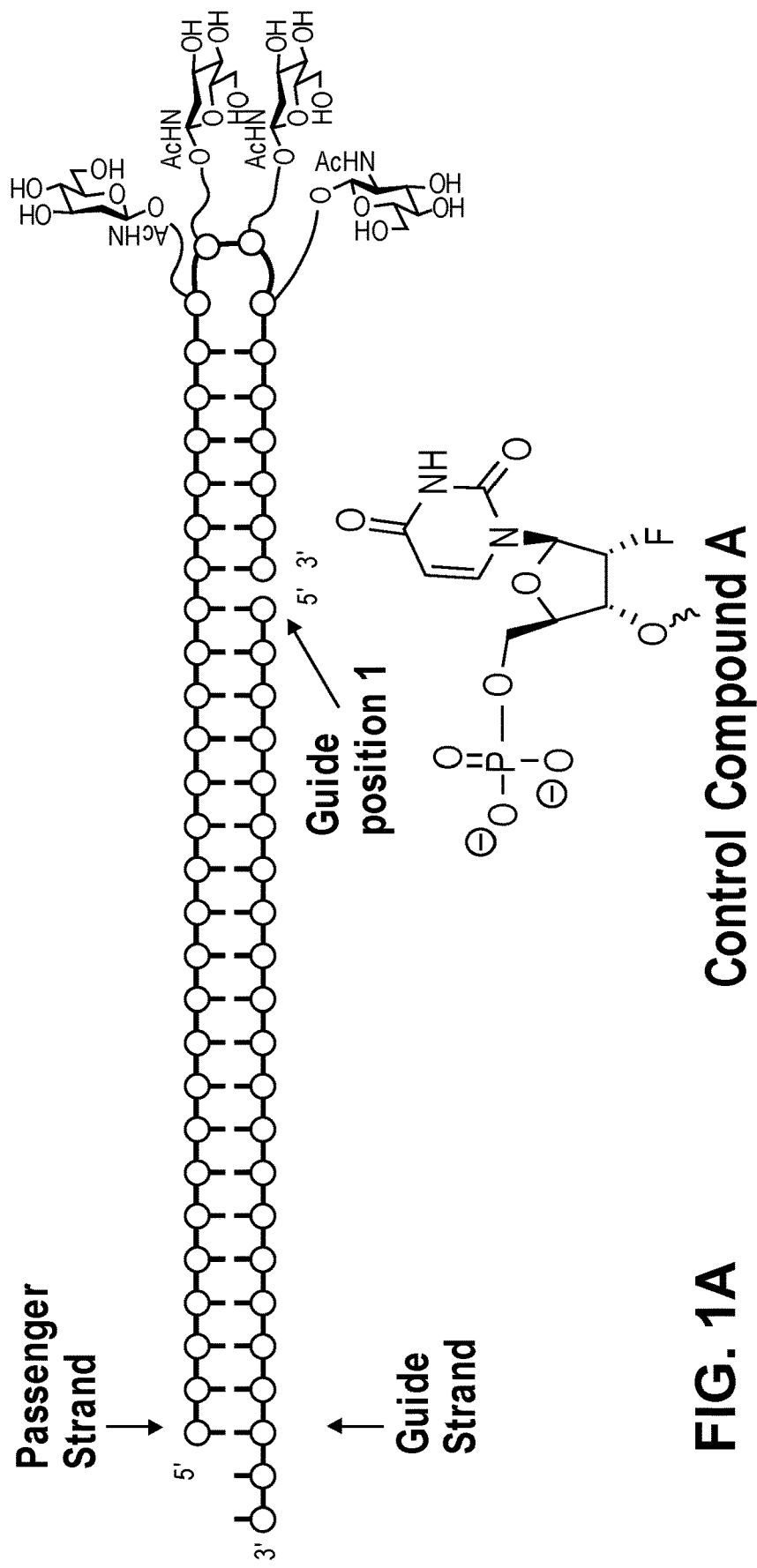
FIG. 1A-1B depict examples of four representative double stranded RNAi inhibitor molecules as described in the Examples: Control Compound A and Control Compound B (FIG. 1A) and Test Compound 1 and Test Compound 2 (FIG. 1B). Test Compounds 1 and 2 contain the indicated glutathione-sensitive moiety at the 2'-carbon at nucleotide positions 1 ("Guide position 1") and 14 ("Guide position 14"), respectively, of the guide strand of the double stranded RNAi inhibitor molecules, according to the present disclosure. Except for the glutathione-sensitive nucleotide at nucleotide position 1 and 14 of the guide strands of Test Compounds 1 and 2, respectively, the remaining nucleotides in Test Compounds 1 and 2 were irreversibly modified with either 2'-F or 2'-OMe. Control Compounds A and B are identical to Test Compounds 1 and 2 except for the nucleotides at positions 1 and 14 of the guide strands. Control Compounds A and B contain a 2'-F at nucleotide position 1 of the guide strand ("Guide position 1"). Control Compound A differs from Control Compound B because it contains natural phosphate (5'-$PO_4^{2-}$) at the 5'-carbon of the 5'-terminal nucleotide of the guide strand, whereas Control Compound B contains a free hydroxyl group (5'-OH) at the 5'-carbon of the 5'-terminal nucleotide of the guide strand. The guide strands of Control Compounds A and B contain the same nucleotide sequence and, therefore, recognize the same target mRNA sequence as Test Compounds 1 and 2.
Figure 1A:
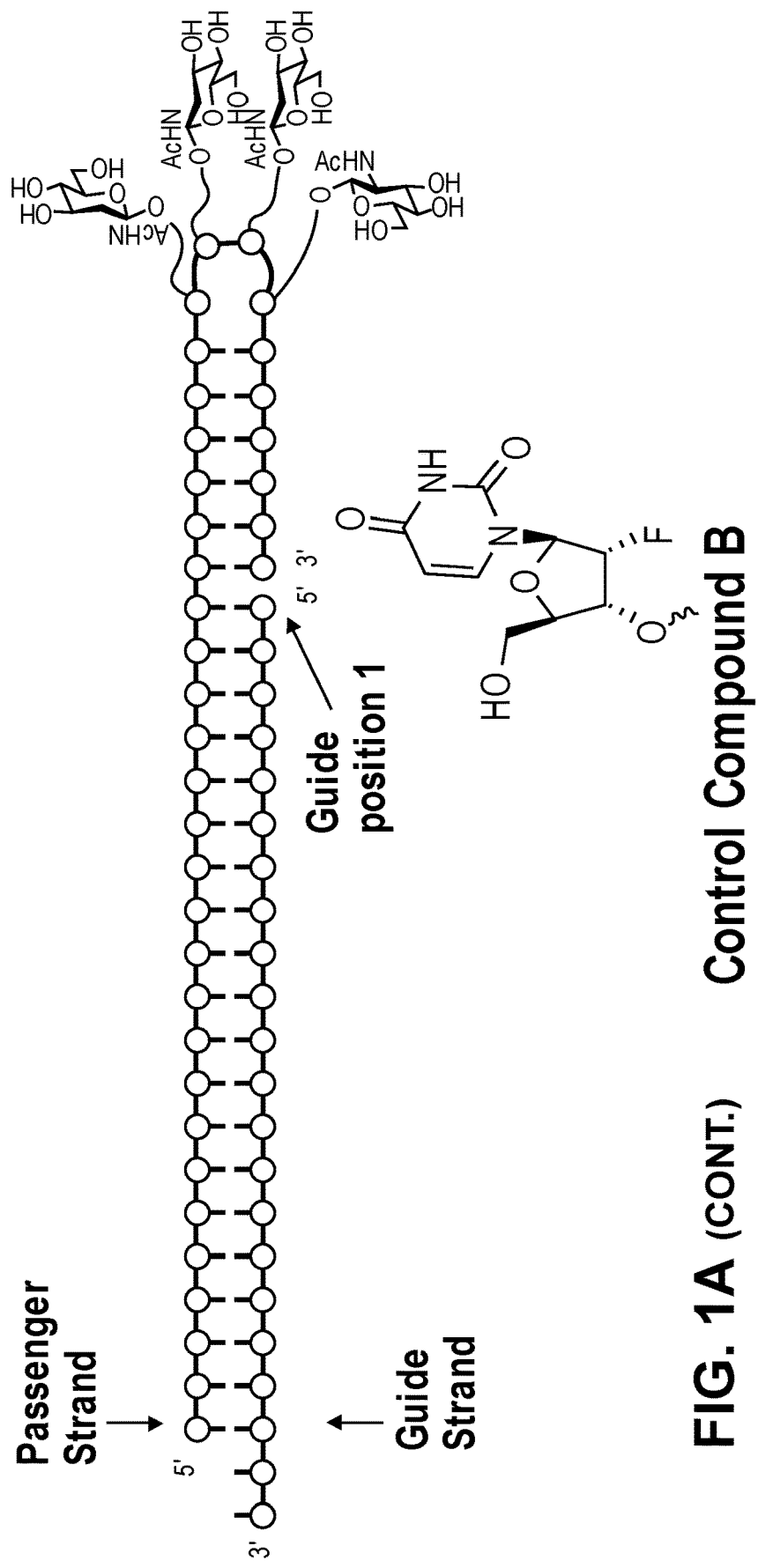

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Acyl: As used herein, the term "acyl" refers to an alkylcarbonyl, cycloalkylcarbonyl and arylcarbonyl moiety.

Aliphatic group: As used herein, the term "aliphatic group" refers to both saturated and unsaturated, straight chain (i.e., unbranched), or branched, hydrocarbons, which are optionally substituted with one or more functional groups. The term "substituted aliphatic" refers to aliphatic moieties bearing substituents.

Alkoxy: As used herein, the term "alkoxy" refers to an alkyl group attached to a molecular moiety through an oxygen atom.

Alkenyl: As used herein, the term "alkenyl" refers to straight or branched chain hydrocarbyl groups having at least one carbon-carbon double bond, and having in the range of about 2 to about 20 carbon atoms. "Substituted alkenyl" refers to alkenyl groups further bearing one or more substituents. As used herein, "lower alkenyl" refers to alkenyl moieties having from 2 to about 6 carbon atoms.

Alkyl: As used herein, the term "alkyl" refers to straight or branched chain hydrocarbyl groups having from 1 up to about 20 carbon atoms. Whenever it appears herein, a numerical range, such as "$C_1$-$C_6$ alkyl" means that an alkyl group may comprise only 1 carbon atom, 2 carbon atoms, 3 carbon atoms, etc., up to and including 6 carbon atoms, although the term "alkyl" also includes instances where no numerical range of carbon atoms is designated. For example, the term "alkyl" can refer to a sub-range between $C_1$-$C_{10}$ (e.g. $C_1$-$C_6$). "Substituted alkyl" refers to alkyl moieties bearing substituents. As used herein, "lower alkyl" refers to alkyl moieties having from 1 to about 6 carbon atoms.

Alkylamino: As used herein, the term "alkylamino" refers to an alkyl radical bearing an amine functionality. Alkylaminos may be substituted or unsubstituted.

Alkynyl: As used herein, "alkynyl" refers to straight or branched chain hydrocarbyl groups having at least one carbon-carbon triple bond, and having in the range of about 2 to about 20 carbon atoms. "Substituted alkynyl" refers to alkynyl groups further bearing one or more substituents. As used herein, "lower alkynyl" refers to alkynyl moieties having from about 2 to about 6 carbon atoms.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11, 1%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aptamer: As used herein, the term "aptamer" refers to an oligonucleotide that has binding affinity for a specific target including a nucleic acid, a protein, a specific whole cell or a particular tissue. Aptamers may be obtained using methods known in the art, for example, by in vitro selection from a large random sequence pool of nucleic acids. Lee et al., *Nucleic Acid Res.,* 2004, 32:D95-D100.

Antagomir: As used herein, the term "antagomir" refers to an oligonucleotide that has binding affinity for a specific target including the guide strand of an exogenous RNAi inhibitor molecule or natural miRNA (Krutzfeldt et al. *Nature* 2005,438(7068):685-689).

Antisense strand: A double stranded RNAi inhibitor molecule comprises two oligonucleotide strands: an antisense strand and a sense strand. The antisense strand or a region thereof is partially, substantially or fully complementary to a corresponding region of a target nucleic acid. In addition, the antisense strand of the double stranded RNAi inhibitor molecule or a region thereof is partially, substantially or fully complementary to the sense strand of the double stranded RNAi inhibitor molecule or a region thereof. In certain embodiments, the antisense strand may also contain nucleotides that are non-complementary to the target nucleic acid sequence. The non-complementary nucleotides may be on either side of the complementary sequence or may be on both sides of the complementary sequence. In certain embodiments, where the antisense strand or a region thereof is partially or substantially complementary to the sense strand or a region thereof, the non-complementary nucleotides may be located between one or more regions of complementarity (e.g., one or more mismatches). The antisense strand of a double stranded RNAi inhibitor molecule is also referred to as the guide strand.

Aromatic Group: The term "aromatic group" as used herein refers to a planar ring having a delocalized π-electron system containing 4n+2π electrons, where n is an integer. Aromatic rings can be formed from five, six, seven, eight, nine, or more than nine atoms. The term "aromatic" is intended to encompass both carbocyclic aryl (e.g., phenyl) and heterocyclic aryl (or "heteroaryl" or "heteroaromatic") groups (e.g., pyridine). The term includes monocyclic or fused-ring polycyclic rings, i.e., rings which share adjacent pairs of carbon atoms. "Substituted aromatic" refers to an aromatic group further bearing one or more substituents.

Araliphatic: As used herein, the terms "araliphatic," "aryl aliphatic," or "aromatic aliphatic" are used interchangeably and refer to compounds that contain one or more aromatic moieties and one or more aliphatic moieties.

Aryl: As used herein, the term "aryl" refers to an aromatic monocyclic or multicyclic groups having in the range of 5 up to 19 carbon atoms. "Substituted aryl" refers to aryl groups further bearing one or more substituents.

Carboxylic: As used herein, "carboxylic", "carboxy" or "carboxyl" generally refers to the radical C(O)OH.

Canonical RNA inhibitor molecule: As used herein, the term "canonical RNA inhibitor molecule" refers to two strands of nucleic acids, each 21 nucleotides long with a central region of complementarity that is 19 base-pairs long for the formation of a double stranded nucleic acid and two nucleotide overhands at each of the 3'-ends.

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. "Fully complementarity" or 100% complementarity refers to the situation in which each nucleotide monomer of a first oligonucleotide strand or of a segment of a first oligonucleotide strand can form a base pair with each nucleotide monomer of a second oligonucleotide strand or of a segment of a second oligonucleotide strand. Less than 100% complementarity refers to the situation in which some, but not all, nucleotide monomers of two oligonucleotide strands (or two segments of two oligonucleotide strands) can form base pairs with each other. "Substantial complementarity" refers to two oligonucleotide strands (or segments of two oligonucleotide strands) exhibiting 90% or greater complementarity to each other. "Sufficiently complementary" refers to complementarity between a target mRNA and a nucleic acid inhibitor molecule, such that there is a reduction in the amount of protein encoded by a target mRNA.

Complementary strand: As used herein, the term "complementary strand" refers to a strand of a double stranded nucleic acid inhibitor molecule that is partially, substantially or fully complementary to the other strand.

Conventional antisense oligonucleotide: As used herein, the term "conventional antisense oligonucleotide" refers to single stranded oligonucleotides that inhibit the expression of a targeted gene by one of the following mechanisms: (1) Steric hindrance, e.g., the antisense oligonucleotide interferes with some step in the sequence of events involved in gene expression and/or production of the encoded protein by directly interfering with, for example, transcription of the gene, splicing of the pre-mRNA and translation of the mRNA; (2) Induction of enzymatic digestion of the RNA transcripts of the targeted gene by RNase H; (3) Induction of enzymatic digestion of the RNA transcripts of the targeted gene by RNase L; (4) Induction of enzymatic digestion of the RNA transcripts of the targeted gene by RNase P: (5) Induction of enzymatic digestion of the RNA transcripts of the targeted gene by double stranded RNase; and (6) Combined steric hindrance and induction of enzymatic digestion activity in the same antisense oligo. Conventional antisense oligonucleotides do not have an RNAi mechanism of action like RNAi inhibitor molecules. RNAi inhibitor molecules can be distinguished from conventional antisense oligonucleotides in several ways including the requirement for Ago2 that combines with an RNAi antisense strand such that the antisense strand directs the Ago2 protein to the intended target(s) and where Ago2 is required for silencing of the target.

CRISPR RNA: Clustered Regularly Interspaced Short Palindromic Repeats ("CRISPR") is a microbial nuclease system involved in defense against invading phages and plasmids. Wright et al., *Cell*, 2016, 164:29-44. This prokaryotic system has been adapted for use in editing target nucleic acid sequences of interest in the genome of eukaryotic cells. Cong et al., *Science*, 2013, 339:819-23; Mali et al., *Science*, 2013, 339:823-26; Woo Cho et al., *Nat. Biotechnology*, 2013, 31(3):230-232. As used herein, the term "CRISPR RNA" refers to a nucleic acid comprising a "CRISPR" RNA (crRNA) portion and/or a trans activating crRNA (tracrRNA) portion, wherein the CRISPR portion has a first sequence that is partially, substantially or fully complementary to a target nucleic acid and a second sequence (also called the tracer mate sequence) that is sufficiently complementary to the tracrRNA portion, such that the tracer mate sequence and tracrRNA portion hybridize to form a guide RNA. The guide RNA forms a complex with an endonuclease, such as a Cas endonuclease (e.g., Cas9) and directs the nuclease to mediate cleavage of the target nucleic acid. In certain embodiments, the crRNA portion is fused to the tracrRNA portion to form a chimeric guide RNA. Jinek et al., Science, 2012, 337:816-21. In certain embodiments, the first sequence of the crRNA portion includes between about 16 to about 24 nucleotides, preferably about 20 nucleotides, which hybridize to the target nucleic acid. In certain embodiments, the guide RNA is about 10-500 nucleotides. In other embodiments, the guide RNA is about 20-100 nucleotides.

Cycloalkyl: As used herein, the term "cycloalkyl" refers to cyclic (i.e., ring-containing) hydrocarbon groups containing 3 to 12 carbons, for example, 3 to 8 carbons and, for example, 3 to 6 carbons. "Substituted cycloalkyl" refers to cycloalkyl groups further bearing one or more substituents.

Delivery agent: As used herein, the term "delivery agent" refers to a transfection agent or a ligand that is complexed with or bound to an oligonucleotide and which mediates its entry into cells. The term encompasses cationic liposomes, for example, which have a net positive charge that binds to the oligonucleotide's negative charge. This term also encompasses the conjugates as described herein, such as GalNAc and cholesterol, which can be covalently attached to an oligonucleotide to direct delivery to certain tissues. Further specific suitable delivery agents are also described herein.

Deoxyribonucleotide: As used herein, the term "deoxyribonucleotide" refers to a natural or modified nucleotide which has a hydrogen group at the 2'-position of the sugar moiety.

Disulfide: As used herein the term "disulfide" refers to a chemical compound containing the group

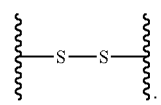

Typically, each sulfur atom is covalently bound to a hydrocarbon group. In certain embodiments, at least one sulfur atom is covalently bound to a group other than a hydrocarbon. The linkage is also called an SS-bond or a disulfide bridge.

Duplex: As used herein, the term "duplex" in reference to nucleic acids (e.g., oligonucleotides), refers to a double helical structure formed through complementary base pairing of two antiparallel sequences of nucleotides.

Excipient: As used herein, the term "excipient" refers to a non-therapeutic agent that may be included in a composition, for example to provide or contribute to a desired consistency or stabilizing effect.

Glutathione: As used herein, the term "glutathione" (GSH) refers to a tripeptide having the structure of Formula XIII, below. GSH is present in cells at a concentration of approximately 1-10 mM. GSH reduces glutathione-sensitive bonds, including disulfide bonds. In the process, glutathione is converted to its oxidized form, glutathione disulfide (GSSG). Once oxidized, glutathione can be reduced back by glutathione reductase, using NADPH as an electron donor.

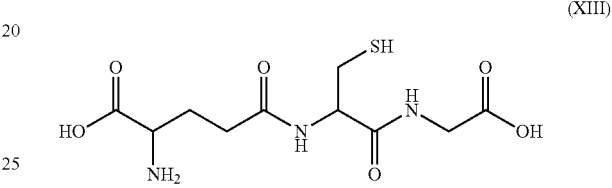

(XIII)

Glutathione-sensitive compound or glutathione-sensitive moiety: As used herein, the terms "glutathione-sensitive compound", or "glutathione-sensitive moiety", are used interchangeably and refers to any chemical compound (e.g., oligonucleotide, nucleotide, or nucleoside) or moiety containing at least one glutathione-sensitive bond, such as a disulfide bridge or a sulfonyl group. As used herein, a "glutathione-sensitive oligonucleotide" is an oligonucleotide containing at least one nucleotide containing a glutathione-sensitive bond.

Half-life: As used herein, the terms "serum half-life", "plasma half-life" and "vesicle half-life" refer to the amount of time by which half of an amount of a molecule, such as a reversibly modified oligonucleotide, is degraded or removed under a specific condition, e.g. in the presence of serum, plasma or in endosomal or lysosomal vesicles.

Halo: As used herein, the terms "halo" and "halogen" are interchangeable and refer to an atom selected from fluorine, chlorine, bromine and iodine.

Haloalkyl: As used herein, the term "haloalkyl" refers to an alkyl group having one or more halogen atoms attached thereto and is exemplified by such groups as chloromethyl, bromoethyl, trifluoromethyl, and the like.

Heteroaryl: As used herein, the term "heteroaryl" refers to an aromatic ring system containing at least one heteroatom selected from nitrogen, oxygen and sulfur. The heteroaryl ring can be fused or otherwise attached to one or more heteroaryl rings, aromatic or nonaromatic hydrocarbon rings or heterocycloalkyl rings.

Heterocycle: As used herein, the terms "heterocycle" or "heterocyclic" refer to nonaromatic cyclic (i.e., ring-containing) groups containing one or more heteroatoms (e.g., N, O, S, or the like) as part of the ring structure, and having in the range of 3 up to 14 carbon atoms. "Substituted heterocyclic" or "substituted heterocycle" refer to heterocyclic groups further bearing one or more substituents.

$IC_{50}$: As used herein, the term "$IC_{50}$" refers to a quantitative measure that indicates how much of a particular drug or other substance (inhibitor) is needed to inhibit a given biological process (e.g. expression of an mRNA) by half.

Internucleotide linking group: As used herein, the term "internucleotide linking group" or "internucleotide linkage" refers to a chemical group capable of covalently linking two nucleoside moieties. Typically, the chemical group is a phosphorus-containing linkage group containing a phospho or phosphite group. Phospho linking groups are meant to include a phosphodiester linkage, a phosphorodithioate linkage, a phosphorothioate linkage, a phosphotriester linkage, a thionoalkylphosphonate linkage, a thionalkylphosphotriester linkage, a phosphoramidite linkage, a phosphonate linkage and/or a boranophosphate linkage. Many phosphorus-containing linkages are well known in the art, as disclosed, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050. In other embodiments, the oligonucleotide contains one or more internucleotide linking groups that do not contain a phosphorous atom, such short chain alkyl or cycloalkyl internucleotide linkages, mixed heteroatom and alkyl or cycloalkyl internucleotide linkages, or one or more short chain heteroatomic or heterocyclic internucleotide linkages, including, but not limited to, those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; and amide backbones. Non-phosphorous containing linkages are well known in the art, as disclosed, for example, in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Loop: As used herein, the term "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins and tetraloops.

MicroRNA: As used herein, the terms "microRNA" "mature microRNA" "miRNA" and "miR" are interchangeable and refer to non-coding RNA molecules encoded in the genomes of plants and animals. Typically, mature microRNA are about 18-25 nucleotides in length. In certain instances, highly conserved, endogenously expressed microRNAs regulate the expression of genes by binding to the 3'-untranslated regions (3'-UTR) of specific mRNAs. Certain mature microRNAs appear to originate from long endogenous primary microRNA transcripts (also known as pre-microRNAs, pri-microRNAs, pri-mirs, pri-miRs or pri-pre-microRNAs) that are often hundreds of nucleotides in length (Lee, et al., EMBO J., 2002, 21(17), 4663-4670).

Modified nucleoside: As used herein, the term "modified nucleoside" refers to a nucleoside containing one or more of a modified or universal nucleobase or a modified sugar. The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A modified sugar (also referred herein to a sugar analog) includes modified deoxyribose or ribose moieties, e.g., where the modification occurs at the 2'-, 3'-, 4'-, or 5'-carbon position of the sugar. The modified sugar may also include non-natural alternative carbon structures such as those present in locked nucleic acids ("LNA") (see, e.g., Koshkin et al. (1998), *Tetrahedron*, 54, 3607-3630); bridged nucleic acids ("BNA") (see, e.g., U.S. Pat. No. 7,427,672 and Mitsuoka et al. (2009), *Nucleic Acids Res.*, 37(4):1225-38) and unlocked nucleic acids ("UNA") (see, e.g., Snead et al. (2013), *Molecular Therapy—Nucleic Acids,* 2, e103(doi: 10.1038/mtna.2013.36)). Suitable modified or universal nucleobases or modified sugars in the context of the present disclosure are described herein.

Modified nucleotide: As used herein, the term "modified nucleotide" refers to a nucleotide containing one or more of a modified or universal nucleobase, a modified sugar, or a modified phosphate group. The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A modified sugar (also referred herein to a sugar analog) includes modified deoxyribose or ribose moieties, e.g., where the modification occurs at the 2'-, 3'-, 4'-, or 5'-carbon position of the sugar. The modified sugar may also include non-natural alternative carbon structures such as those present in locked nucleic acids ("LNA") (see, e.g., Koshkin et al. (1998), *Tetrahedron,* 54, 3607-3630), bridged nucleic acids ("BNA") (see, e.g., U.S. Pat. No. 7,427,672 and Mitsuoka et al. (2009), *Nucleic Acids Res.,* 37(4):1225-38) and unlocked nucleic acids ("UNA") (see, e.g., Snead et al. (2013), *Molecular Therapy—Nucleic Acids,* 2, e103(doi: 10.1038/mtna.2013.36)). Modified phosphate groups refer to a modification of the phosphate group that does not occur in natural nucleotides and includes non-naturally occurring phosphate mimics as described herein, including phosphate mimics that include a phosphorous atom and anionic phosphate mimics that do not include phosphate (e.g. acetate). Modified phosphate groups also include non-naturally occurring internucleotide linking groups, including both phosphorous-containing internucleotide linking groups and non-phosphorous containing linking groups, as described herein. Suitable modified or universal nucleobases, modified sugars, or modified phosphates in the context of the present disclosure are described herein.

Naked glutathione-sensitive oligonucleotide: As used herein, the term "naked glutathione-sensitive oligonucleotide" refers to a glutathione-sensitive oligonucleotide as described herein, which is not formulated in a protective lipid nanoparticle or other protective formulation and is thus exposed to the blood and endosomal/lysosomal compartments when administered in vivo.

Natural nucleoside: As used herein, the term "natural nucleoside" refers to a heterocyclic nitrogenous base in N-glycosidic linkage with a sugar (e.g., deoxyribose or ribose or analog thereof). The natural heterocyclic nitrogenous bases include adenine, guanine, cytosine, uracil and thymine.

Natural nucleotide: As used herein, the term "natural nucleotide" refers to a heterocyclic nitrogenous base in N-glycosidic linkage with a sugar (e.g., ribose or deoxyribose or analog thereof) that is linked to a phosphate group. The natural heterocyclic nitrogenous bases include adenine, guanine, cytosine, uracil and thymine.

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. The nucleic acid inhibitor molecule may include ribonucleotides, deoxyribonucleotides, and/or modified nucleotides.

Nucleoside: As used herein, the term "nucleoside" refers to a natural nucleotide or a modified nucleoside.

Nucleotide: As used herein, the term "nucleotide" refers to a natural nucleotide or a modified nucleotide.

Nucleotide position: As used herein, the term "nucleotide position" refers to a position of a nucleotide in an oligonucleotide as counted from the nucleotide at the 5'-terminus.

Oligonucleotide: As used herein, the term "oligonucleotide" as used herein refers to a polymeric form of nucleotides ranging from 2 to 2500 nucleotides. Oligonucleotides may be single-stranded or double-stranded. In certain embodiments, the oligonucleotide has 500-1500 nucleotides, typically, for example, where the oligonucleotide is used in gene therapy. In certain embodiments, the oligonucleotide is single or double stranded and has 7-100 nucleotides. In another embodiment, the oligonucleotide is single or double stranded and has 15-50 nucleotides, typically, for example, where the oligonucleotide is a nucleic acid inhibitor molecule. In yet another embodiment, the oligonucleotide is single or double stranded and has 19-40 or 19-25 nucleotides, typically, for example, where the oligonucleotide is a double-stranded nucleic acid inhibitor molecule and forms a duplex of at least 18-26 base pairs. In other embodiments, the oligonucleotide is single stranded and has 15-25 nucleotides, typically, for example, where the oligonucleotide nucleotide is a single stranded RNAi inhibitor molecule. Typically, the oligonucleotide contains one or more phosphorous-containing internucleotide linking groups, as described herein. In other embodiments, the internucleotide linking group is a non-phosphorus containing linkage, as described herein.

Overhang: As used herein, the term "overhang" refers to terminal non-base pairing nucleotide(s) at either end of either strand of a double-stranded nucleic acid inhibitor molecule. In certain embodiments, the overhang results from one strand or region extending beyond the terminus of the complementary strand to which the first strand or region forms a duplex. One or both of two oligonucleotide regions that are capable of forming a duplex through hydrogen bonding of base pairs may have a 5'- and/or 3'-end that extends beyond the 3'- and/or 5'-end of complementarity shared by the two polynucleotides or regions. The single-stranded region extending beyond the 3'- and/or 5'-end of the duplex is referred to as an overhang.

Pharmaceutical composition: As used herein, the term "pharmaceutical composition" comprises a pharmacologically effective amount of an instant reversibly-modified oligonucleotide or other bioactive agent and a pharmaceutically acceptable excipient. As used herein, "pharmacologically effective amount" "therapeutically effective amount" or "effective amount" refers to that amount of a reversibly modified oligonucleotide of the present disclosure or other active agent effective to produce the intended pharmacological, therapeutic or preventive result.

Pharmaceutically acceptable excipient: As used herein, the term "pharmaceutically acceptable excipient" means that the excipient is one that is suitable for use with humans and/or animals without undue adverse side effects (such as toxicity, irritation, and allergic response) commensurate with a reasonable benefit/risk ratio.

Phosphate mimic: As used herein, the term "phosphate mimic" refers to a chemical moiety that mimics the electrostatic and steric properties of a phosphate group. Typically, a phosphate analog is positioned at the 5' terminal nucleotide of an oligonucleotide in place of a 5'-phosphate, which is often susceptible to enzymatic removal. In some embodiments, these 5'-phosphate mimics contain phosphatase-resistant linkages. Suitable phosphate mimics include 5'-phosphonates, such as 5'-methylenephosphonate (5'-MP) and 5'-(E)-vinylphosphonate (5'-VP) and 4'-phosphate analogs that are bound to the 4'-carbon of the sugar moiety (e.g., a ribose or deoxyribose or analog thereof) of the 5'-terminal nucleotide of an oligonucleotide, such as 4'-oxymethylphosphonate, 4'-thiomethylphosphonate, or 4'-aminomethylphosphonate, as described in U.S. Provisional Application No. 62/393,401, which is hereby incorporated by reference in its entirety. Other modifications have been developed for the 5'-end of oligonucleotides (see, e.g., U.S. Pat. No. 8,927,513; Prakash et al. *Nucleic Acids Res.*, 2015, 43(6):2993-3011; WO 2011/133871).

Phosphoramidite: As used herein, the term "phosphoramidite" refers to a nitrogen containing a trivalent phosphorus derivative. Examples of suitable phosphoramidites are described herein.

Potency: As used herein, "potency" refers to the amount of an oligonucleotide or other drug that must be administered in vivo or in vitro to obtain a particular level of activity against an intended target in cells. For example, an oligonucleotide that suppresses the expression of its target by 90% in a subject at a dosage of 1 mg/kg has a greater potency than an oligonucleotide that suppresses the expression of its target by 90% in a subject at a dosage of 100 mg/kg.

Protecting group: As used herein, the term "protecting group" is used in the conventional chemical sense as a group which reversibly renders unreactive a functional group under certain conditions of a desired reaction. After the desired reaction, protecting groups may be removed to deprotect the protected functional group. All protecting groups should be removable under conditions which do not degrade a substantial proportion of the molecules being synthesized.

Ribonucleotide: As used herein, the term "ribonucleotide" refers to a natural or modified nucleotide which has a hydroxyl group at the 2'-position of the sugar moiety.

Ribozyme: As used herein, the term "ribozyme" refers to a catalytic nucleic acid molecule that specifically recognizes and cleaves a distinct target nucleic acid sequence, which can be either DNA or RNA. Each ribozyme has a catalytic component (also referred to as a "catalytic domain") and a target sequence-binding component consisting of two binding domains, one on either side of the catalytic domain.

RNAi inhibitor molecule: As used herein, the term "RNAi inhibitor molecule" refers to either (a) a double stranded nucleic acid inhibitor molecule ("dsRNAi inhibitor molecule") having a sense strand (passenger) and antisense strand (guide), where the antisense strand or part of the antisense strand is used by the Argonaute 2 (Ago2) endonuclease in the cleavage of a target mRNA or (b) a single stranded nucleic acid inhibitor molecule ("ssRNAi inhibitor molecule") having a single antisense strand, where that antisense strand (or part of that antisense strand) is used by the Ago2 endonuclease in the cleavage of a target mRNA.

Sense strand: A double stranded RNAi inhibitor molecule comprises two oligonucleotide strands: an antisense strand and a sense strand. The sense strand or a region thereof is partially, substantially or fully complementary to the antisense strand of the double stranded RNAi inhibitor molecule or a region thereof. In certain embodiments, the sense strand may also contain nucleotides that are non-complementary to the antisense strand. The non-complementary nucleotides may be on either side of the complementary sequence or may be on both sides of the complementary sequence. In certain embodiments, where the sense strand or a region thereof is partially or substantially complementary to the antisense strand or a region thereof, the non-complementary nucleotides may be located between one or more regions of complementarity (e.g., one or more mismatches). The sense strand is also called the passenger strand.

Solid support: As used herein, "solid support" refers to a non-liquid and non-gaseous substance to which chemical compounds such as oligonucleotides can attach. The term encompasses a variety of materials including but not limited to gels, resins, beads, plastic, glass, silicon, metal and cellulose.

Spacer: As used herein, the term "spacer" refers to a molecule that couples a ligand to an oligonucleotide, nucleotide, or nucleoside. Spacers include, but are not limited to, —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), carbohydrates, a peptide, amide, carboxy, amine, oxyamine, oxyimine, thioether, disulfide, thiourea, sulfonamide, morpholino or biotin.

Substituent or substituted: The terms "substituent" or "substituted" as used herein refer to the replacement of hydrogen radicals in a given structure with the radical of a substituent. When more than one position in any given structure may be substituted with more than one substituent, the substituent may be either the same or different at every position unless otherwise indicated. As used herein, the term "substituted" is contemplated to include all permissible substituents that are compatible with organic compounds. The permissible substituents include acyclic and cyclic, branched and unbranched, carbocyclic and heterocyclic, aromatic and nonaromatic substituents of organic compounds. This disclosure is not intended to be limited in any manner by the permissible substituents of organic compounds.

Sulfonyl group: As used herein, the term "sulfonyl group" refers to a chemical compound containing the bivalent group, —SO$_2$—. In certain embodiments, the sulfur atom is covalently bound to two carbon atoms and two oxygen atoms. In other embodiments, the sulfur atom is covalently bound to a carbon atom, a nitrogen atom, and two oxygen atoms.

Systemic administration: As used herein, the term "systemic administration" refers to in vivo systemic absorption or accumulation of drugs in the blood stream followed by distribution throughout the entire body.

Target site: As used herein, the term "target site" "target sequence," "target nucleic acid", "target region," "target gene" are used interchangeably and refer to a RNA or DNA sequence that is "targeted," e.g., for cleavage mediated by an RNAi molecule that contains a sequence within its guide/antisense region that is partially, substantially, or fully or sufficiently complementary to that target sequence.

Tetraloop: As used herein, the term "tetraloop" refers to a loop (a single stranded region) that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the nucleotides in a tetraloop include but are not limited to non-Watson-Crick base pairing, stacking interactions, hydrogen bonding, and contact interactions (Cheong et al., *Nature,* 1990,346(6285):680-2; Heus and Pardi, *Science,* 1991, 253(5016):191-4). A tetraloop confers an increase in the melting temperature (Tm) of an adjacent duplex that is higher than expected from a simple model loop sequence consisting of random bases. For example, a tetraloop can confer a melting temperature of at least 50° C., at least 55° C., at least 56° C., at least 58° C., at least 60° C., at least 65° C. or at least 75° C. in 10 mM NaHPO4 to a hairpin comprising a duplex of at least 2 base pairs in length. A tetraloop may contain ribonucleotides, deoxyribonucleotides, modified nucleotides, and combinations thereof. In certain embodiments, a tetraloop consists of four nucleotides. In certain embodiments, a tetraloop consists of five nucleotides.

Examples of RNA tetraloops include the UNCG family of tetraloops (e.g., UUCG), the GNRA family of tetraloops (e.g., GAAA), and the CUUG tetraloop. (Woese et al., *PNAS,* 1990, 87(21):8467-71; Antao et al., *Nucleic Acids Res.,* 1991, 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). (Nakano et al. *Biochemistry,* 2002, 41(48):14281-14292. Shinji et al., *Nippon Kagakkai Koen Yokoshu,* 2000, 78(2):731).

I. INTRODUCTION

This application provides various new glutathione-sensitive nucleotides and nucleosides that can be incorporated into any oligonucleotide of interest, including, but not limited to, nucleic acid inhibitor molecules, such as dsRNAi, antisense, miRNA, and ssRNAi agents, as well as methods of using the glutathione-sensitive nucleic acid inhibitor molecules to modulate the expression of target genes and to treat patients in need thereof. Other oligonucleotides that can be reversibly modified with one or more glutathione-sensitive moieties in accordance with the disclosure of this application include, but are not limited to, Clustered Regularly Interspaced Short Palindromic Repeats (CRISPR) nucleic acids, nucleic acids for gene therapy, nucleic acids for DNA editing, and probes.

The reversibly modified oligonucleotide comprises one or more nucleotides having a glutathione-sensitive moiety, typically at the 2'-carbon of a sugar moiety. The one or more glutathione-sensitive nucleotides in the oligonucleotide help to stabilize the oligonucleotide during transit through the blood and the lysosomal/endosomal compartments of a cell and protect the oligonucleotide from nucleases and other environmental conditions (e.g., pH) encountered during in vivo administration. Unlike irreversible approaches used to protect therapeutic oligonucleotides, the reversible, glutathione-sensitive modifications disclosed herein are removed from the oligonucleotide when it reaches the reducing environment of the cytosol of the cell. In certain embodiments, removing the glutathione-sensitive moiety at the 2'-carbon leaves a hydroxyl group at the 2'-carbon, which is the natural substituent for a ribonucleotide at that position. As a result, when they reach the cytosol of the cell, the reversibly modified, glutathione-sensitive oligonucleotides can carry out their intended biological activity without any interference from the reversible, glutathione-sensitive moiety, which is removed in the cytosol. The reversible, glutathione-sensitive modifications disclosed in this application represent a powerful new tool for synthetic oligonucleotides that can used in place of or in combination with irreversible modifications to generate stable oligonucleotides having enhanced biological activity within the cytosol of a cell.

Moreover, the glutathione-sensitive nucleoside phosphoramidites disclosed herein are compatible with conventional solid-phase synthesis. Thus, the present reversibly modified, glutathione-sensitive oligonucleotides can be synthesized using conventional phosphoramidite based synthetic methods. Using this synthetic approach, one can select the nucleotide position at which the glutathione-sensitive nucleotides is incorporated into the oligonucleotide. As it is may be desirable to modify specific nucleotide positions in an oligonucleotide, this discovery facilitates the rational design of oligonucleotides having reversible modifications at specific nucleotide positions of interest.

This application also provides glutathione-sensitive nucleotides and nucleosides that can be used as therapeutic agents (e.g., antiviral or anticancer agents).

II. GLUTATHIONE-SENSITIVE OLIGONUCLEOTIDES

One aspect of the present disclosure relates to an oligonucleotide comprising at least one glutathione-sensitive moiety. Typically, the glutathione-sensitive moiety is attached to the sugar moiety of the nucleotide, e.g. a deoxyribose or ribose (or analogs thereof). Typically, the glutathione-sensitive moiety is located at the 2'-carbon of a deoxyribose or ribose (or analogs thereof). In some embodiments, the glutathione-sensitive moiety is located at the 5'-carbon of a ribose or deoxyribose (or analogs thereof), particularly when the modified nucleotide is the 5'-terminal nucleotide of the oligonucleotide. In other embodiments, the glutathione-sensitive moiety is located at the 3'-carbon of a ribose or deoxyribose (or analogs thereof), particularly when the modified nucleotide is the 3'-terminal nucleotide of the oligonucleotide.

In some embodiments, the glutathione-sensitive moiety comprises a sulfonyl group. In other embodiments, the glutathione-sensitive moiety comprises a disulfide bridge.

In certain embodiments, the oligonucleotide comprises at least one nucleotide having a glutathione-sensitive moiety covalently bound to an oxygen atom that is covalently bound to the 2'-carbon of the sugar moiety (e.g., ribose) of the nucleotide. In certain embodiments, the glutathione-sensitive moiety is represented by Formula II, III, or IV. In certain embodiments, the glutathione-sensitive moiety is represented by Formula IIa, IIIa, IIIb, IIIa(i), IIIb(i), IVa, IVb, IVc, IVd, IVe, IVa(i), IVb(i), IVc(i), IVd(i), IVe(i), IVe(ii), IVe(iii), IVe(iv), IVe(v), IVe(vi), IVe(vii), IVe(viii), IVe(ix), IVe(x), or IVe(xi).

1. Formula I

In one embodiment, the glutathione-sensitive oligonucleotide comprises at least one nucleotide represented by Formula I:

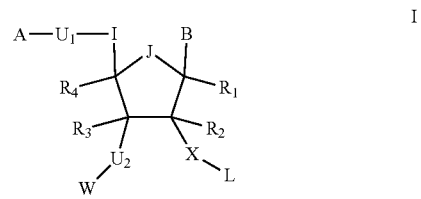

wherein X is O, S, Se or NR', wherein R' is selected from hydrogen, halogen, a substituted or unsubstituted aliphatic, an aryl, a substituted or unsubstituted heteroaryl or a substituted or unsubstituted heterocycle;

wherein $R_1$, $R_2$, $R_3$ and $R_4$ are each independently selected from hydrogen, halogen, OH, $C_1$-$C_6$ alkyl, $C_1$-$C_6$ haloalkyl or wherein two of $R_1$, $R_2$, $R_3$ and $R_4$ are taken together to form a 5-8 membered ring, wherein the ring optionally contains a heteroatom;

wherein J is O, S, NR', CR'R", wherein each of R' and R" is independently selected from hydrogen, halogen, a substituted or unsubstituted aliphatic, aryl or heteroaryl;

wherein B is selected from hydrogen, a natural nucleobase, a modified nucleobase or a universal nucleobase;

wherein $U_2$ is absent or selected from O, S, NR', or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle or a substituted or unsubstituted cycloalkyl;

wherein W is hydrogen, a phosphate group, an internucleotide linking group attaching the at least one nucleotide represented by Formula I to a nucleotide or an oligonucleotide, a halogen, OR', SR', NR'R", a substituted or unsubstituted aliphatic, a substituted or unsubstituted aryl, a substituted or unsubstituted heteroaryl, a substituted or unsubstituted cycloalkyl, a substituted or unsubstituted heterocycle, wherein R' and R" are each independently selected from hydrogen, halogen, a substituted or unsubstituted aliphatic, an aryl, a heteroaryl, a heterocycle or are taken together to form a heterocyclic ring;

wherein I is absent or is selected from O, S, NR', CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl;

wherein $U_1$ is absent, hydrogen, an internucleotide linking group attaching the at least one nucleotide represented by Formula I to a nucleotide or an oligonucleotide, or selected from O, S, NR', or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl and wherein at least one of $U_1$ or W is an internucleotide linking group attaching the at least one nucleotide represented by Formula I to a nucleotide or an oligonucleotide and provided that if U₁ is an internucleotide linking group, A is absent;

wherein I and U₁ can be combined to form CR'—CR" alkyl, CR'—CR" alkenyl, CR'—CR" alkynyl, a substituted or unsubstituted aliphatic, an aryl, a heteroaryl a heterocycle or taken together to form cycloalkyl or heterocyclic ring;

wherein A is absent, a hydrogen, a phosphate group, a phosphate mimic or a phosphoramidate; and wherein L is a glutathione-sensitive moiety selected from Formula II, III, or IV, as described below.

In certain embodiments, X is O.

In certain embodiments, R₁, R₂, R₃ and R₄ are hydrogen.

In certain embodiments, J is O.

In certain embodiments, B is a natural nucleobase.

In certain embodiments, U₂ is absent or O.

In certain embodiments, W is hydrogen, a phosphate group, an internucleotide linking group attaching the at least one nucleotide represented by Formula I to a nucleotide or an oligonucleotide. Typically, W is an internucleotide linking group attaching the at least one nucleotide represented by Formula I to a nucleotide or an oligonucleotide.

In certain embodiments, I is CH₂.

In certain embodiments, U₁ is hydrogen or an internucleotide linking group attaching the at least one nucleotide represented by Formula I to a nucleotide or an oligonucleotide. Typically, U₁ is an internucleotide linking group attaching the at least one nucleotide represented by Formula I to a nucleotide or an oligonucleotide and A is absent.

In certain embodiments, A is absent, a phosphate group or a phosphate mimic. In some embodiments, the phosphate group is a monophosphate, a diphosphate or a triphosphate. In some embodiments, the phosphate mimic is vinylphosphonate, 5'-methylenephosphonate, or a 4'-oxymethylphosphonate.

In certain embodiments, A is hydrogen and U₁ is O.

In certain embodiments, X is O, R₁, R₂, R₃ and R₄ are hydrogen, and J is O. In certain embodiments, X is O; R₁, R₂, R₃ and R₄ are hydrogen; J is O; B is a natural nucleobase; U₂ is absent or O; A is absent; I is CH₂; W is hydrogen, a phosphate group, or an internucleotide linking group attaching the at least one nucleotide represented by Formula I to a nucleotide or an oligonucleotide; and U₁ is hydrogen or an internucleotide linking group attaching the at least one nucleotide represented by Formula I to a nucleotide or an oligonucleotide, wherein at least one of U₁ or W is an internucleotide linking group attaching the at least one nucleotide represented by Formula I to an oligonucleotide.

In certain embodiments, the oligonucleotide containing at least one nucleotide of Formula I has 2-2500 nucleotides. In certain embodiments, the oligonucleotide of Formula I has 500-1500 nucleotides. In certain embodiments, the oligonucleotide containing at least one nucleotide of Formula I has 7-100 nucleotides. In another embodiment, the oligonucleotide containing at least one nucleotide of Formula I has 15-50 nucleotides. In yet another embodiment, the oligonucleotide containing at least one nucleotide of Formula I has 19-25 nucleotides.

In certain embodiments, the oligonucleotide containing at least one nucleotide of Formula I is a nucleic acid inhibitor molecule, as discussed in further detail throughout the application. In other embodiments, the oligonucleotide containing at least one nucleotide of Formula I is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

In certain embodiments, the ring structure of the sugar moiety of at least one nucleotide in the nucleic acid inhibitor molecule is modified and encompasses, for example, Locked Nucleic Acid ("LNA") structures, Bridged Nucleic Acid ("BNA") structures, and Unlocked Nucleic Acid ("UNA") structures, as discussed previously.

a. Glutathione-Sensitive Moiety—Formula II

As discussed above, the glutathione-sensitive oligonucleotides comprise at least one nucleotide represented by Formula I, where the glutathione-sensitive moiety is selected from Formula II, III, or IV. In some embodiments, the glutathione-sensitive moiety is represented by Formula II as follows:

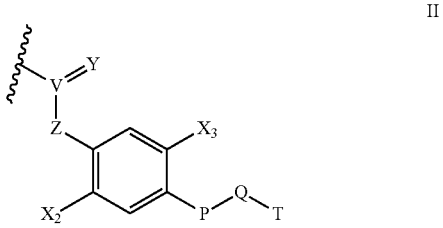

II wherein Y is O, S, Se, or NR', wherein R' is selected from hydrogen, halogen, a substituted or unsubstituted aliphatic, a substituted or unsubstituted aryl, a substituted or unsubstituted heteroaryl, a substituted or unsubstituted heterocycle;

wherein Z is selected from O, S, NR', or CR'R", wherein R' and R" are each independently selected from hydrogen, halogen, CH₃, substituted or unsubstituted aliphatic, substituted or unsubstituted aryl, substituted or unsubstituted heteroaryl, substituted or unsubstituted heterocycle, or R' and R" are taken together to form a heterocyclic ring;

wherein V is C or SO;

wherein X₂ and X₃ are independently selected from hydrogen, halogen, nitro, amino, acyl, substituted or unsubstituted aliphatic, OR₁₀, COR₁₀, CO₂R₁₀, NQ₁Q₂; wherein R₁₀ is independently hydrogen, substituted or unsubstituted aliphatic, hydroxyl or alkoxy substituted aliphatic, arylaliphatic, hydroxyl or an alkoxy substituted aryl or alkoxy substituted heterocyclic;

wherein P and Q are taken together to form a disulfide bridge or a sulfonyl group; and wherein T is a substituted or unsubstituted aliphatic, a substituted or unsubstituted aryl, a substituted or unsubstituted heteroaryl or T is a ligand optionally connected via a spacer to P or Q.

In certain embodiments, said disulfide bridge or said sulfonyl group is cleavable in the cytosol by glutathione at a pH of at least about 7.5.

In some embodiments, Y is O, S or NH. Typically, Y is O.

In some embodiments, Z is O, S or NR'. Typically, Z is NH.

In some embodiments, V is SO. Typically, V is C.

In some embodiments, X₂ and X₃ are independently selected from hydrogen, halogen, nitro, amino or acyl or C₃ to C₆ branched or unbranched alkyl. Typically, X₂ and X₃ are independently selected from hydrogen, halogen, nitro or amino.

Typically, P and Q are taken together to form a disulfide bond.

In some embodiments, T is a $C_3$ to $C_6$ branched or unbranched alkyl or T is a ligand optionally connected via a spacer to P or Q. Typically, T is a $C_4$ branched alkyl.

In certain embodiments, the oligonucleotide having a glutathione-sensitive moiety of Formula II has 2-2500 nucleotides. In certain embodiments, the oligonucleotide having a glutathione-sensitive moiety of Formula II has 500-1500 nucleotides. In certain embodiments, the oligonucleotide having a glutathione-sensitive moiety of Formula II has 7-100 nucleotides. In another embodiment, the oligonucleotide having a glutathione-sensitive moiety of Formula II has 15-50 nucleotides. In yet another embodiment, the oligonucleotide having a glutathione-sensitive moiety of Formula II has 19-25 nucleotides.

In certain embodiments, the oligonucleotide having a glutathione-sensitive moiety of Formula II is a nucleic acid inhibitor molecule, as discussed in further detail throughout the application. In other embodiments, the oligonucleotide having a glutathione-sensitive moiety of Formula II is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

i. Formula IIa

In some embodiments, the glutathione-sensitive moiety is represented by the following Formula:

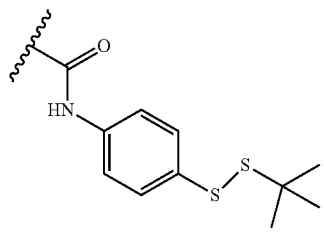

IIa b. Glutathione-Sensitive Moiety—Formula III

In other embodiments of the glutathione-sensitive oligonucleotides comprising at least one nucleotide represented by Formula I, the glutathione-sensitive moiety is represented by Formula III as follows:

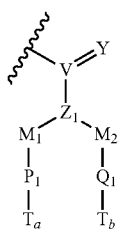

III wherein Y is O, S, Se, or NR', wherein R' is selected from hydrogen, halogen, a substituted or unsubstituted aliphatic, a substituted or unsubstituted aryl, a substituted or unsubstituted heteroaryl, or a substituted or unsubstituted heterocycle;

wherein $Z_1$ is N or CR', wherein R' is selected from hydrogen, halogen, substituted or unsubstituted aliphatic, substituted or unsubstituted aryl, substituted or unsubstituted heteroaryl, substituted or unsubstituted heterocycle;

wherein V is C or SO;

wherein $M_1$ and $M_2$ are each independently selected from substituted or unsubstituted aliphatic, substituted or unsubstituted aromatic, substituted or unsubstituted heteroaryl, substituted or unsubstituted cycloalkyl;

wherein $P_1$ and $Q_1$ are taken together to form a disulfide bridge or a sulfonyl group or wherein $P_1$ and $Q_1$ are each independently a disulfide bridge or a sulfonyl group;

wherein when $P_1$ and $Q_1$ form a disulfide bridge, $M_1$, $M_2$, $P_1$, and $Q_1$ can form a 4-9 membered ring, wherein the ring can be substituted or unsubstituted aromatic, substituted or unsubstituted cycloalkyl, wherein the aromatic or cycloalkyl ring can optionally contain a heteroatom; and wherein $T_a$ and $T_b$ are each independently absent or selected from $CH_3$, substituted or substituted aliphatic, substituted or unsubstituted aryl, substituted or unsubstituted heteroaryl, substituted or unsubstituted heterocycle or a ligand optionally connected via any spacer to $P_1$ or $Q_1$.

In some embodiments, $M_1$, $M_2$, $P_1$, and $Q_1$ are taken together to form a 5-8 membered ring containing alkoxy substituted arylaliphatic, alkoxy substituted heteroaryl or alkoxy substituted heterocyclic.

In some embodiments, Y is O, S or NH. Typically, Y is O.
In some embodiments, $Z_1$ is N or CH. Typically, $Z_1$ is N.
In some embodiments, V is SO. Typically, V is C.
In some embodiments, $M_1$ and $M_2$ are each independently selected from substituted or unsubstituted aliphatic; or $M_1$, $M_2$, $P_1$, and $Q_1$ are taken together to form a 4-9 membered ring, wherein the ring is substituted or unsubstituted cycloalkyl, substituted or unsubstituted heterocycle. Typically, $M_1$ and $M_2$ are substituted or unsubstituted $C_2$ to $C_6$ alkyl or are taken together with $P_1$ and $Q_1$ to form a 5-8 membered ring, wherein the ring is substituted or unsubstituted cycloalkyl.

In some embodiments, $P_1$ and $Q_1$ are taken together to form a disulfide bridge or a sulfonyl group. Typically, $P_1$ and $Q_1$ are taken together to form a disulfide bridge. In some embodiments, the disulfide bridge or the sulfonyl group is cleavable in the cytosol by glutathione at a pH of at least about 7.5.

In some embodiments, $T_a$ and $T_b$ are absent or are each independently absent or selected from $CH_3$, a branched or unbranched $C_3$ to $C_6$ alkyl, substituted or unsubstituted aryl, substituted or unsubstituted heteroaryl, substituted or unsubstituted heterocycle or a ligand optionally connected via any spacer to $P_1$ or $Q_1$. Typically, $T_a$ and $T_b$ are absent, a branched $C_3$ to $C_6$ alkyl, or a ligand connected via any spacer to $P_1$ or $Q_1$.

In some embodiments, the glutathione-sensitive moiety is represented by Formula III, wherein Y is O, S or NH; $Z_1$ is N; V is C; $M_1$ and $M_2$ are each independently selected from substituted or unsubstituted aliphatic, substituted or unsubstituted aromatic, substituted or unsubstituted heteroaryl; or $M_1$, $M_2$, $P_1$, and $Q_1$ are taken together to form a 4-9 membered ring, wherein the ring is substituted or unsubstituted aromatic, substituted or unsubstituted cycloalkyl, substituted or unsubstituted heterocycle or substituted or unsubstituted heteroaryl; $P_1$ and $Q_1$ are taken together to form a disulfide bridge; and $T_a$ and $T_b$ are absent or a ligand optionally connected via any spacer to $P_1$ or $Q_1$.

Typically, the glutathione-sensitive moiety is represented by Formula III, wherein Y is O, S or NH; $Z_1$ is N; V is C;

$M_1$, $M_2$, $P_1$, and $Q_1$ are taken together to form a 5-8 membered ring, wherein the ring is a substituted or unsubstituted aromatic ring or a substituted or unsubstituted cycloalkyl, wherein the aromatic ring or cycloalkyl can optionally contain any heteroatom; $P_1$ and $Q_1$ are taken together to form a disulfide bridge; and $T_a$ and $T_b$ are absent or a ligand optionally connected via any spacer to $P_1$ or $Q_1$.

More typically, the glutathione-sensitive moiety is represented by Formula III, wherein Y is O, S or NH; $Z_1$ is N; V is C; $M_1$, $M_2$, $P_1$, and $Q_1$ are taken together to form a 7 membered ring, wherein the ring is a substituted or unsubstituted cycloalkyl; $P_1$ and $Q_1$ are taken together to form a disulfide bridge; and $T_a$ and $T_b$ are absent.

In some embodiments, the glutathione-sensitive moiety is represented by Formula III, wherein Y is O, S or NH; $Z_1$ is N; V is C; $M_1$ and $M_2$ are each independently selected from substituted or unsubstituted aliphatic, substituted or unsubstituted aromatic, substituted or unsubstituted heteroaryl; $P_1$ and $Q_1$ are each independently a disulfide bridge; and $T_a$ and $T_b$ are selected from $CH_3$, substituted or substituted aliphatic, substituted or unsubstituted aryl, substituted or unsubstituted heteroaryl, substituted or unsubstituted heterocycle or a ligand optionally connected via any spacer to $P_1$ or $Q_1$.

More typically, the glutathione-sensitive moiety is represented by Formula III, wherein Y is O, S or NH; $Z_1$ is N; V is C; $M_1$ and $M_2$ are substituted or unsubstituted aliphatic; $P_1$ and $Q_1$ are each independently a disulfide bridge; and $T_a$ and $T_b$ are each independently selected from $CH_3$, substituted or substituted aliphatic, substituted or unsubstituted aryl, substituted or unsubstituted heteroaryl, substituted or unsubstituted heterocycle or a ligand optionally connected via any spacer to $P_1$ or $Q_1$.

Yet even more typically, the glutathione-sensitive moiety is represented by Formula III, wherein Y is O, S or NH; $Z_1$ is N; V is C; $M_1$ and $M_2$ are substituted or unsubstituted aliphatic; $P_1$ and $Q_1$ are each independently a disulfide bridge; and $T_a$ and $T_b$ are each independently absent or selected from $CH_3$, a branched or unbranched $C_3$ to $C_6$ alkyl, or a ligand optionally connected via any spacer to $P_1$ or $Q_1$.

In certain embodiments, the oligonucleotide having a glutathione-sensitive moiety of Formula III has 2-2500 nucleotides. In certain embodiments, the oligonucleotide having a glutathione-sensitive moiety of Formula III has 500-1500 nucleotides. In certain embodiments, the oligonucleotide having a glutathione-sensitive moiety of Formula III has 7-100 nucleotides. In another embodiment, the oligonucleotide having a glutathione-sensitive moiety of Formula III has 15-50 nucleotides. In yet another embodiment, the oligonucleotide having a glutathione-sensitive moiety of Formula III has 19-25 nucleotides.

In certain embodiments, the oligonucleotide having a glutathione-sensitive moiety of Formula III is a nucleic acid inhibitor molecule, as discussed in further detail throughout the application. In other embodiments, the oligonucleotide having a glutathione-sensitive moiety of Formula III is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

i. Formula IIa

In some embodiments, the glutathione-sensitive moiety is represented by the following Formula:

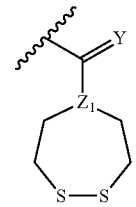

wherein Y is O, S or NH; $Z_1$ is N or CR', wherein R' is selected from hydrogen, halogen, substituted or unsubstituted aliphatic, substituted or unsubstituted aryl, substituted or unsubstituted heteroaryl, substituted or unsubstituted heterocycle.

More typically, the glutathione-sensitive moiety is represented by the following Formula:

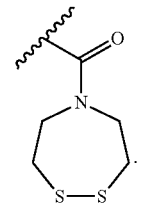

ii. Formula IIIb

In some embodiments, the glutathione-sensitive moiety is represented by the following Formula:

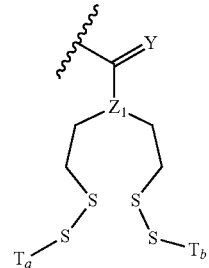

wherein Y is O, S or NH; $Z_1$ is N or CR', wherein R' is selected from hydrogen, halogen, substituted or unsubstituted aliphatic, substituted or unsubstituted aryl, substituted or unsubstituted heteroaryl, substituted or unsubstituted heterocycle; and $T_a$ and $T_b$ are each independently absent or selected from $CH_3$, substituted or substituted aliphatic, substituted or unsubstituted aryl, substituted or unsubstituted heteroaryl, substituted or unsubstituted heterocycle or a ligand optionally connected via any spacer to a sulfur atom.

More typically, the glutathione-sensitive moiety is represented by the following Formula:

IIIb(i)

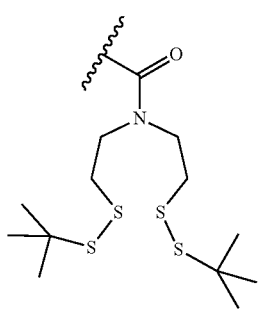

c. Glutathione-Sensitive Moiety—Formula IV

In yet other embodiments of the glutathione-sensitive oligonucleotides comprising at least one nucleotide represented by Formula I, the glutathione-sensitive moiety is represented by Formula IV as follows:

IV

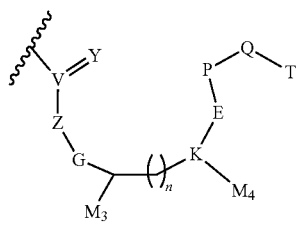

wherein Y is O, S, Se, or NR', wherein R' is selected from hydrogen, halogen, a substituted or unsubstituted aliphatic, a substituted or unsubstituted aryl, a substituted or unsubstituted heteroaryl, a substituted or unsubstituted heterocycle wherein Z is selected from O, S, NR', or CR'R", wherein R' and R" are each independently selected from hydrogen, halogen, $CH_3$, substituted or unsubstituted aliphatic, substituted or unsubstituted aryl, substituted or unsubstituted heteroaryl, substituted or unsubstituted heterocycle, or R' and R" are taken together to form a heterocyclic ring;

wherein V is C or SO;

wherein G and E can be each independently absent, or selected from $CH_2$, CHR', CR'R", NH, or NR', wherein R' and R" are each independently selected from hydrogen, halogen, a substituted or unsubstituted aliphatic, a substituted or unsubstituted aryl, a substituted or unsubstituted heteroaryl, a substituted or unsubstituted heterocycle or R' and R" are taken together to form a heterocyclic ring;

wherein $M_3$ and $M_4$ can be taken to form a 4-9 membered ring, wherein the ring can be substituted or unsubstituted aromatic, substituted or unsubstituted cycloalkyl, wherein the aromatic or cycloalkyl ring can optionally contain a heteroatom, or $M_3$ and $M_4$ are each independently selected from hydrogen, substituted or unsubstituted aliphatic, substituted or unsubstituted aromatic, substituted or unsubstituted heteroaryl, substituted or unsubstituted cycloalkyl or COOR, wherein R is selected from hydrogen, $CH_3$, or substituted or unsubstituted aliphatic;

wherein K is C, CH, or a substituted or unsubstituted aliphatic;

wherein n is 0-5;

wherein P and Q are taken together to form a disulfide bridge or a sulfonyl group; and wherein T is substituted or unsubstituted aliphatic, substituted or unsubstituted aryl, substituted or unsubstituted heteroaryl or T can be a ligand optionally connected via any spacer to P or Q.

In some embodiments, Y is O, S or NH. Typically, Y is O.

In some embodiments, Z is O, S, NH, NR', or CR'R", wherein R' and R" are each independently selected from hydrogen, $CH_3$, or substituted or unsubstituted aliphatic. In certain embodiments, Z is NH or N—$CH_3$ In some embodiments, V is SO. Typically, V is C.

In some embodiments, $M_3$ and $M_4$ are each independently selected from hydrogen or substituted or unsubstituted aliphatic, such as a $C_2$ to $C_6$ alkyl; or $M_3$ and $M_4$ are taken together to form a 4-9 membered ring, wherein the ring is substituted or unsubstituted cycloalkyl or substituted or unsubstituted heterocycle. Typically, $M_3$ and $M_4$ are independently substituted or unsubstituted $C_2$ to $C_6$ alkyl or taken together to form a 5-8 membered ring, wherein the ring is substituted or unsubstituted cycloalkyl.

In some embodiments, G is absent, $CH_2$, or CHR', wherein R' is substituted or unsubstituted aliphatic. Typically, G is absent or $CH_2$.

In some embodiments, E is absent, NH, NR', $CH_2$, or CHR', wherein R' is substituted or unsubstituted aliphatic. Typically, E is absent, NH, or $CH_2$.

In some embodiments, G and E are absent.

In some embodiments, K is C, or CH. Typically, K is CH.

In some embodiments, n is 0.

In some embodiments, P and Q are taken together to form a disulfide bridge or a sulfonyl group. Typically, P and Q are taken together to form a disulfide bridge. In some embodiments, the disulfide bridge or the sulfonyl group is cleavable in the cytosol by glutathione at a pH of at least about 7.5.

In some embodiments, T is a substituted or unsubstituted $C_2$-$C_6$ alkyl, substituted or unsubstituted aryl, substituted or unsubstituted heteroaryl or T is a ligand optionally connected to P or Q via any spacer. Typically, T is a substituted or unsubstituted $C_2$-$C_6$ alkyl or a ligand optionally connected to P or Q via any spacer.

In some embodiments, the glutathione-sensitive moiety is represented by Formula IV, wherein Y is O, S, NH; wherein Z is O, S NH, or $NCH_3$; V is C; G is $CH_2$ and E is absent or G is absent and E is $CH_2$; $M_3$ and $M_4$ are taken together to form a 5-8 membered ring, wherein the ring is a cycloalkyl substituted with a heteroatom or an unsubstituted cycloalkyl or $M_3$ and $M_4$ are each independently a substituted or unsubstituted $C_2$ to $C_6$ alkyl; K is CH; n is 0; P and Q are taken together to form a disulfide bridge; T is $CH_3$, substituted or unsubstituted $C_2$ to $C_6$ alkyl, substituted or unsubstituted aryl, substituted or unsubstituted heteroaryl or T is a ligand optionally connected via any spacer to P or Q.

In certain embodiments, the oligonucleotide having a glutathione-sensitive moiety of Formula IV has 2-2500 nucleotides. In certain embodiments, the oligonucleotide having a glutathione-sensitive moiety of Formula IV has 500-1500 nucleotides. In certain embodiments, the oligonucleotide having a glutathione-sensitive moiety of Formula IV has 7-100 nucleotides. In another embodiment, the oligonucleotide having a glutathione-sensitive moiety of Formula IV has 15-50 nucleotides. In yet another embodiment, the oligonucleotide having a glutathione-sensitive moiety of Formula IV has 19-25 nucleotides.

In certain embodiments, the oligonucleotide having a glutathione-sensitive moiety of Formula IV is a nucleic acid inhibitor molecule, as discussed in further detail throughout the application. In other embodiments, the oligonucleotide having a glutathione-sensitive moiety of Formula IV is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

i. Formula IVa

In some embodiments, the glutathione-sensitive moiety may be represented by the following Formula:

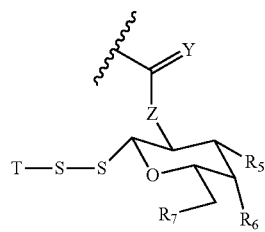

IVa wherein Y is O, S, NH; wherein Z is O, S or NH, wherein $R_5$, $R_6$, and $R_7$ are each independently selected from OAcyl, NHR', NR', or CR'R", wherein R' and R" are each independently selected from hydrogen, halogen, substituted aliphatic or unsubstituted aliphatic, aryl, heteroaryl, heterocyclic, or can be taken together to form a heterocyclic ring; and;

wherein T is a branched or unbranched $C_2$-$C_6$ alkyl or a ligand optionally connected via any spacer to a sulfur atom.

For example, the glutathione-sensitive moiety may be represented by the following Formula:

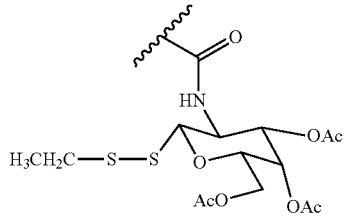

IVa(i)

ii. Formula IVb

In some embodiments, the glutathione-sensitive moiety may be represented by the following Formula:

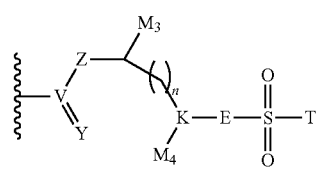

IVb wherein Y is O, S, NH; Z is O, S or NH; V is C; $M_3$ and $M_4$ are hydrogen; K is CH or a substituted or unsubstituted aliphatic; E is NH or NR', wherein R' is substituted or unsubstituted aliphatic; n is 0-5; T is substituted or unsubstituted $C_2$ to $C_6$ alkyl, substituted or unsubstituted aryl, substituted or unsubstituted heteroaryl or T is a ligand optionally connected via any spacer.

In some embodiments, the glutathione-sensitive moiety is represented by Formula IVb, wherein Y is O, Z is NH; V is C; $M_3$ and $M_4$ are hydrogen; K is CH; E is NH; n is 1; P and Q are taken together to form a sulfonyl group; and T is substituted aryl.

For example, the glutathione-sensitive moiety may be represented by the following Formula:

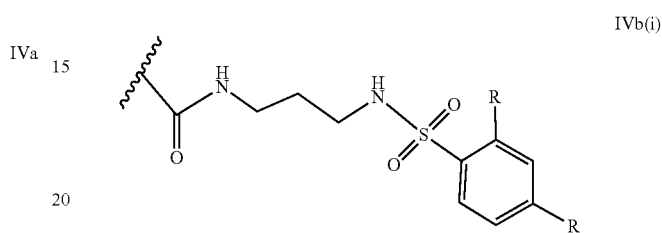

IVb(i)

wherein R is selected from hydrogen, $CH_3$, $NO_2$, substituted or unsubstituted aliphatic, aryl, heteroaryl, cycloalkyl or a heterocycle or R is a targeting ligand optionally connected via any spacer.

In some embodiments, the glutathione-sensitive moiety is represented by Formula IVb, wherein Y is O, Z is NH; V is C; $M_3$ and $M_4$ are hydrogen; K is CH; E is NH; n is 0; P and Q are taken together to form a sulfonyl group; and T is substituted aryl.

For example, the glutathione-sensitive moiety may be represented by the following Formula:

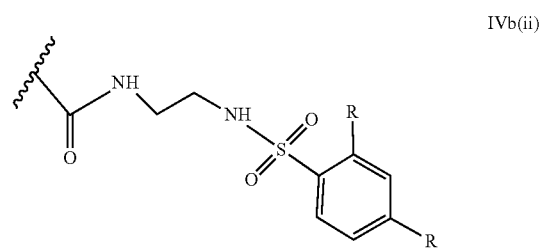

IVb(ii)

wherein R is selected from hydrogen, $CH_3$, $NO_2$, substituted or unsubstituted aliphatic, aryl, heteroaryl, cycloalkyl or a heterocycle or R is a targeting ligand optionally connected via any spacer. In certain embodiments, R is hydrogen.

iii. Formula IVc

In some embodiments, the glutathione-sensitive moiety is represented by Formula IV, wherein Y is O, S, NH; Z is selected from O, S, or NR', wherein R' is selected from hydrogen, halogen, $CH_3$, substituted or unsubstituted aliphatic, substituted or unsubstituted aryl, substituted or unsubstituted heteroaryl, substituted or unsubstituted heterocycle; G and E are absent; V is C; $M_3$ and $M_4$ are taken together to form a 5-8 membered ring, wherein the ring is a substituted or unsubstituted cycloalkyl, optionally substituted with a heteroatom; K is CH; n is 0-5; P and Q are taken together to form a disulfide bridge; T is substituted or unsubstituted $C_2$ to $C_6$ alkyl, substituted or unsubstituted aryl, substituted or unsubstituted heteroaryl or T is a ligand optionally connected via any spacer. Typically, Y is O and Z is NH or $NCH_3$.

In some embodiments, the glutathione-sensitive moiety is represented by the following Formula:

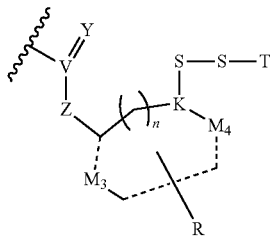

IVc wherein Y is O, S, NH; Z is selected from O, S, or NR', wherein R' is selected from hydrogen, halogen, CH$_3$, substituted or unsubstituted aliphatic, substituted or unsubstituted aryl, substituted or unsubstituted heteroaryl, substituted or unsubstituted heterocycle; V is C; M$_3$ and M$_4$ are taken together to form a 5-8 membered ring, wherein the ring is a substituted or unsubstituted cycloalkyl, optionally substituted with a heteroatom; K is a branched or unbranched substituted or unsubstituted C$_2$ to C$_6$ alkyl; n is 0 or 1; T is substituted or unsubstituted C$_2$ to C$_6$ alkyl, substituted or unsubstituted aryl, substituted or unsubstituted heteroaryl or T is a ligand optionally connected via any spacer; wherein R is selected from hydrogen, CH$_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via any spacer. Typically, Y is O and Z is NH or NCH$_3$.

For example, the glutathione-sensitive moiety may be represented by the following Formula:

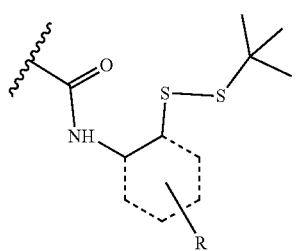

IVc(i)

wherein R is selected from hydrogen, CH$_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via any spacer.

iv. Formula IVd

In some embodiments, the glutathione-sensitive moiety is represented by Formula IV, wherein Y is O, S, NH; wherein Z is selected from O, S, or NR', wherein R' is selected from hydrogen, halogen, CH$_3$, substituted or unsubstituted aliphatic, substituted or unsubstituted aryl, substituted or unsubstituted heteroaryl, substituted or unsubstituted heterocycle; V is C; G and E are absent; M$_3$ is COOR, wherein R is selected from hydrogen, CH$_3$ or a substituted or unsubstituted C$_2$ to C$_6$ alkyl; M$_4$ is hydrogen; K is CH; n is 0; P and Q are taken together to form a disulfide bridge; T is substituted or unsubstituted C$_2$ to C$_6$ alkyl, substituted or unsubstituted aryl, substituted or unsubstituted heteroaryl or T is a ligand optionally connected via any spacer to P or Q. Typically, Y is O and Z is NH or NCH$_3$.

In one embodiment, the glutathione-sensitive moiety is represented by the following Formula:

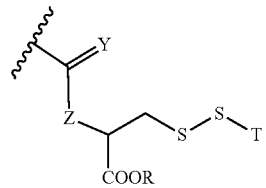

IVd wherein Y is O, S, NH; Z is O, S, NH, or NCH$_3$; T is substituted or unsubstituted C$_2$ to C$_6$ alkyl, substituted or unsubstituted aryl, substituted or unsubstituted heteroaryl or T is a ligand optionally connected via any spacer; and R is selected from hydrogen, CH$_3$ or a substituted or unsubstituted C$_2$ to C$_6$ alkyl.

For example, the glutathione-sensitive moiety may be represented by the following Formula:

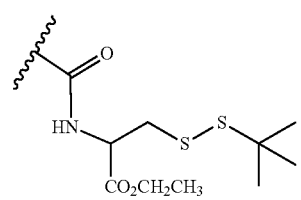

IVd(i)

v. Formula IVe

In some embodiments, the glutathione-sensitive moiety is represented by Formula IV, wherein Y is O, S, NH; Z is selected from O, S, or NR', wherein R' is selected from hydrogen, halogen, CH$_3$, substituted or unsubstituted aliphatic, substituted or unsubstituted aryl, substituted or unsubstituted heteroaryl, substituted or unsubstituted heterocycle; V is C or SO; n is 0; M$_3$ and M$_4$ are taken together to form a 4-9 membered ring, wherein the ring is a substituted or unsubstituted aryl; K is C, CH, N, NH, or a branched or unbranched substituted or unsubstituted C$_2$ to C$_6$ alkyl; T is substituted or unsubstituted C$_2$ to C$_6$ alkyl, substituted or unsubstituted aryl, substituted or unsubstituted heteroaryl or T is a ligand optionally connected via any spacer. Typically, Y is O and Z is NH or NCH$_3$.

In some embodiments, the glutathione-sensitive moiety is represented by the following Formula:

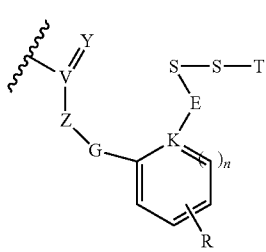

IVe wherein Y is O, S, NH; Z is selected from O, S, or NR', wherein R' is selected from hydrogen, halogen, CH₃, substituted or unsubstituted aliphatic, substituted or unsubstituted aryl, substituted or unsubstituted heteroaryl, substituted or unsubstituted heterocycle; V is C or SO; G and E can be each independently absent, or selected from CH₂, CHR', CR'R", NH, NR', wherein R' and R" are each independently selected from hydrogen, halogen, a substituted or unsubstituted aliphatic, a substituted or unsubstituted aryl, a substituted or unsubstituted heteroaryl, a substituted or unsubstituted heterocycle or R' and R" are taken together to form a heterocyclic ring; K is C or CH; n is 0-5; T is substituted or unsubstituted $C_2$ to $C_6$ alkyl, substituted or unsubstituted aryl, substituted or unsubstituted heteroaryl or T is a ligand optionally connected via any spacer; and wherein R is selected from hydrogen, CH₃, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via any spacer.

In certain embodiments, Z is NR', wherein R' is hydrogen, CH₃, or substituted or unsubstituted aliphatic. Typically, Z is NH or NCH₃. In certain embodiments, Z is S.

In certain embodiments, Y is O, S, or NH and V is C. In one embodiment, V is SO and Y is O.

In certain embodiments, one or both of G and E are absent, CH₂, or CR'R", wherein R' and R" are independently selected from hydrogen or substituted or unsubstituted aliphatic. In certain embodiments, G and E are both absent or G is CH₂ and E is absent or G is absent and E is CH₂ or branched alkyl.

For example, the glutathione-sensitive moiety may be represented by one of the following Formulas:

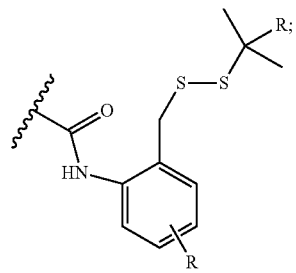

IVe(i)

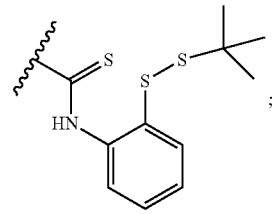

IVe(ii)

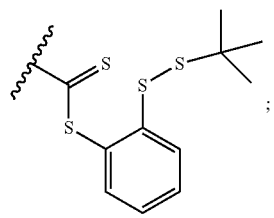

IVe(iii)

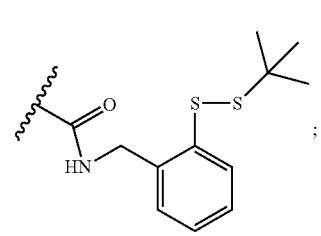

IVe(iv)

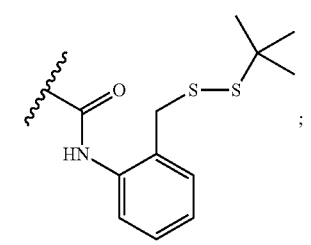

IVe(v)

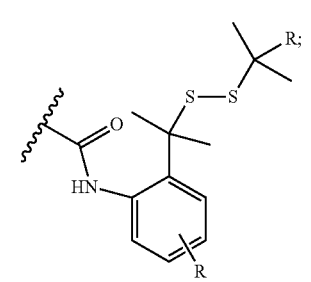

IVe(vi)

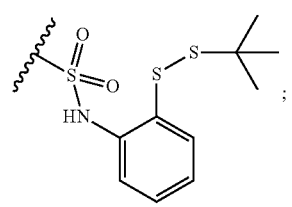

IVe(vii)

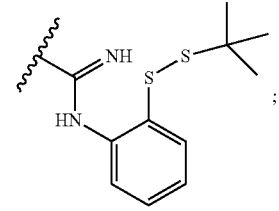

IVe(viii)

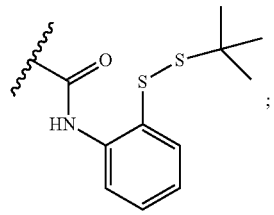

IVe(ix)

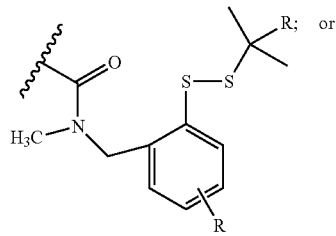

IVe(x)

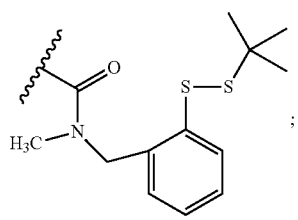

IVe(xi)

wherein R is selected from hydrogen, CH$_3$, substituted or unsubstituted aliphatic, substituted or unsubstituted aryl, substituted or unsubstituted heteroaryl, substituted or unsubstituted cycloalkyl or a substituted or unsubstituted heterocycle or R is a targeting ligand optionally connected via any spacer.

2. Formula V (Oligonucleotide with Formula II Glutathione-Sensitive Moiety)

In other embodiments, the glutathione-sensitive oligonucleotide comprises at least one nucleotide represented by Formula V as follows:

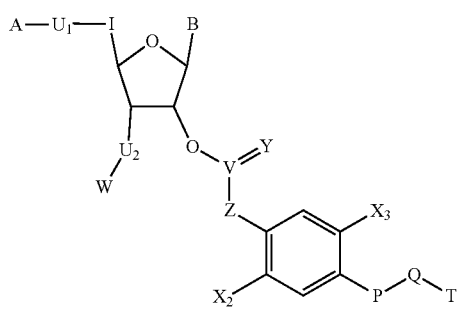

V wherein A, U$_1$, I, B, W, and U$_2$ are as described in Formula I; and wherein Y, V, Z, X$_2$, X$_3$, P, Q and T are as described in Formula II.

In certain embodiments, U$_1$ is absent, an oxygen, or an internucleotide linking group attaching the at least one nucleotide represented by Formula V to a nucleotide or an oligonucleotide, or hydrogen; U$_2$ is absent or O; and W is hydrogen, a phosphate group, or an internucleotide linking group attaching the at least one nucleotide represented by Formula V to a nucleotide or an oligonucleotide, provided that at least one of U$_1$ or W is an internucleotide linking group attaching the at least one nucleotide represented by Formula V to a nucleotide or an oligonucleotide and provided that if U$_1$ is an internucleotide linking group, A is absent.

In certain embodiments, I is CH$_2$. In certain embodiments, B is a natural nucleobase. In certain embodiments, I is CH$_2$ and B is a natural nucleobase.

In certain embodiments, A is hydrogen, a phosphate group or a phosphate mimic. In certain embodiments, A is hydrogen and U$_1$ is oxygen. In certain embodiments, A is hydrogen, U$_1$ is oxygen, and I is CH$_2$.

a. Formula Va

In some embodiments, the glutathione-sensitive oligonucleotide comprises at least one nucleotide represented by the following Formula:

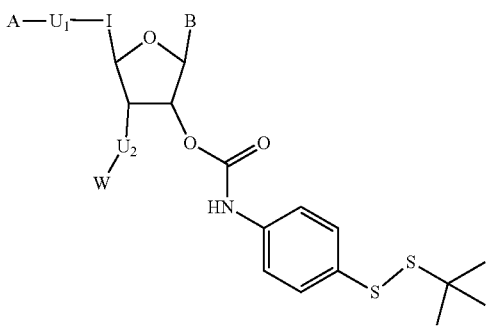

Va wherein A, U$_1$, U$_2$, I, W, and B are as described above for Formula V.

In certain embodiments, the oligonucleotide containing at least one nucleotide of Formula V has 2-2500 nucleotides. In certain embodiments, the oligonucleotide containing at least one nucleotide of Formula V has 500-1500 nucleotides. In certain embodiments, the oligonucleotide containing at least one nucleotide of Formula V has 7-100 nucleotides. In another embodiment, the oligonucleotide containing at least one nucleotide of Formula V has 15-50 nucleotides. In yet another embodiment, the oligonucleotide containing at least one nucleotide of Formula V has 19-25 nucleotides.

In certain embodiments, the oligonucleotide containing at least one nucleotide of Formula V is a nucleic acid inhibitor molecule, as discussed in further detail throughout the application. In other embodiments, the oligonucleotide containing at least one nucleotide of Formula V is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

3. Formula VI (Oligonucleotide with Formula III Glutathione-Sensitive Moiety)

In some embodiments, the glutathione-sensitive oligonucleotide comprises at least one nucleotide represented by Formula VI as follows:

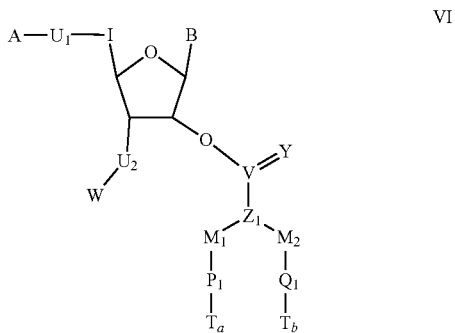

VI wherein A, U$_1$, I, B, W, and U$_2$ are as described in Formula I; and wherein Y, V, Z$_1$, M$_1$, M$_2$, P$_1$, Q$_1$, T$_a$ and T$_b$ are as described in Formula III.

In certain embodiments, U$_1$ is absent, an oxygen, or an internucleotide linking group attaching the at least one nucleotide represented by Formula VI to a nucleotide or an oligonucleotide, or hydrogen; U$_2$ is absent or O; and W is hydrogen, a phosphate group, or an internucleotide linking group attaching the at least one nucleotide represented by Formula VI to a nucleotide or an oligonucleotide, provided that at least one of $U_1$ or W is an internucleotide linking group attaching the at least one nucleotide represented by Formula VI to a nucleotide or an oligonucleotide and provided that if $U_1$ is an internucleotide linking group, A is absent.

In certain embodiments, I is $CH_2$. In certain embodiments, B is a natural nucleobase. In certain embodiments, I is $CH_2$ and B is a natural nucleobase.

In certain embodiments, A is hydrogen, a phosphate group or a phosphate mimic. In certain embodiments, A is hydrogen and $U_1$ is oxygen. In certain embodiments, A is hydrogen, $U_1$ is oxygen, and I is $CH_2$.

In certain embodiments, the oligonucleotide containing at least one nucleotide of Formula VI has 2-2500 nucleotides. In certain embodiments, the oligonucleotide containing at least one nucleotide of Formula VI has 500-1500 nucleotides. In certain embodiments, the oligonucleotide containing at least one nucleotide of Formula VI has 7-100 nucleotides. In another embodiment, the oligonucleotide containing at least one nucleotide of Formula VI has 15-50 nucleotides. In yet another embodiment, the oligonucleotide containing at least one nucleotide of Formula VI has 19-25 nucleotides.

In certain embodiments, the oligonucleotide containing at least one nucleotide of Formula VI is a nucleic acid inhibitor molecule, as discussed in further detail throughout the application. In other embodiments, the oligonucleotide containing at least one nucleotide of Formula VI is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

a. Formula VIa

In some embodiments, the glutathione-sensitive oligonucleotide comprises at least one nucleotide represented by the following Formula:

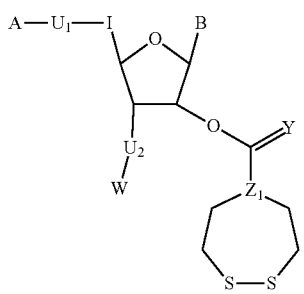

VIa wherein A, $U_1$, $U_2$, W, I and B are as described above for Formula VI and Y and $Z_1$ are as described above for Formula IIIa.

More typically, the present glutathione-sensitive oligonucleotide comprises at least one nucleotide represented by the following Formula:

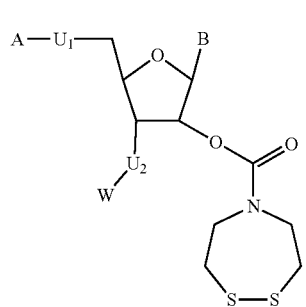

VIa(i)

wherein A, $U_1$, $U_2$, W, and B are as described above for Formula VI.

b. Formula VIb

In some embodiments, the present glutathione-sensitive oligonucleotide comprises at least one nucleotide represented by the following Formula:

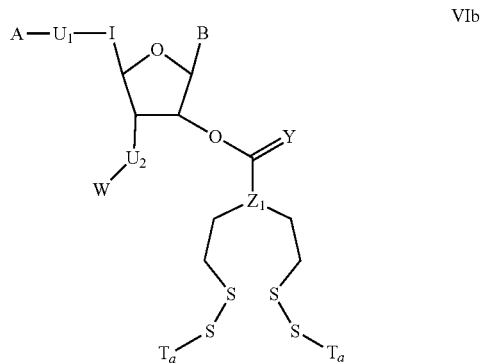

VIb wherein A, $U_1$, $U_2$, W, I, and B are as described above for Formula VI, and wherein Y, $Z_1$ and $T_a$ and $T_b$ are as described above for Formula IIIb.

More typically, the present glutathione-sensitive oligonucleotide comprises at least one nucleotide represented by the following Formula:

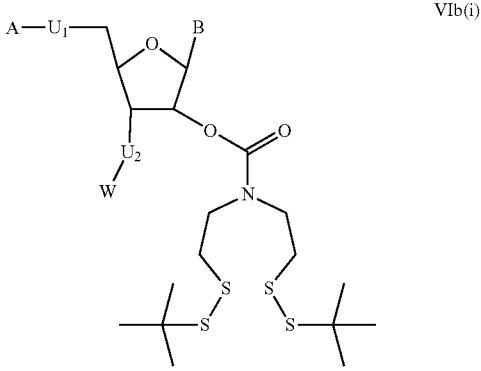

VIb(i)

wherein A, $U_1$, $U_2$, W, and B are as described above for Formula VI.

4. Formula VII (Oligonucleotide with Formula IV Glutathione-Sensitive Moiety)

In some embodiments, the present glutathione-sensitive oligonucleotide comprises at least one nucleotide represented by Formula VII as follows:

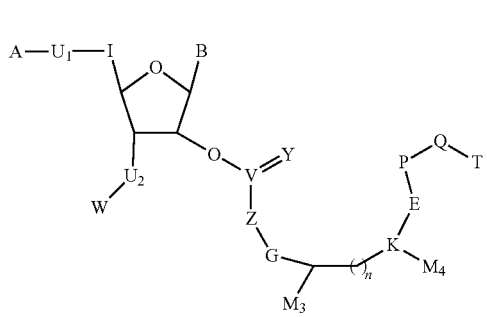

VII

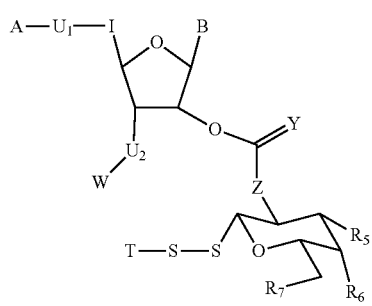

VIIa wherein A, $U_1$, I, B, W, and $U_2$ are as described in Formula I; and wherein Y, Z, V, K, G, E, n, $M_3$, $M_4$, P, Q, and T are as described above in Formula IV.

In certain embodiments, $U_1$ is absent, an oxygen, or an internucleotide linking group attaching the at least one nucleotide represented by Formula VII to a nucleotide or an oligonucleotide, or hydrogen; $U_2$ is absent or O; and W is hydrogen, a phosphate group, or an internucleotide linking group attaching the at least one nucleotide represented by Formula VII to a nucleotide or an oligonucleotide, provided that at least one of $U_1$ or W is an internucleotide linking group attaching the at least one nucleotide represented by Formula VII to a nucleotide or an oligonucleotide and provided that if $U_1$ is an internucleotide linking group, A is absent.

In certain embodiments, I is $CH_2$. In certain embodiments, B is a natural nucleobase. In certain embodiments, I is $CH_2$ and B is a natural nucleobase.

In certain embodiments, A is hydrogen, a phosphate group or a phosphate mimic. In certain embodiments, A is hydrogen and $U_1$ is oxygen. In certain embodiments, A is hydrogen, $U_1$ is oxygen, and I is $CH_2$.

In certain embodiments, the oligonucleotide containing at least one nucleotide of Formula VII has 2-2500 nucleotides. In certain embodiments, the oligonucleotide containing at least one nucleotide of Formula VII has 500-1500 nucleotides. In certain embodiments, the oligonucleotide containing at least one nucleotide of Formula VII has 7-100 nucleotides. In another embodiment, the oligonucleotide containing at least one nucleotide of Formula VII has 15-50 nucleotides. In yet another embodiment, the oligonucleotide containing at least one nucleotide of Formula VII has 19-25 nucleotides.

In certain embodiments, the oligonucleotide containing at least one nucleotide of Formula VII is a nucleic acid inhibitor molecule, as discussed in further detail throughout the application. In other embodiments, the oligonucleotide containing at least one nucleotide of Formula VII is a CRISPR nucleic acid, a nucleic acid for gene therapy, a nucleic acid for DNA editing, a probe, or any other oligonucleotide that is susceptible to degradation by nucleases and/or harsh environmental conditions (e.g., pH), including other oligonucleotides that are to be administered in vivo.

a. Formula VIIa

In some embodiments, the glutathione-sensitive modified oligonucleotide comprises at least one nucleotide represented by the following Formula:

wherein A, $U_1$, $U_2$, W, I and B are as described above for Formula VII; and wherein Y, Z, $R_5$, $R_6$, and $R_7$, and T are as described above in Formula IVa. In certain embodiments, B is a natural nucleobase.

More typically, the present glutathione-sensitive oligonucleotide comprises at least one nucleotide represented by the following Formula:

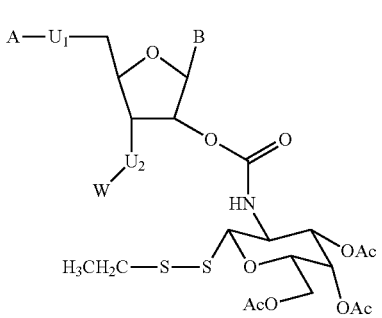

VIIa(i)

wherein A, $U_1$, $U_2$, W, and B are as described above for Formula VII.

b. Formula VIIb

In some embodiments, the present glutathione-sensitive oligonucleotide comprises at least one nucleotide represented by the following Formula:

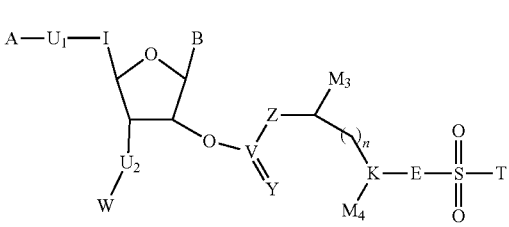

VIIb wherein A, $U_1$, $U_2$, W, I, and B are as described above for Formula VII; and wherein Y, V, Z, K, E, $M_3$, $M_4$, n and T are as described above for Formula IVb. In certain embodiments, B is a natural nucleobase.

In some embodiments, the present glutathione-sensitive oligonucleotide comprises at least one nucleotide represented by the following Formula:

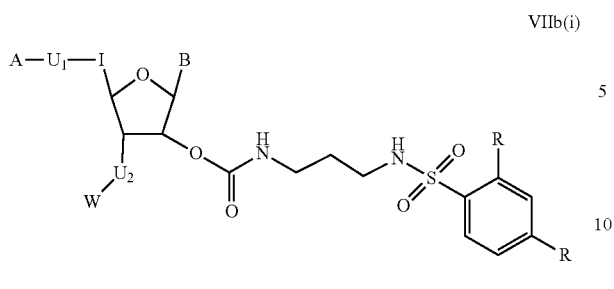

VIIb(i)

wherein A, $U_1$, $U_2$, W, and B are as described above for Formula VII; and wherein R is as described in Formula IVb(i).

In some embodiments, the present glutathione-sensitive oligonucleotide comprises at least one nucleotide represented by the following Formula:

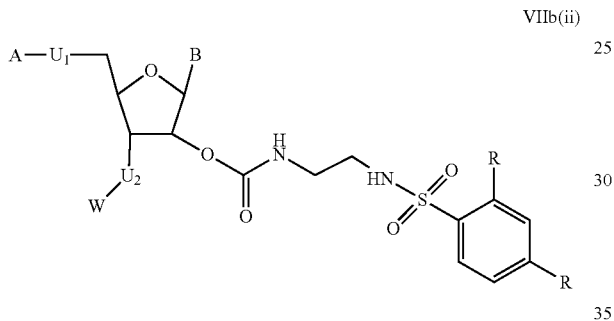

VIIb(ii)

wherein A, $U_1$, $U_2$, W, and B are as described above for Formula VII; and wherein R is as described in Formula IVb(ii).

c. Formula VIIc

In some embodiments, the present glutathione-sensitive oligonucleotide comprises at least one nucleotide represented by the following Formula:

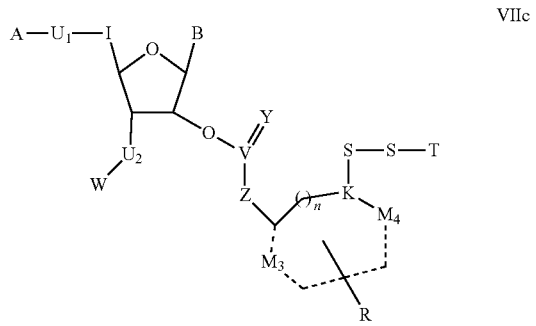

VIIc wherein A, $U_1$, $U_2$, W, I and B are as described above for Formula VII; and wherein Y, Z, V, K, n, T, and R are as described above for Formula IVc. In certain embodiments, B is a natural nucleobase.

More typically, the present glutathione-sensitive oligonucleotide comprises at least one nucleotide represented by the following Formula:

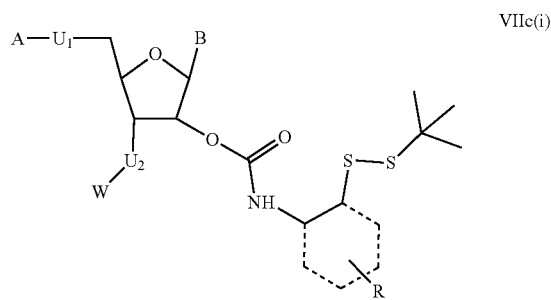

VIIc(i)

wherein A, $U_1$, $U_2$, W and B are as described above for Formula VII; and wherein R is as described in Formula IVc(i).

d. Formula VIId

In some embodiments, the present glutathione-sensitive oligonucleotide comprises at least one nucleotide represented by the following Formula:

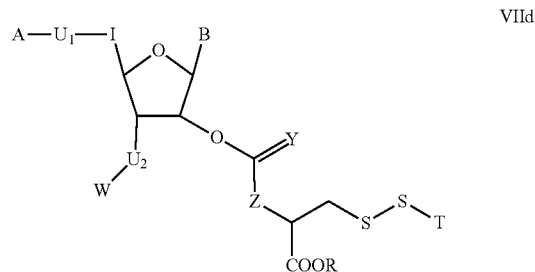

VIId wherein A, $U_1$, $U_2$, W, I, and B are as described above for Formula VII; and wherein Y, Z, R and T are as described above for Formula IVd. In certain embodiments, B is a natural nucleobase.

More typically, the present glutathione-sensitive oligonucleotide comprises at least one nucleotide represented by the following Formula:

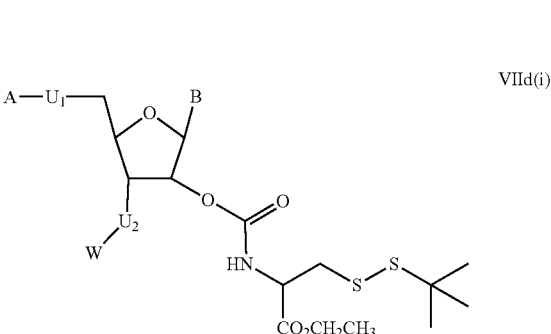

VIId(i)

wherein A, $U_1$, $U_2$, W, and B are as described above for Formula VII.

e. Formula VIIe

In some embodiments, the present glutathione-sensitive oligonucleotide comprises at least one nucleotide represented by the following Formula:

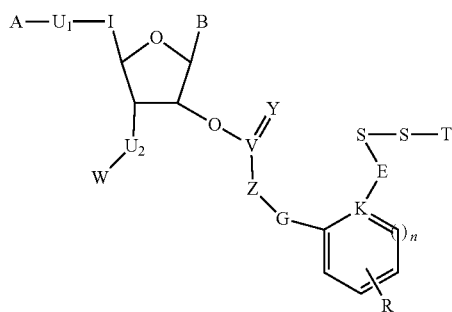

VIIe

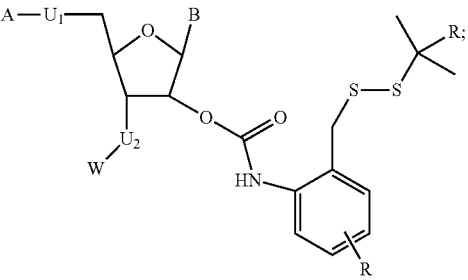

VIIe(iv)

wherein A, U$_1$, U$_2$, W, I, and B are as described above for Formula VII and wherein V, Y, Z, G, E, T, K, n, R, and T are as described above for Formula IVe. In certain embodiments, B is a natural nucleobase.

More typically, the present glutathione-sensitive oligonucleotide comprises at least one nucleotide selected from one of the following Formula:

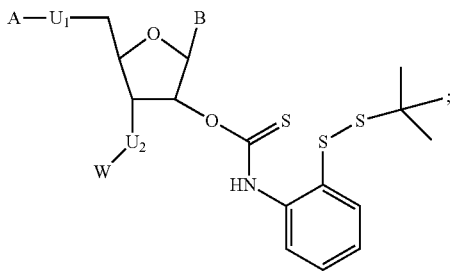

VIIe(v)

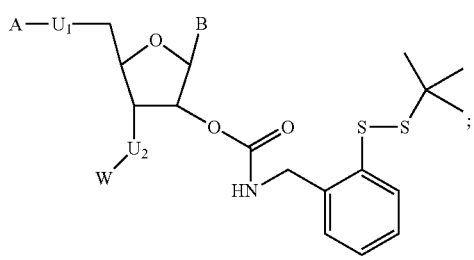

VIIe(i)

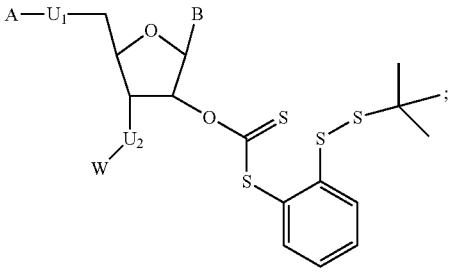

VIIe(vi)

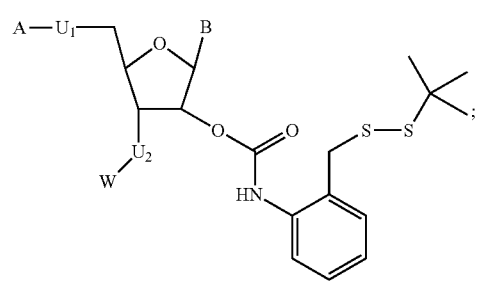

VIIe(ii)

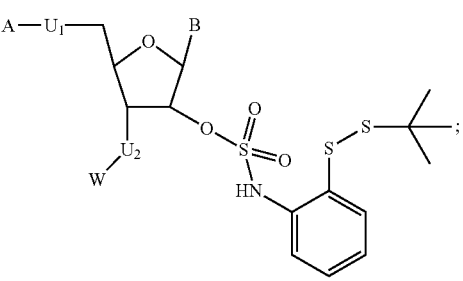

VIIe(vii)

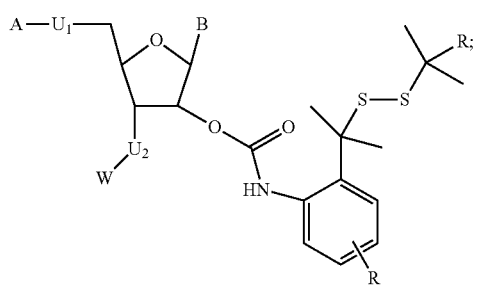

VIIe(iii)

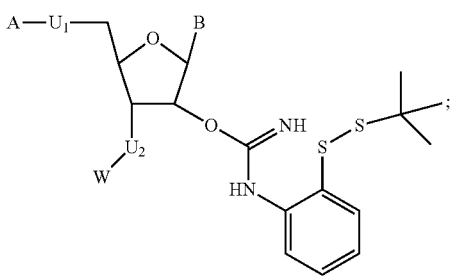

VIIe(viii)

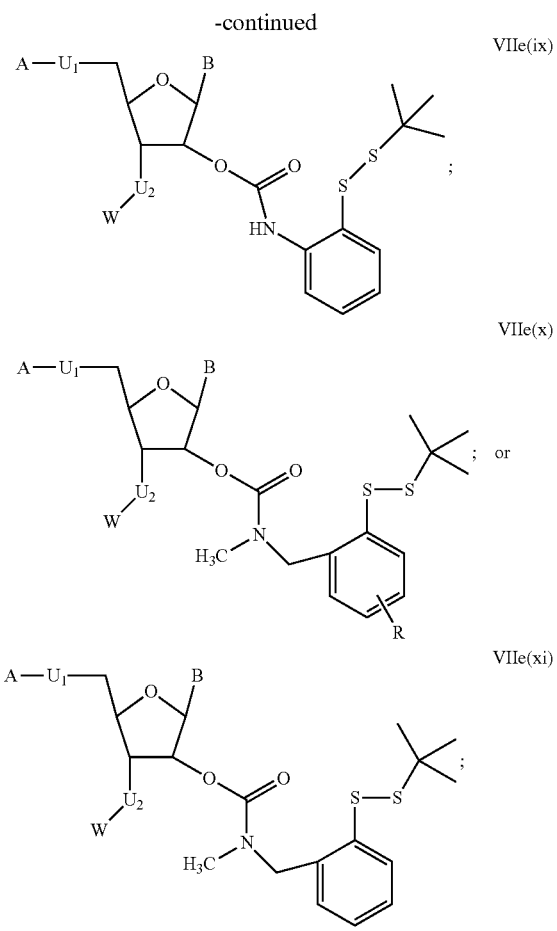

wherein A, $U_1$, $U_2$, W, and B are as described above for Formula VII; and wherein R is selected from hydrogen, $CH_3$, substituted or substituted aliphatic, aryl, heteroaryl, cycloalkyl or a heterocycle or R is a targeting ligand optionally connected via any spacer.

A. Glutathione-Sensitive Nucleic Acid Inhibitor Molecules

In certain embodiments, the glutathione-sensitive moiety is incorporated into a nucleic acid inhibitor molecule. Various oligonucleotide structures have been used as nucleic acid inhibitor molecules, including single stranded and double stranded oligonucleotides, and any of these various oligonucleotides can be modified to include one or more glutathione-sensitive nucleotides as described herein.

In certain embodiments, the nucleic acid inhibitor molecule is a double-stranded RNAi inhibitor molecule comprising a sense (or passenger) strand and an antisense (or guide strand). A variety of double stranded RNAi inhibitor molecule structures are known in the art. For example, early work on RNAi inhibitor molecules focused on double-stranded nucleic acid molecules with each strand having sizes of 19-25 nucleotides with at least one 3'-overhang of 1 to 5 nucleotides (see, e.g., U.S. Pat. No. 8,372,968). Subsequently, longer double-stranded RNAi inhibitor molecules that get processed in vivo by the Dicer enzyme to active RNAi inhibitor molecules were developed (see, e.g., U.S. Pat. No. 8,883,996). Later work developed extended double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, WO 2010/033225, and WO 2016/100401, which are incorporated by reference for their disclosure of these double-stranded nucleic acid inhibitor molecules). Those structures include single-stranded extensions (on one or both sides of the molecule) and double-stranded extensions.

In some embodiments of the dsRNAi inhibitor molecule, the sense and antisense strands range from 15-66, 25-40, or 19-25 nucleotides. In some embodiments, the sense strand is between 18 and 66 nucleotides in length. In certain embodiments, the sense strand is between 18 and 25 nucleotides in length. In certain embodiments, the sense strand is 18, 19, 20, 21, 22, 23, or 24 nucleotides in length. In certain of those embodiments, the sense strand is between 25 and 45 nucleotides in length. In certain embodiments, the sense strand is between 30 and 40 nucleotides in length. In certain embodiments, the sense strand is 36, 37, 38, 39, or 40 nucleotides in length. In certain embodiments, the sense strand is between 25 and 30 nucleotides in length. In certain of those embodiments, the sense strand is 25, 26, or 27 nucleotides in length.

In some embodiments of the dsRNAi inhibitor molecule, the antisense strand is between 18 and 66 nucleotides in length. Typically, the antisense strand comprises a sequence that is sufficiently complementary to a sequence in the target gene mRNA to direct the effect of the nucleic acid inhibitor molecule to the target gene. In certain embodiments, the antisense strand comprises a sequence that is fully complementary with a sequence contained in the target gene mRNA where the fully complementary sequence is between 18 and 40 nucleotides long. In certain of those embodiments, the antisense strand is between 20 and 50 nucleotides in length. In certain embodiments, the antisense strand is between 20 and 30 nucleotides in length. In certain embodiments, the antisense strand is 21, 22, 23, 24, 25, 26, 27, or 28 nucleotides in length. In certain embodiments, the antisense strand is between 35 and 40 nucleotides in length. In certain of those embodiments, the antisense strand is 36, 37, 38, or 39 nucleotides in length.

In some embodiments of the dsRNAi inhibitor molecule, the sense and antisense strands form a duplex structure of between 15 and 50 base pairs. In certain embodiments, the duplex region is between 15 and 30 base pairs in length, such as between 19 and 30, more typically between 18 and 26, such as between 19 and 23, and in certain instances between 19 and 21 base pairs in length. In certain embodiments, the double-stranded region is 19, 20, 21, 22, 23, 24, 25, or 26 base pairs in length.

In some embodiments, the dsRNAi inhibitor molecule may further comprise one or more single-stranded nucleotide overhang(s). Typically, the dsRNAi inhibitor molecule has a single-stranded overhang of 1-10, 1-4, or 1-2 nucleotides. The single stranded overhang is typically located at the 3'-end of the sense strand and/or the 3'-end of the antisense strand. In certain embodiments, a single-stranded overhang of 1-10, 1-4, or 1-2 nucleotides is located at the 5'-end of the antisense strand. In certain embodiments, a single-stranded overhang of 1-10, 1-4, or 1-2 nucleotides is located at the 5'-end of the sense strand. In certain embodiments, the single-stranded overhang of 1-2 nucleotides is located at the 3'-end of the antisense strand. In certain embodiments, the single-stranded overhang of 10 nucleotides is located at the 5'-end of the antisense strand. In certain embodiments, the dsRNA inhibitor molecule has a blunt end, typically at the 5'-end of the antisense strand.

In certain embodiments, the dsRNAi inhibitor molecule comprises a sense and an antisense strand and a duplex region of between 19-21 nucleotides, wherein the sense strand is 19-21 nucleotides in length and the antisense strand is 21-23 nucleotides in length and comprises a single-stranded overhang of 1-2 nucleotides at its 3'-terminus.

In certain embodiments, the dsRNAi inhibitor molecule has an antisense strand of 21 nucleotides in length and a sense strand of 21 nucleotides in length, where there is a two nucleotide 3'-passenger strand overhang on the right side of the molecule (3'-end of sense strand/5'-end of antisense strand) and a two nucleotide 3'-guide strand overhang on the left side of the molecule (5'-end of the sense strand/3'-end of the antisense strand). In such molecules, there is a 19 base pair duplex region.

In certain embodiments, the dsRNAi inhibitor molecule has an antisense strand of 23 nucleotides in length and a sense strand of 21 nucleotides in length, where there is a blunt end on the right side of the molecule (3'-end of sense strand/5'-end of antisense strand) and a two nucleotide 3'-guide strand overhang on the left side of the molecule (5'-end of the sense strand/3'-end of the antisense strand). In such molecules, there is a 21 base pair duplex region.

In certain embodiments, the dsRNAi inhibitor molecule comprises a sense and an antisense strand and a duplex region of between 18-34 nucleotides, where the sense strand is 25-34 nucleotides in length and the antisense strand is 26-38 nucleotides in length and comprises 1-5 single-stranded nucleotides at its 3' terminus. In certain embodiments, the sense strand is 26 nucleotides, the antisense strand is 38 nucleotides and has a single-stranded overhang of 2 nucleotides at its 3' terminus and a single-stranded overhang of 10 nucleotides at its 5' terminus, and the sense strand and antisense strand form a duplex region of 26 nucleotides. In certain embodiments, the sense strand is 25 nucleotides, the antisense strand is 27 nucleotides and has a single-stranded overhang of 2 nucleotides at its 3' terminus, and the sense strand and antisense strand form a duplex region of 25 nucleotides.

In some embodiments, the dsRNAi inhibitor molecules include a stem and loop. Typically, a 3'-terminal region or 5'-terminal region of a passenger strand of a dsRNAi inhibitor molecule form a single stranded stem and loop structure.

In some embodiments, the dsRNAi inhibitor molecule contains a stem and tetraloop. In embodiments where the dsRNAi inhibitor molecule contains a stem and tetraloop, the passenger strand contains the stem and tetraloop and ranges from 20-66 nucleotides in length. Typically, the guide and passenger strands are separate strands, each having a 5' and 3' end that do not form a contiguous oligonucleotide (sometimes referred to as a "nicked" structure).

In certain of those embodiments, the guide strand is between 15 and 40 nucleotides in length. In certain embodiments, the extended part of the passenger strand that contains the stem and tetraloop is on 3'-end of the strand. In certain other embodiments, the extended part of the passenger strand that contains the stem and tetraloop is on 5'-end of the strand.

In certain embodiments, the passenger strand of a dsRNAi inhibitor molecule containing a stem and tetraloop is between 34 and 40 nucleotides in length and the guide strand of the dsRNAi inhibitor molecule contains between 20 and 24 nucleotides, where the passenger strand and guide strand form a duplex region of 18-24 nucleotides.

Figure 1B:
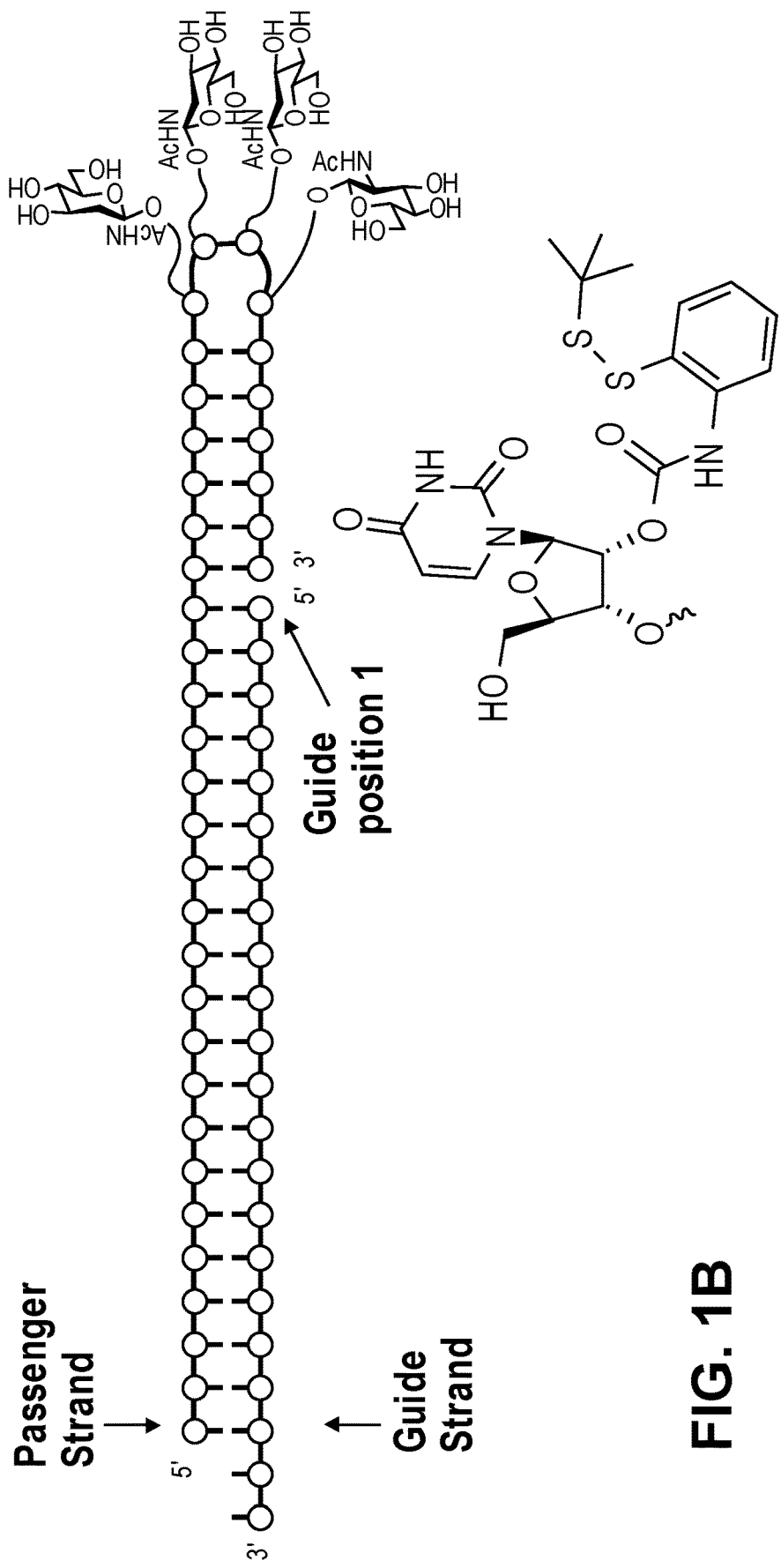
Figure 1B:
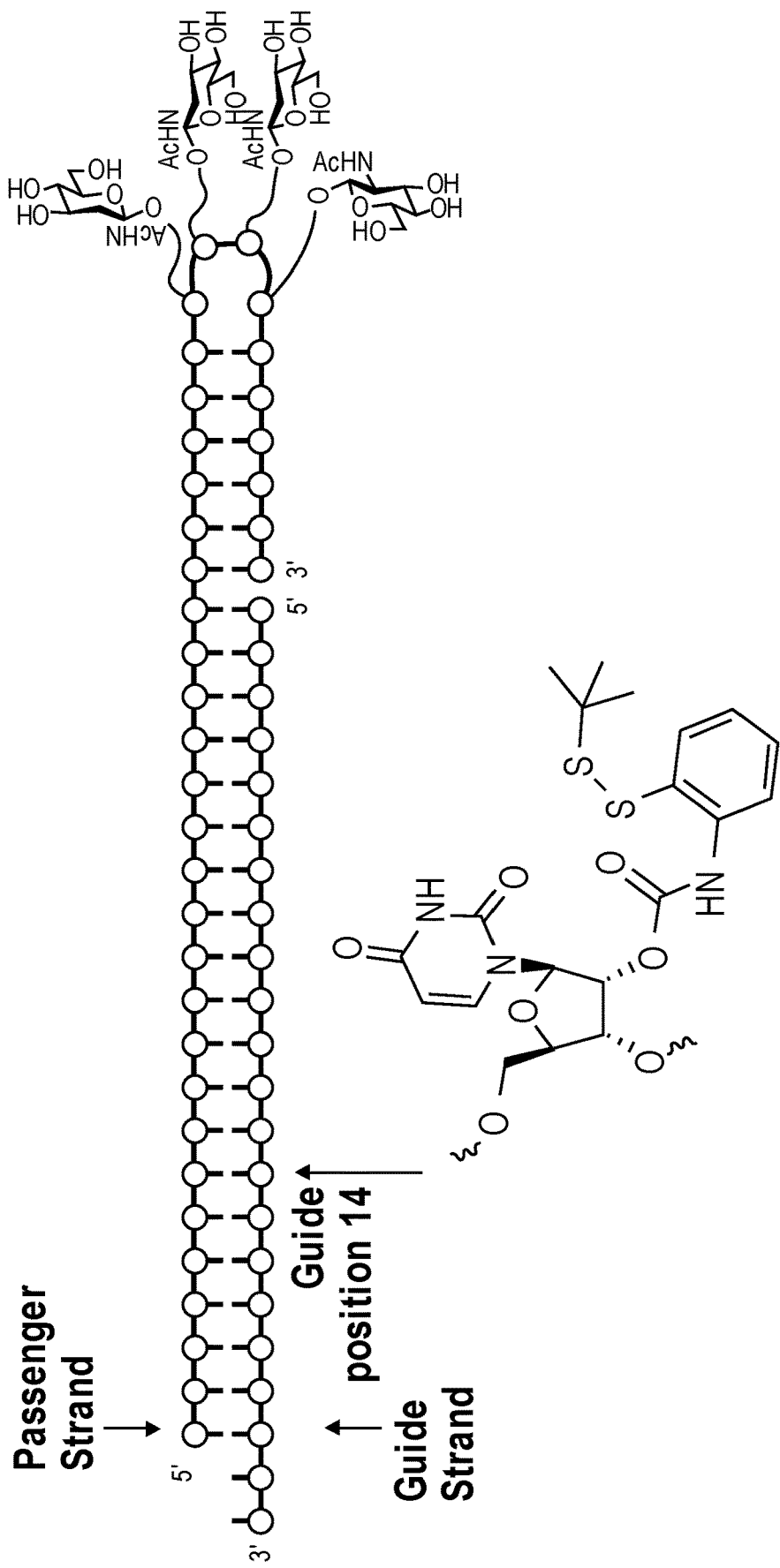

In certain embodiments, the dsRNAi inhibitor molecule comprises (a) a passenger strand that contains a stem and tetraloop and is 36 nucleotides in length, wherein the first 20 nucleotides from the 5'-end are complementary to the guide strand and the following 16 nucleotides form the stem and tetraloop and (b) a guide strand that is 22 nucleotides in length and has a single-stranded overhang of two nucleotides at its 3' end, wherein the guide and passenger strands are separate strands that do not form a contiguous oligonucleotide (see e.g., FIGS. 1A and 1B).

In certain embodiments, the nucleic acid inhibitor molecule includes one or more deoxyribonucleotides. Typically, the nucleic acid inhibitor molecule contains fewer than 5 deoxyribonucleotides. In certain embodiments, the nucleic acid inhibitor molecule includes one or more ribonucleotides. In certain embodiments, all of the nucleotides of the nucleic acid inhibitor molecule are ribonucleotides.

In some embodiments, the at least one glutathione-sensitive nucleotide of a double stranded nucleic acid inhibitor molecule, e.g., a dsRNAi inhibitor molecule, is located on the passenger strand. In another embodiment, the at least one glutathione-sensitive nucleotide is located on the guide strand. In some embodiments, the at least one glutathione-sensitive nucleotide is located in a duplex region. In some embodiments, the at least one glutathione-sensitive nucleotide is located in an overhang region.

In certain embodiments, the nucleic acid inhibitor molecule is a single-stranded nucleic acid inhibitor molecule comprising at least one nucleotide having a glutathione-sensitive moiety, as described herein. Single stranded nucleic acid inhibitor molecules are known in the art. For example, recent efforts have demonstrated activity of ssRNAi inhibitor molecules (see, e.g., Matsui et al., *Molecular Therapy*, 2016, 24(5):946-55. And, antisense molecules have been used for decades to reduce expression of specific target genes. Pelechano and Steinmetz, *Nature Review Genetics*, 2013, 14:880-93. A number of variations on the common themes of these structures have been developed for a range of targets. Single stranded nucleic acid inhibitor molecules include, for example, conventional antisense oligonucleotides, microRNA, ribozymes, aptamers, antagomirs, and ssRNAi inhibitor molecules, all of which are known in the art.

In certain embodiments, the nucleic acid inhibitor molecule is a ssRNAi inhibitor molecule having 14-50, 16-30, or 15-25 nucleotides. In other embodiments, the ssRNAi inhibitor molecule has 18-22 or 20-22 nucleotides. In certain embodiments, the ssRNAi inhibitor molecule has 20 nucleotides. In other embodiments, the ssRNAi inhibitor molecule has 22 nucleotides. In certain embodiments, the nucleic acid inhibitor molecule is a single-stranded oligonucleotide that inhibits exogenous RNAi inhibitor molecules or natural miRNAs.

In certain embodiments, the nucleic acid inhibitor molecule is a single-stranded antisense oligonucleotide having 8-80, 14-50, 16-30, 12-25, 12-22, 14-20, 18-22, or 20-22 nucleotides. In certain embodiments, the single-stranded antisense oligonucleotide has 18-22, such as 18-20 nucleotides.

In certain embodiments, the antisense oligonucleotide or a portion thereof is fully complementary to a target nucleic acid or a specific portion thereof. In certain embodiments, the antisense oligonucleotide or a portion thereof is complementary to at least 12, 13, 14, 15, 16, 17, 18, 19, 20, or more contiguous nucleotides of the target nucleic acid. In certain embodiments, the antisense oligonucleotide contains no more than 5, 4, 3, 2, or 1 non-complementary nucleotides relative to the target nucleic acid or portion thereof. It is possible to decrease the length of the antisense oligonucleotide and/or introduce mismatch bases without eliminating activity.

As described herein, the sugar moiety of one or more nucleotides can be modified with a glutathione-sensitive moiety, typically at the 2'-carbon of the sugar moiety. Typically one or two nucleotides of a nucleic acid inhibitor molecule are reversibly modified with a glutathione-sensitive moiety. In certain embodiments, more than two nucleotides of a nucleic acid inhibitor molecule, such as three, four, five nucleotides, or more, are reversibly modified with a glutathione-sensitive moiety. In certain embodiments, most of the nucleotides are reversibly modified with a glutathione-sensitive moiety. In certain embodiments, all or substantially all of the nucleotides of the oligonucleotide contain a glutathione-sensitive moiety.

In certain embodiments, the passenger strand of a dsRNAi inhibitor molecule contains one or more nucleotides that are reversibly modified with a glutathione-sensitive moiety. In certain embodiments, the guide strand of a dsRNAi inhibitor molecule contains one or more nucleotides that are reversibly modified with a glutathione-sensitive moiety. In certain embodiments, the guide and passenger strands of a dsRNAi inhibitor molecule each contain one or more nucleotides that are reversibly modified with a glutathione-sensitive moiety.

In some embodiments, the presence of at least one glutathione-sensitive moiety in a nucleic acid inhibitor molecule reduces degradation of the oligonucleotide resulting from nucleases in serum, for example, and/or nucleases within cells, e.g., within vesicles such as endosomal vesicles, lysosomal vesicle and/or fused endosomal/lysosomal vesicles. For example, placing a glutathione-sensitive moiety at either the 5'- or 3'-terminal nucleotide of the nucleic acid inhibitor molecule can protect against degradation from nucleases. In addition, certain double stranded nucleic acid inhibitor molecules contain a single stranded overhang region on either the passenger or guide strand or both, which is more susceptible to nuclease degradation. Modifying this single stranded overhang region can protect such double stranded nucleic acid inhibitor molecules against degradation from nucleases.

In some embodiments, the at least one glutathione-sensitive moiety is located at the 5'-terminal nucleotide of a single stranded nucleic acid inhibitor molecule or the 5'-terminal nucleotide of the passenger strand or the guide strand of a double-stranded nucleic acid inhibitor molecule. In certain embodiments, the glutathione-sensitive moiety is located at the 5'-carbon of the 5'-terminal nucleotide. In other embodiments, the glutathione-sensitive moiety is located at the 2'-carbon of the 5'-terminal nucleotide. In certain embodiments of the double stranded nucleic acid inhibitor molecule, the glutathione-sensitive moiety located at the 5'-terminal nucleotide of the passenger or guide strand is in an overhang region.

In some embodiments, the at least one glutathione-sensitive moiety is located at the 3'-terminal nucleotide of a single stranded nucleic acid inhibitor molecule or the 3'-terminal nucleotide of the passenger strand or the guide strand of a double stranded nucleic acid inhibitor molecule. In certain embodiments, the glutathione-sensitive moiety is located at the 3'-carbon of the 3'-terminal nucleotide. In other embodiments, the glutathione-sensitive moiety is located at the 2'-carbon of the 3'-terminal nucleotide. In certain embodiments of the double stranded nucleic acid inhibitor molecule, the glutathione-sensitive moiety located at the 3'-terminal nucleotide of the passenger or guide strand is in an overhang region.

Irreversible chemical modifications at nucleotide position 2 and position 14 of an RNAi inhibitor molecule, such as modifications at the 2'-carbon of the sugar, are generally not well tolerated. Without intending to be bound by any theory, it is possible that these nucleotide positions are sensitive to steric bulk. In some embodiments, the at least one glutathione-sensitive moiety is located at nucleotide position 2 of a single stranded nucleic acid inhibitor molecule or position 2 of the guide strand of a double stranded nucleic acid inhibitor molecule. In some embodiments, the at least one glutathione-sensitive moiety is located at nucleotide position 14 of a single stranded nucleic acid inhibitor molecule or position 14 of the guide strand of a double stranded nucleic acid inhibitor molecule.

In some embodiments, the at least one glutathione-sensitive moiety is on one or more nucleotides located at or adjacent to the Ago2 cleavage site of the passenger strand of a dsRNAi inhibitor molecule. Typically, Ago2 cleaves the passenger strand at a phosphodiester bond between the two nucleotides opposing nucleotide positions 10 and 11 of the guide strand, as measured from the 5'-end of the guide strand. Thus, for example, if the guide strand has 22 nucleotides and a two-base pair overhang (or 20 nucleotides and no overhang), Ago2 should cleave between nucleotide positions 10 and 11 of the passenger strand. If the guide strand has 21 nucleotides and a two-base pair overhang (or 19 nucleotides and no overhang), Ago2 should cleave between nucleotide positions 9 and 10 of the passenger strand. In certain embodiments, the dsRNAi inhibitor molecule contains a glutathione-sensitive moiety on one, two, or three nucleotides that are immediately 5' of the Ago2 cleavage site. In certain embodiments, the dsRNAi inhibitor molecule contains a glutathione-sensitive moiety on one, two, or three nucleotides that are immediately 3' of the Ago2 cleavage site. In certain embodiments, the dsRNAi inhibitor molecule contains a glutathione-sensitive moiety on both sides of the Ago2 cleavage site, including, for example, on one, two, or three nucleotides that are immediately 5' of the Ago2 cleavage site and on one, two, or three nucleotides that are immediately 3' of the Ago2 cleavage site.

B. Other Modifications of the Glutathione-Sensitive Oligonucleotides

An oligonucleotide that is modified with a reversible glutathione-sensitive moiety as described herein, can be further modified on one or more nucleotides using, for example, other nucleotide modifications known in the art, including the irreversible modifications described herein. Typically, multiple nucleotide subunits of the oligonucleotide of interest are modified to improve various characteristics of the molecule such as resistance to nucleases or lowered immunogenicity. See, e.g., Bramsen et al. (2009), Nucleic Acids Res., 37, 2867-2881. Many nucleotide modifications have been used in the oligonucleotide field, particularly for nucleic acid inhibitor molecules. Such irreversible modifications can be made on any part of the nucleotide, including the sugar moiety, the phosphodiester linkage, and the nucleobase. Typical examples of nucleotide modification include, but are not limited to, 2'-F, 2'-O-methyl ("2'-OMe" or "2'-OCH$_3$"), 2'-O-methoxyethyl ("2'-MOE" or "2'-OCH$_2$CH$_2$OCH$_3$"), and 5'-methylcytosine. Irreversible modifications can occur at other parts of the nucleotide, such as the 5'-carbon, as described herein.

In certain embodiments, the ring structure of the sugar moiety is modified, including, but not limited to, Locked Nucleic Acid ("LNA") structures, Bridged Nucleic Acid ("BNA") structures, and Unlocked Nucleic Acid ("UNA") structures, as discussed previously.

Modified nucleobases include nucleobases other than adenine, guanine, cytosine, thymine and uracil at the 1'-position, as known in the art and as described herein. A typical example of a modified nucleobase is 5'-methylcytosine.

The natural occurring internucleotide linkage of RNA and DNA is a 3' to 5' phosphodiester linkage. Modified phosphodiester linkages include non-naturally occurring internucleotide linking groups, including internucleotide linkages that contain a phosphorous atom and internucleotide linkages that do not contain a phosphorous atom, as known in the art and as described herein. Typically, the oligonucleotide contains one or more phosphorous-containing internucleotide linking groups, as described herein. In other embodiments, one or more of the internucleotide linking groups of the nucleic acid inhibitor molecule is a non-phosphorus containing linkage, as described herein. In certain embodiments, the oligonucleotide contains one or more phosphorous-containing internucleotide linking groups and one or more non-phosphorous containing internucleotide linking groups.

The 5'-end of the glutathione-sensitive oligonucleotide can include a natural substituent, such as a hydroxyl or a phosphate group. In certain embodiments, a hydroxyl group is attached to the 5'-terminal end of the glutathione-sensitive oligonucleotide. In certain embodiments, a phosphate group is attached to the 5'-terminal end of the glutathione-sensitive oligonucleotide. Typically, the phosphate is added to a monomer prior to oligonucleotide synthesis. In other embodiments, 5'-phosphorylation is accomplished naturally after an oligonucleotide of the disclosure is introduced into the cytosol, for example, by a cytosolic Clp1 kinase. In some embodiments, the 5'-terminal phosphate is a phosphate group, such as 5'-monophosphate [$(HO)_2(O)P—O-5'$], 5'-diphosphate [$(HO)_2(O)P—O—P(HO)(O)—O-5'$] or a 5'-triphosphate[$(HO)_2(O)P—O—(HO)(O)P—O—P(HO)(O)—O-5'$].

The 5'-end of the glutathione-sensitive oligonucleotide can also be modified. For example, in some embodiments, the 5'-end of the glutathione-sensitive oligonucleotide is attached to a phosphoramidate [$(HO)_2(O)P—NH-5'$, $(HO)(NH_2)(O)P—O-5'$]. In certain embodiments, the 5'-terminal end of the glutathione-sensitive oligonucleotide is attached to a phosphate mimic. Suitable phosphate mimics include 5'-phosphonates, such as 5'-methylenephosphonate (5'-MP) and 5'-(E)-vinylphosphonate (5'-VP). Lima et al., Cell, 2012, 150-883-94; WO2014/130607. Other suitable phosphate mimics include 4'-phosphate analogs that are bound to the 4'-carbon of the sugar moiety (e.g., a ribose or deoxyribose or analog thereof) of the 5'-terminal nucleotide of an oligonucleotide, as described in U.S. Provisional Application No. 62/393,401, which is hereby incorporated by reference in its entirety. For example, in some embodiments, the 5'-end of the nucleic acid inhibitor molecule is attached to an oxymethylphosphonate, where the oxygen atom of the oxymethyl group is bound to the 4'-carbon of the sugar moiety or analog thereof. In certain embodiments, the 4'-oxymethylphosphonate is represented by the formula —O—$CH_2$—$PO(OH)_2$ or —O—$CH_2$—$PO(OR)_2$, where R is independently selected from H, $CH_3$, an alkyl group, or a protecting group. In certain embodiments, the alkyl group is $CH_2CH_3$. More typically, R is independently selected from H, $CH_3$, or $CH_2CH_3$. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, an oligonucleotide is fully modified, wherein every nucleotide of the fully modified oligonucleotide is modified with either an irreversible modification or a reversible, glutathione-sensitive moiety, as described herein. In certain embodiments, every nucleotide of an oligonucleotide is modified, wherein every nucleotide that is not modified with a glutathione-sensitive moiety is modified with an irreversible modification. In certain embodiments, the oligonucleotide contains ribonucleotides and deoxyribonucleotides and every ribonucleotide in the oligonucleotide is modified with either an irreversible modification or a reversible, glutathione-sensitive moiety, as described herein. In certain embodiments, substantially all of the nucleotides of an oligonucleotide are modified. In certain embodiments, more than half of the nucleotides of an oligonucleotide are modified. In certain embodiments, more than half of the nucleotides of an oligonucleotide contain an irreversible modification. In certain embodiments, less than half of the nucleotides of an oligonucleotide are modified. In certain embodiments, less than half of the nucleotides of an oligonucleotide contain an irreversible modification. In certain embodiments, the oligonucleotide does not contain any modifications other than the one or more glutathione-sensitive nucleotides. Modifications can occur in groups on the oligonucleotide chain or different modified nucleotides can be interspersed.

In some embodiments, the irreversible chemical modification is located at the same nucleotide as that containing the glutathione-sensitive moiety. In other embodiments, the irreversible chemical modification is located at one or more nucleotides that do not contain the glutathione-sensitive moiety.

In some embodiments, all of the nucleotides in a single stranded nucleic acid inhibitor molecule or in the guide strand or passenger strand of a double stranded nucleic acid inhibitor molecule are modified with an irreversible chemical modification, except for one nucleotide, which is reversibly modified with a glutathione-sensitive moiety as described herein. In other embodiments, at least one, such as at least two, three, four, five, six, seven, eight, nine, or 10 nucleotides of a single stranded nucleic acid inhibitor molecule or the guide strand or passenger strand of a double stranded nucleic acid inhibitor molecule are reversibly modified with a glutathione-sensitive moiety and at least one, such as at least two, three, four, five, six, seven, eight, nine, or 10 nucleotides of a single stranded nucleic acid inhibitor molecule or the guide strand or passenger of a double stranded nucleic acid inhibitor molecule are chemically modified with an irreversible chemical modification. In some embodiments, all of the nucleotides of a single stranded nucleic acid inhibitor molecule or the guide strand or passenger strand of a double stranded nucleic acid inhibitor molecule contain at least one glutathione-sensitive moiety as described herein or at least one irreversible modification.

In certain embodiments of the nucleic acid inhibitor molecule, every nucleotide is modified at the 2'-carbon. In certain embodiments of the nucleic acid inhibitor molecule (or the sense strand and/or antisense strand thereof) every nucleotide that is not modified with a glutathione-sensitive moiety is modified is modified with 2'-F, 2'-O-Me, and/or 2'-MOE. In certain embodiments of the nucleic acid inhibitor molecule, from one to every phosphorous atom is modified and from one to every ribonucleotide is modified at the 2'-carbon.

III. GLUTATHIONE-SENSITIVE MONOMERS (NUCLEOSIDES AND NUCLEOTIDES)

One aspect of the present disclosure relates to reversibly modified nucleosides or nucleotides comprising a glutathione-sensitive moiety, including glutathione-sensitive nucleoside phosphoramidites that can be used in standard oligonucleotide synthesis methods and glutathione-sensitive nucleosides or nucleotides without a phosphoramidite group that have therapeutic utility, for example, as antiviral agents. Typically, the reversible modification comprises a glutathione-sensitive moiety at the sugar moiety of the nucleoside or nucleotide, e.g. a deoxyribose or ribose (or analogs thereof). Typically, the glutathione-sensitive moiety in the nucleoside or nucleotide is located at the 2'-carbon of a deoxyribose or ribose (or analogs thereof). In other embodiments, the glutathione-sensitive moiety in the nucleoside or nucleotide is located at the 5'-carbon of a ribose or deoxyribose (or analogs thereof). In yet other embodiments, the glutathione-sensitive moiety in the nucleoside or nucleotide is located at the 3'-carbon of a ribose or deoxyribose (or analogs thereof).

In some embodiments, the glutathione-sensitive moiety comprises a sulfonyl group. In other embodiments, the glutathione-sensitive moiety comprises a disulfide bridge.

A. Glutathione-Sensitive Nucleoside Phosphoramidites

This application discloses nucleosides that are reversibly modified with a glutathione-sensitive moiety and that are compatible with phosphoramidite oligonucleotide synthesis methods. Thus, in another aspect, the present disclosure relates to reversibly modified nucleoside phosphoramidites comprising a glutathione-sensitive moiety and methods of synthesizing oligonucleotides using these glutathione-sensitive nucleoside phosphoramidites.

In certain embodiments, the nucleoside comprises a phosphoramidite and a glutathione-sensitive moiety, wherein the nucleoside is compatible with phosphoramidite oligonucleotide synthesis methods. Typically, the phosphoramidite is bound to the 5'- or 3'-carbon of the sugar moiety of the nucleoside and the glutathione-sensitive moiety is bound to an oxygen atom that is covalently bound to the 2'-carbon of the sugar moiety (e.g., ribose) of the nucleoside. In some embodiments, the glutathione-sensitive moiety is represented by Formula II, as described previously. In certain embodiments, Formula II is Formula IIa, as described herein. In other embodiments, the glutathione-sensitive moiety is represented by Formula III, as described previously. In some embodiments, Formula III is selected from Formula IIIa or IIIb, as described previously. In some embodiments, Formula III is selected from Formula IIIa(i) or IIIb(i), as described previously. In yet other embodiments, the glutathione-sensitive moiety is represented by Formula IV, as described previously. In some embodiments, Formula IV is selected from Formula IVa, IVb, IVc, IVd, or IVe, as described previously. In some embodiments, Formula IV is selected from Formula IVa(i), IVb(i), IVb(ii), IVc(i), or IVd(i), as described previously. In some embodiments, Formula IVe is selected from Formula IVe(i), IVe(ii), IVe(iii), IVe(iv), IVe(v), IVe(vi), IVe(vii), IVe(viii), IVe(ix), IVe(x), or IVe(xi), as described previously.

1. Formula VIII

In some embodiments, the nucleoside phosphoramidite is represented by the following Formula:

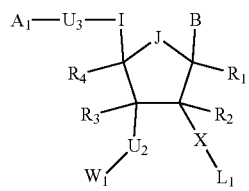

VIII wherein $L_1$ is a glutathione-sensitive moiety;

wherein $A_1$ is absent, hydrogen, a phosphate group, a phosphate mimic, a phosphoramidate, a phosphoramidite, a protecting group, or a solid support;

wherein $W_1$ is a phosphoramidite, a protecting group, a solid support, hydrogen, halogen, OR', SR', NR'R", a substituted or unsubstituted aliphatic, a substituted or unsubstituted aryl, a substituted or unsubstituted heteroaryl, a substituted or unsubstituted cycloalkyl, a substituted or unsubstituted heterocycle, wherein R' and R" are each independently selected from hydrogen, halogen, a substituted or unsubstituted aliphatic, an aryl, a heteroaryl, a heterocycle or are taken together to form a heterocyclic ring;

wherein $U_3$ is hydrogen or selected from O, S, NR' or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl;

wherein at least $A_1$ is a phosphoramidite and $U_3$ is O or at least $W_1$ is a phosphoramidite and $U_2$ is O;

wherein X is O, S, Se or NR', wherein R' is selected from hydrogen, halogen, a substituted or unsubstituted aliphatic, an aryl, a substituted or unsubstituted heteroaryl or a substituted or unsubstituted heterocycle;

wherein $R_1$, $R_2$, $R_3$ and $R_4$ are each independently selected from hydrogen, halogen, OH, $C_1$-$C_6$ alkyl, $C_1$-$C_6$ haloalkyl or wherein two of $R_1$, $R_2$, $R_3$ and $R_4$ are taken together to form a 5-8 membered ring, wherein the ring optionally contains a heteroatom;

wherein J is O, S, NR', CR'R", wherein each of R' and R" is independently selected from hydrogen, halogen, a substituted or unsubstituted aliphatic, aryl or heteroaryl;

wherein B is selected from hydrogen, a substituted or unsubstituted aliphatic, a natural nucleobase, a modified nucleobase or a universal nucleobase;

wherein $U_2$ is absent or selected from O, S, NR', or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle or a substituted or unsubstituted cycloalkyl;

wherein I is absent or is selected from O, S, NR', CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl; and wherein I and $U_3$ can be combined to form CR'—CR" alkyl, CR'—CR" alkenyl, CR'—CR" alkynyl, a substituted or unsubstituted aliphatic, an aryl, a heteroaryl a heterocycle or taken together to form cycloalkyl or heterocyclic ring.

Typically, the glutathione-sensitive moiety ($L_1$) comprises a disulfide bridge or a sulfonyl group. In certain embodiments, the glutathione-sensitive moiety comprises a disulfide bridge. In other embodiments, the glutathione-sensitive moiety comprises a sulfonyl group.

In some embodiments, the glutathione-sensitive moiety ($L_1$) is represented by Formula II, Formula III, or Formula IV, as described previously.

In certain embodiments, the glutathione-sensitive moiety ($L_1$) is represented by Formula IIa, as described previously.

In some embodiments, the glutathione-sensitive moiety ($L_1$) is represented by Formula IIIa or IIIb, as described previously.

In some embodiments, the glutathione-sensitive moiety ($L_1$) is represented by Formula IIIa(i) or IIIb(i), as described previously.

In some embodiments, the glutathione-sensitive moiety ($L_1$) is represented by Formula IVa, IVb, IVc, IVd, or IVe, as described previously.

In some embodiments, the glutathione-sensitive moiety ($L_1$) is represented by Formula IVa(i), IVb(i), IVb(ii), IVc(i), or IVd(i), as described previously.

In some embodiments, the glutathione-sensitive moiety ($L_1$) is represented by Formula IVe(i), IVe(ii), IVe(iii), IVe(iv), IVe(v), IVe(vi), IVe(vii), IVe(viii), IVe(ix), IVe(x), or IVe(xi), as described previously.

In certain embodiments, X is O.

In certain embodiments, $R_1$, $R_2$, $R_3$ and $R_4$ are hydrogen.

In certain embodiments, J is O.

In certain embodiments, B is a natural nucleobase.

In certain embodiments, $U_2$ is O.

In certain embodiments, $W_1$ is a phosphoramidite, a protecting group, or a hydrogen.

In certain embodiments, $A_1$ is a phosphoramidite, a protecting group, or a hydrogen.

In certain embodiments, $W_1$ is a phosphoramidite and $A_1$ is a protecting group.

In certain embodiments, $W_1$ is a protecting group and $A_1$ is a phosphoramidite.

In certain embodiments, I is $CH_2$.

In certain embodiments, $U_3$ is O.

In certain embodiments, X is O, $R_1$, $R_2$, $R_3$ and $R_4$ are hydrogen, and J is O.

In certain embodiments, X is O; $R_1$, $R_2$, $R_3$ and $R_4$ are hydrogen; J is O; B is a natural nucleobase; $U_2$ is O; I is $CH_2$; $W_1$ is a phosphoramidite, $A_1$ is a protecting group, and $U_3$ is O.

In certain embodiments, X is O; $R_1$, $R_2$, $R_3$ and $R_4$ are hydrogen; J is O; B is a natural nucleobase; $U_2$ is O; I is $CH_2$; $W_1$ is a protecting group, $A_1$ is a phosphoramidite, and $U_3$ is O.

In certain embodiments, the phosphoramidite has the formula —P($OR^x$)—N($R^y$)$_2$, wherein $R^x$ is selected from the group consisting of an optionally substituted methyl, 2-cyanoethyl and benzyl, wherein each of $R^y$ is selected from the group consisting of an optionally substituted ethyl and isopropyl. In certain embodiments, $R^x$ is 2-cyanoethyl and $R^y$ is isopropyl.

2. Formula IX

In certain embodiments, the nucleoside phosphoramidite is represented by the following Formula:

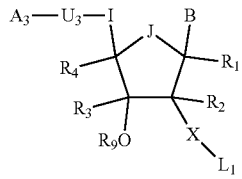

wherein $L_1$ is a glutathione-sensitive moiety;

wherein $R_9$ is a phosphoramidite;

wherein X is O, S, Se or NR', wherein R' is selected from hydrogen, halogen, a substituted or unsubstituted aliphatic, an aryl, a substituted or unsubstituted heteroaryl or a substituted or unsubstituted heterocycle;

wherein $R_1$, $R_2$, $R_3$ and $R_4$ are each independently selected from hydrogen, halogen, OH, $C_1$-$C_6$ alkyl, $C_1$-$C_6$ haloalkyl or wherein two of $R_1$, $R_2$, $R_3$ and $R_4$ are taken together to form a 5-8 membered ring, wherein the ring optionally contains a heteroatom;

wherein J is O, S, NR', CR'R", wherein each of R' and R" is independently selected from hydrogen, halogen, a substituted or unsubstituted aliphatic, aryl or heteroaryl;

wherein B is hydrogen, a natural nucleobase, a modified nucleobase or a universal nucleobase;

wherein I is absent or is selected from O, S, NR', CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl;

wherein $U_3$ is a hydrogen or selected from O, S, NR', or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl;

wherein I and $U_3$ can be combined to form CR'—CR" alkyl, CR'—CR" alkenyl, CR'—CR" alkynyl, a substituted or unsubstituted aliphatic, an aryl, a heteroaryl a heterocycle or taken together to form cycloalkyl or heterocyclic ring; and wherein $A_3$ is absent, hydrogen, a phosphate group, a phosphate mimic, a phosphoramidate, a protecting group, or a solid support.

Typically, $L_1$ comprises a disulfide bridge or a sulfonyl group. In certain embodiments, the glutathione-sensitive moiety comprises a disulfide bridge. In other embodiments, the glutathione-sensitive moiety comprises a sulfonyl group.

In some embodiments, $L_1$ is represented by Formula II, as described previously. In some embodiments, $L_1$ is represented by Formula IIa, as described previously.

In other embodiments, $L_1$ is represented by Formula III, as described previously. In some embodiments, Formula III is selected from Formula IIIa, IIIa(i), IIIb, or IIIb(i), as described previously.

In yet other embodiments, $L_1$ is represented by Formula IV, as described previously. In some embodiments, Formula IV is selected from Formula IVa, IVb, IVc, IVd, or IVe, as described previously. In some embodiments, Formula IV is selected from Formula IVa(i), IVb(i), IVb(ii), IVc(i), or IVd(i), as described previously. In some embodiments, Formula IVe is selected from Formula IVe(i), IVe(ii), IVe(iii), IVe(iv), IVe(v), IVe(vi), IVe(vii), IVe(viii), IVe(ix), IVe(x), or IVe(xi), as described previously.

In certain embodiments, X is O.

In certain embodiments, $R_1$, $R_2$, $R_3$ and $R_4$ are hydrogen.

In certain embodiments, J is O.

In certain embodiments, B is a natural nucleobase.

In certain embodiments, $A_3$ is a protecting group or a hydrogen.

In certain embodiments, I is $CH_2$.

In certain embodiments, $U_3$ is O.

In certain embodiments, X is O, $R_1$, $R_2$, $R_3$ and $R_4$ are hydrogen, and J is O.

In certain embodiments, X is O; $R_1$, $R_2$, $R_3$ and $R_4$ are hydrogen; J is O; B is a natural nucleobase; I is $CH_2$; $A_3$ is a protecting group, and $U_3$ is O.

In certain embodiments, the phosphoramidite has the formula —P(OR$^x$)—N(R$^y$)$_2$, wherein R$^x$ is selected from the group consisting of an optionally substituted methyl, 2-cyanoethyl and benzyl, wherein each of R$^y$ is selected from the group consisting of an optionally substituted ethyl and isopropyl. In certain embodiments, R$^x$ is 2-cyanoethyl and R$^y$ is isopropyl.

3. Formula X

In certain embodiments, the nucleoside phosphoramidite is represented by the following Formula:

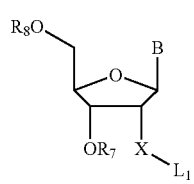

$L_1$ is a glutathione-sensitive moiety;

$R_8$ is H, a protecting group, a solid support, or a phosphoramidite;

$R_7$ is H, a protecting group, a solid support, or a phosphoramidite;

wherein if $R_8$ is a phosphoramidite, $R_7$ is H, a solid support, or a protecting group or if $R_8$ is H, a solid support, or a protecting group, $R_7$ is a phosphoramidite;

wherein B is a natural nucleobase, a modified nucleobase or a universal nucleobase; and wherein X is O, S, Se, NR', where R' can be selected from hydrogen, halogen, aliphatic or substituted aliphatic, aryl, substituted or unsubstituted heteroaryl, substituted or unsubstituted heterocyclic.

Typically, $L_1$ comprises a disulfide bridge or a sulfonyl group. In certain embodiments, $L_1$ comprises a disulfide bridge. In other embodiments, $L_1$ comprises a sulfonyl group.

In some embodiments, $L_1$ is represented by Formula II, as described previously. In some embodiments, $L_1$ is represented by Formula IIa, as described previously.

In other embodiments, $L_1$ is represented by Formula III, as described previously. In some embodiments, Formula III is selected from Formula IIIa, IIIa(i), IIIb, or IIIb(i), as described previously.

In yet other embodiments, $L_1$ is represented by Formula IV, as described previously. In some embodiments, Formula IV is selected from Formula IVa, IVb, IVc, IVd, or IVe, as described previously. In some embodiments, Formula IV is selected from Formula IVa(i), IVb(i), IVb(ii), IVc(i), or IVd(i), as described previously. In some embodiments, Formula IVe is selected from Formula IVe(i), IVe(ii), IVe(iii), IVe(iv), IVe(v), IVe(vi), IVe(vii), IVe(viii), IVe(ix), IVe(x), or IVe(xi), as described previously.

In certain embodiments, X is O.

In certain embodiments, B is a natural nucleobase.

In certain embodiments, the phosphoramidite has the formula —P(OR$^x$)—N(R$^y$)$_2$, wherein R$^x$ is selected from the group consisting of an optionally substituted methyl, 2-cyanoethyl and benzyl, wherein each of R$^y$ is selected from the group consisting of an optionally substituted ethyl and isopropyl. In certain embodiments, R$^x$ is 2-cyanoethyl and R$^y$ is isopropyl.

In certain embodiments, $R_8$ is a phosphoramidite having the formula —P(OR$^x$)—N(R$^y$)$_2$ and $R_9$ is H or a protecting group.

In certain embodiments, $R_9$ is a phosphoramidite having the formula —P(OR$^x$)—N(R$^y$)$_2$ and $R_8$ is H or a protecting group.

In certain embodiments, X is O; B is a natural nucleobase; $R_8$ is a protecting group, and $R_9$ is a phosphoramidite having the formula —P(OR$^x$)—N(R$^y$)$_2$.

In certain embodiments, X is O; B is a natural nucleobase; $R_8$ is a phosphoramidite having the formula —P(OR$^x$)—N(R$^y$)$_2$ and $R_9$ is a protecting group. In certain embodiments, R$^x$ is 2-cyanoethyl and R$^y$ is isopropyl.

B. Glutathione-Sensitive Nucleosides and Nucleotides without a Phosphoramidite

In some embodiments, the reversibly modified, glutathione-sensitive monomers (nucleoside or nucleotide or analogs thereof) do not contain a phosphoramidite group at the 3'-carbon or 5'-carbon of the sugar moiety. Such glutathione-sensitive monomers can be used as therapeutics, for example as nucleoside or nucleotide analogs with antiviral activity. Typically, the reversible modification comprises a glutathione-sensitive moiety at the sugar moiety of the nucleotide or nucleoside (or analogs thereof), e.g. a deoxyribose or ribose (or analogs thereof). Typically, the glutathione-sensitive moiety is located at the 2'-carbon of a deoxyribose or ribose (or analogs thereof). In some embodiments, the glutathione-sensitive moiety is located at the 5'-carbon of a ribose or deoxyribose (or analogs thereof). In other embodiments, the glutathione-sensitive moiety is located at the 3'-carbon of a ribose or deoxyribose (or analogs thereof).

In some embodiments, the glutathione-sensitive moiety comprises a sulfonyl group. In other embodiments, the glutathione-sensitive moiety comprises a disulfide bridge.

In certain embodiments, the glutathione-sensitive monomer comprises a glutathione-sensitive moiety bound to an oxygen atom that is covalently bound to the 2'-carbon of the sugar moiety (e.g., ribose) of the monomer. In some embodiments, the glutathione-sensitive moiety is represented by Formula II, as described previously. In certain embodiments, Formula II is Formula IIa, as described herein. In other embodiments, the glutathione-sensitive moiety is represented by Formula III, as described previously. In some embodiments, Formula III is selected from Formula IIIa, IIIa(i), IIIb, or IIIb(i), as described previously. In yet other embodiments, the glutathione-sensitive moiety is represented by Formula IV, as described previously. In some embodiments, Formula IV is selected from Formula IVa, IVb, IVc, IVd, or IVe, as described previously. In some embodiments, Formula IV is selected from Formula IVa(i), IVb(i), IVb(ii), IVc(i), or IVd(i), as described previously. In some embodiments, Formula IVe is selected from Formula IVe(i), IVe(ii), IVe(iii), IVe(iv), IVe(v), IVe(vi), IVe(vii), IVe(viii), IVe(ix), IVe(x), or IVe(xi), as described previously.

In certain embodiments, the glutathione-sensitive monomer (nucleoside or nucleotide or analog thereof) is formulated in a pharmaceutical composition comprising a therapeutically effective amount of the glutathione-sensitive nucleoside or nucleotide (or analog thereof) and a pharmaceutical carrier, as described in further detail below.

1. Formula XI

In some embodiments, the glutathione-sensitive nucleoside or nucleotide is represented by the following formula:

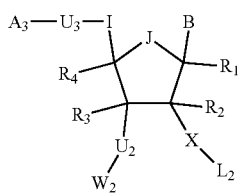

XI wherein $L_2$ is a glutathione-sensitive moiety represented by Formula II, III or IV, or is absent if one of $A_2$ or $W_2$ is the glutathione-sensitive moiety;

wherein if $L_2$ is a glutathione-sensitive moiety, X is O, S, Se, or NR', wherein R' is selected from hydrogen, halogen, a substituted or unsubstituted aliphatic, an aryl, a substituted or unsubstituted heteroaryl or a substituted or unsubstituted heterocycle or if $L_2$ is absent, X is H, OH, SH, $NH_2$, halogen, optionally substituted alkoxy, optionally substituted alkyl, optionally substituted alkenyl, optionally substituted alkynyl, optionally substituted alkylthio, optionally substituted alkylamino or dialkylamino wherein one or more methylenes in the alkyl, alkenyl, and alkynyl may be interrupted with one or more of O, S, S(O), $SO_2$, N(R'), C(O), N(R')C(O)O, OC(O)N(R') optionally substituted aryl, optionally substituted heteroaryl, optionally substituted heterocyclic or optionally substituted cycloalkyl, O, S, Se or NHR', wherein R' is selected from hydrogen, halogen, a substituted or unsubstituted aliphatic, an aryl, a substituted or unsubstituted heteroaryl or a substituted or unsubstituted heterocycle;

wherein $R_1$, $R_2$, $R_3$ and $R_4$ are each independently selected from hydrogen, halogen, OH, $C_1$-$C_6$ alkyl, $C_1$-$C_6$ haloalkyl or wherein two of $R_1$, $R_2$, $R_3$ and $R_4$ are taken together to form a 5-8 membered ring, wherein the ring optionally contains a heteroatom;

wherein J is O, S, NR', CR'R", wherein each of R' and R" is independently selected from hydrogen, halogen, a substituted or unsubstituted aliphatic, aryl or heteroaryl;

wherein B is selected from hydrogen, a natural nucleobase, a modified nucleobase or a universal nucleobase;

wherein $U_2$ is absent or selected from O, S, NR', or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle or a substituted or unsubstituted cycloalkyl;

wherein $W_2$ is a glutathione-sensitive moiety represented by Formula II, III or IV; hydrogen, halogen, OR', SR', NR'R", a substituted or unsubstituted aliphatic, a substituted or unsubstituted aryl, a substituted or unsubstituted heteroaryl, a substituted or unsubstituted cycloalkyl, a substituted or unsubstituted heterocycle, wherein R' and R" are each independently selected from hydrogen, halogen, a substituted or unsubstituted aliphatic, an aryl, a heteroaryl, a heterocycle or are taken together to form a heterocyclic ring;

wherein I is absent or is selected from O, S, NR', CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl;

wherein $U_3$ is hydrogen or selected from O, S, NR' or CR'R", wherein R' and R" are each independently hydrogen, a substituted or unsubstituted aliphatic, a substituted or unsubstituted aryl, a substituted or unsubstituted heteroaryl, a substituted or unsubstituted heterocycle and a substituted or unsubstituted cycloalkyl;

wherein I and $U_3$ can be combined to form CR'—CR" alkyl, CR'—CR" alkenyl, CR'—CR" alkynyl, a substituted or unsubstituted aliphatic, an aryl, a heteroaryl, a heterocycle or taken together to form cycloalkyl or heterocyclic ring; and wherein $A_2$ is absent, hydrogen, a phosphate group, a phosphate mimic, a phosphoramidate, or a glutathione-sensitive moiety represented by Formula II, III or IV.

In some embodiments, $A_2$ is a glutathione-sensitive moiety represented by Formula II, III or IV. In some embodiments, $W_2$ is a glutathione-sensitive moiety represented by Formula II, III or IV. In some embodiments, $L_2$ is a glutathione-sensitive moiety represented by Formula II, III or IV and neither $A_2$ nor $W_2$ is a glutathione-sensitive moiety represented by Formula II, III or IV.

In some embodiments, the glutathione-sensitive moiety is represented by Formula II, as described previously. In some embodiments, the glutathione-sensitive moiety is represented by Formula IIa, as described previously.

In other embodiments, the glutathione-sensitive moiety is represented by Formula III, as described previously. In some embodiments, Formula III is selected from Formula IIIa, IIIa(i), IIIb, or IIIb(i), as described previously. In yet other embodiments, the glutathione-sensitive moiety is represented by Formula IV, as described previously. In some embodiments, Formula IV is selected from Formula IVa, IVb, IVc, IVd, or IVe, as described previously. In some embodiments, Formula IV is selected from Formula IVa(i), IVb(i), IVb(ii), IVc(i), or IVd(i), as described previously. In some embodiments, Formula IVe is selected from Formula IVe(i), IVe(ii), IVe(iii), IVe(iv), IVe(v), IVe(vi), IVe(vii), IVe(viii), IVe(ix), IVe(x), or IV(xi), as described previously.

In certain embodiments, X is O.
In certain embodiments, $R_1$, $R_2$, $R_3$ and $R_4$ are hydrogen.
In certain embodiments, J is O.
In certain embodiments, B is a natural nucleobase.
In certain embodiments, $U_2$ is O.
In certain embodiments, $W_2$ is a hydrogen.
In certain embodiments, $U_3$ is O.
In certain embodiments, I is $CH_2$.
In certain embodiments, $A_2$ is hydrogen or a phosphate group.
In certain embodiments, X is O, $R_1$, $R_2$, $R_3$ and $R_4$ are hydrogen, and J is O.
In certain embodiments, X is O; $R_1$, $R_2$, $R_3$ and $R_4$ are hydrogen; J is O; B is a natural nucleobase; $U_2$ is O; I is $CH_2$; $W_2$ is a hydrogen, $U_3$ is O; and $A_2$ is hydrogen or a phosphate group.

2. Formula XII

In some embodiments, the glutathione-sensitive nucleoside or nucleotide monomer is represented by the following formula:

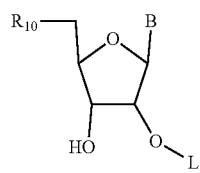

wherein $R_{10}$ is a hydroxyl, a phosphate mimic, or a phosphate group;

wherein L is selected from Formulas II, III or IV, as described above; and wherein B is hydrogen, a natural nucleobase, a modified nucleobase or a universal nucleobase.

In some embodiments, L is represented by Formula II, as described previously. In some embodiments, L is represented by Formula IIa, as described previously.

In other embodiments, L is represented by Formula III, as described previously. In some embodiments, Formula III is selected from Formula IIIa, IIIa(i), IIIb, or IIIb(i), as described previously.

In yet other embodiments, L is represented by Formula IV, as described previously. In some embodiments, Formula IV is selected from Formula IVa, IVb, IVc, IVd, or IVe, as described previously. In some embodiments, Formula IV is selected from Formula IVa(i), IVb(i), IVb(ii), IVc(i), or IVd(i), as described previously. In some embodiments, Formula IVe is selected from Formula IVe(i), IVe(ii), IVe(iii), IVe(iv), IVe(v), IVe(vi), IVe(vii), IVe(viii), IVe(ix), IVe(x), or IVe(xi), as described previously.

C. Protecting Groups

In some embodiments of the glutathione-sensitive nucleotides or nucleosides, a protecting group is attached to B, i.e., the natural, modified or universal nucleobase. Suitable protecting groups for B include acetyl, difluoroacetyl, trifluoroacetyl, isobutyryl, benzoyl, 9-fluorenylmethoxycarbonyl, phenoxyacetyl, dimethylformamidine, dibutylforamidine and N, N diphenyl carbamate.

In some embodiments, a protecting group is attached to a hydroxyl group in the nucleosides described above, particularly for the nucleoside phosphoramidites. Suitable protecting groups for the hydroxyl groups of the above-described nucleosides include any protecting group that is compatible with solid phase oligonucleotide synthesis, including, but not limited to, dimethoxytrityl, monomethoxytrityl, and/or trityl groups. A typical example is 4,4'-dimethoxytriphenylmethyl (DMTr) group, which may be readily cleaved under acidic conditions (e.g. in the presence of dichlroacetic acid (DCA), trichloroacetic acid (TCA), trifluoracetic acid (TFA) or acetic acid).

Other typical hydroxyl protecting groups include trialkyl silyl groups, such as tertbutyldimethylsilyl (TBDMS). The TBDMS group is stable under the acidic conditions used to remove the DMT group during the synthesis cycle, but can be removed by a variety of methods after cleavage and deprotection of the RNA oligomer, e.g., with a solution of tetrabutylammonium fluoride (TBAF) in tetrahydrofurane (THF) or with triethylamine hydrofluoride. Other typical hydroxyl protecting groups include tert-butyldiphenylsilyl ether (TBDPS), which may be removed with ammonium fluoride, for example.

IV. NUCLEOBASES

In the glutathione-sensitive oligonucleotides, nucleotides, and nucleosides described above, B represents a natural nucleobase, a modified nucleobase or a universal nucleobase.

Suitable natural nucleobases include purine and pyrimidine bases, e.g. adenine (A), thymine (T), cytosine (C), guanine (G), or uracil (U).

Suitable modified nucleobases include diaminopurine and its derivatives, alkylated purines or pyrimidines, acylated purines or pyrimidines thiolated purines or pyrimidines, and the like.

Other suitable modified nucleobases include analogs of purines and pyrimidines. Suitable analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, hypoxanthine, xanthine, 2-aminopurine, 6-hydroxyaminopurine, nitropyrrolyl, nitroindolyl and difluorotolyl, 6-thiopurine and 2,6-diaminopurine nitropyrrolyl, nitroindolyl and difluorotolyl.

Typically a nucleobase contains a nitrogenous base. In certain embodiments, the nucleobase does not contain a nitrogen atom. See e.g., U.S. Published Patent Application No. 20080274462.

A universal nucleobase refers to a base that can pair with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. The universal nucleobase may base pair by forming hydrogen bonds via Watson-Crick or non-Watson-Crick interactions (e.g., Hoogsteen interactions). Representative universal nucleobases include inosine and its derivatives.

V. OTHER SUBSTITUENTS IN FORMULAS I-XII

In Formulas I-XII, as appropriate, suitable aliphatic groups typically contain between about 2 and about 10 carbon atoms, more typically between about 2 and about 6 carbon atoms, such as between about 2 and about 5 carbon atoms.

In Formulas I-XII, as appropriate, suitable alkyl groups typically contain between about 1 and about 10 carbon atoms, more typically between about 2 and about 6 carbon atoms, such as between about 2 and about 5 carbon atoms.

In Formulas I-XII, as appropriate, suitable alkoxy groups include methoxy, ethoxy, propoxy, isopropoxy, n-butoxy, tert-butoxy, neopentoxy and n-hexoxy and the like.

In Formulas I-XII, as appropriate, suitable cycloalkyls include cyclopropyl, cyclobutyl, cyclopentyl, cyclohexyl, cycloheptyl and the like.

In Formulas I-XII, as appropriate, suitable heteroatoms include oxygen, sulfur, and nitrogen. Representative heterocycles include pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. Representative heteroaryls include furanyl, thienyl, pyridyl, pyrrolyl, N-lower alkyl pyrrolo, pyrimidyl, pyrazinyl, imidazolyl.

In Formulas I-XII, as appropriate, suitable alkenyl groups include vinyl, allyl, and 2-methyl-3-heptene and suitable alkynyl groups include propyne, and 3-hexyne.

In Formulas I-XII, as appropriate, suitable aryl groups include phenyl, naphthyl and the like, while suitable heteroaryl groups include pyridyl, furanyl, imidazolyl, benzimidazolyl, pyrimidinyl, thiophenyl or thienyl, quinolinyl, indolyl, thiazolyl, and the like.

In Formulas I-XII, as appropriate, suitable alkylaminos include —$CH_2CH_2CH_2NH$— or $CH_2CH_2NH$—.

VI. METHODS OF SYNTHESIZING OLIGONUCLEOTIDES

As discussed above, this application discloses nucleosides comprising a glutathione-sensitive moiety that are compatible with standard, phosphoramidite-based oligonucleotide synthesis methods.

The glutathione-sensitive oligonucleotides described in this application can be made using a variety of synthetic methods known in the art, including standard phosphoramidite methods. Any phosphoramidite synthesis method can be used to synthesize the glutathione-sensitive oligonucleotides of this invention. In certain embodiments, phosphoramidites are used in a solid phase synthesis method to yield reactive intermediate phosphite compounds, which are subsequently oxidized using known methods to produce glutathione-sensitive oligonucleotides, typically with a phosphodiester or phosphorothioate internucleotide linkages. The oligonucleotide synthesis of the present disclosure can be performed in either direction: from 5' to 3' or from 3' to 5' using art known methods.

Thus, in another aspect, the present disclosure relates to methods of synthesizing oligonucleotides using a glutathione-sensitive nucleoside phosphoramidite, such as those discussed above and represented, for example by Formulas VIII, IX, or X. Typically, the glutathione-sensitive moiety is located at the 2'-carbon of a ribose or deoxyribose (or analog thereof) and comprises a sulfonyl group or a disulfide bridge, including, for example, the glutathione-sensitive moieties represented by Formulas II, III, and IV. In certain embodiments, the method for synthesizing an oligonucleotide comprises (a) attaching a nucleoside to a solid support via a covalent linkage; (b) coupling a nucleoside phosphoramidite to a reactive hydroxyl group on the nucleoside of step (a) to form an internucleotide bond therebetween, wherein any uncoupled nucleoside on the solid support is capped with a capping reagent; (c) oxidizing said internucleotide bond with an oxidizing agent; and (d) repeating steps (b) to (c) iteratively with subsequent nucleoside phosphoramidites to form an oligonucleotide, wherein at least the nucleoside of step (a), the nucleoside phosphoramidite of step (b) or at least one of the subsequent nucleoside phosphoramidites of step (d) comprises a glutathione-sensitive moiety as described herein. Typically, the coupling, capping/oxidizing steps and optionally, deprotecting steps, are repeated until the oligonucleotide reaches the desired length and/or sequence, after which it is cleaved from the solid support.

In certain aspects, the oligonucleotide comprises at least one nucleotide having a glutathione-sensitive moiety and is prepared by a phosphoramidite-based oligonucleotide synthesis method using a nucleoside phosphoramidite that comprises at least one glutathione-sensitive moiety. In certain embodiments, the oligonucleotide is prepared by a method comprising (a) attaching a nucleoside to a solid support via a covalent linkage; (b) coupling a nucleoside phosphoramidite to a reactive hydroxyl group on the nucleoside of step (a) to form an internucleotide bond therebetween, wherein any uncoupled nucleoside on the solid support is capped with a capping reagent; (c) oxidizing said internucleotide bond with an oxidizing agent; (d) repeating steps (b) to (c) iteratively with subsequent nucleoside phosphoramidites to form an oligonucleotide; and (e) optionally cleaving the oligonucleotide from the solid support, wherein at least the nucleoside of step (a), the nucleoside phosphoramidite of step (b) or at least one of the subsequent nucleoside phosphoramadites of step (d) comprises a glutathione-sensitive moiety.

VI. PHARMACEUTICAL COMPOSITIONS

The present disclosure provides pharmaceutical compositions comprising a glutathione-sensitive oligonucleotide or a glutathione-sensitive nucleoside or nucleotide and a pharmaceutically acceptable excipient.

In some embodiments, the pharmaceutical composition comprises a pharmaceutically acceptable excipient and a therapeutically effective amount of a nucleic acid inhibitor molecule, wherein the nucleic acid inhibitor molecule comprises at least one nucleotide comprising a glutathione-sensitive moiety, as described herein. As described elsewhere, the glutathione-sensitive moiety is typically located at the 2'-carbon of the sugar moiety of the nucleotide and typically comprises a sulfonyl group or a disulfide bridge, including, such as the glutathione-sensitive moieties represented by Formulas II, III, or IV, as described previously.

In some embodiments, the pharmaceutical composition comprises a pharmaceutically acceptable excipient and a therapeutically effective amount of a nucleic acid inhibitor molecule, wherein the nucleic acid inhibitor molecule comprises at least one glutathione-sensitive nucleotide represented by Formula I, V, VI, or VII, as described previously.

In other embodiments, the pharmaceutical composition comprises a pharmaceutically acceptable excipient and a therapeutically effective amount of a glutathione-sensitive nucleoside or nucleotide, as represented, for example, by Formulas XI and XII, as described previously.

A. Pharmaceutically-Acceptable Excipients

The pharmaceutically-acceptable excipients useful in this disclosure are conventional. Remington's Pharmaceutical Sciences, by E. W. Martin, Mack Publishing Co., Easton, PA, 15$^{th}$ Edition (1975), describes compositions and formulations suitable for pharmaceutical delivery of one or more therapeutic compositions. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; malt; gelatin; excipients, such as cocoa butter and suppository waxes; oils, such as peanut oil, cottonseed oil, safflower oil, sesame oil, olive oil, corn oil and soybean oil; buffering agents, such as magnesium hydroxide and aluminum hydroxide; (isotonic saline; Ringer's solution); ethyl alcohol; pH buffered solutions; polyols, such as glycerol, propylene glycol, polyethylene glycol, and the like; and other non-toxic compatible substances employed in pharmaceutical formulations.

B. Dosage Forms

The pharmaceutical compositions may be formulated with conventional excipients for any intended route of administration, which may be selected according to ordinary practice.

In one embodiment, the pharmaceutical composition contains a glutathione-sensitive oligonucleotide or glutathione-sensitive nucleotide or nucleoside, as described herein, and is suitable for parenteral administration. Typically, the pharmaceutical compositions of the present disclosure that contain oligonucleotides are formulated in liquid form for parenteral administration, for example, by subcutaneous, intramuscular, intravenous or epidural injection. Dosage forms suitable for parenteral administration typically include one or more suitable vehicles for parenteral administration including, by way of example, sterile aqueous solutions, saline, low molecular weight alcohols such as propylene glycol, polyethylene glycol, vegetable oils, gelatin, fatty acid esters such as ethyl oleate, and the like. The parenteral formulations may contain sugars, alcohols, antioxidants, buffers, bacteriostats, solutes which render the formulation isotonic with the blood of the intended recipient or suspending or thickening agents. Proper fluidity can be maintained, for example, by the use of surfactants. Liquid formulations can be lyophilized and stored for later use upon reconstitution with a sterile injectable solution.

In another embodiment, the pharmaceutical composition contains a glutathione-sensitive oligonucleotide or glutathione-sensitive nucleotide or nucleoside, as described herein, and is suitable for oral administration. Typically, the pharmaceutical compositions of the present disclosure that contain nucleotides or nucleosides are formulated for oral administration. Suitable pharmaceutical compositions for oral administration may be in the form of capsules, tablets, pills, lozenges, cachets, dragees, powders, granules and the like.

The pharmaceutical compositions may also be formulated for other routes of administration including topical or transdermal administration, rectal or vaginal administration, ocular administration, nasal administration, buccal administration, or sublingual administration using well known techniques.

C. Delivery Agents

The glutathione-sensitive nucleic acid inhibitor molecule, nucleotide, or nucleoside may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the glutathione-sensitive nucleic acid inhibitor molecule, nucleotide, or nucleoside is formulated in a lipid nanoparticle (LNP). Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as LIPEX® Extruder (Northern Lipids, Inc). To prepare a lipid nanoparticle for therapeutic use, it may be desirable to remove solvent (e.g., ethanol) used to form the nanoparticle and/or exchange buffer, which can be accomplished by, for example, dialysis or tangential flow filtration. Methods of making lipid nanoparticles containing nucleic acid interference molecules are known in the art, as disclosed, for example in U.S. Published Patent Application Nos. 2015/0374842 and 2014/0107178.

In certain embodiments, the LNP comprises a lipid core comprising a cationic lipid and a pegylated lipid. The LNP can further comprise one or more envelope lipids, such as a cationic lipid, a structural or neutral lipid, a sterol, a pegylated lipid, or mixtures thereof.

In certain embodiments, an oligonucleotide of the invention is covalently conjugated to a ligand that directs delivery of the oligonucleotide to a tissue of interest. Many such ligands have been explored. See, e.g., Winkler, Ther. Deliv., 4(7): 791-809 (2013). For example, an oligonucleotide of the invention can be conjugated to multiple sugar ligand moieties (e.g., N-acetylgalactosamine (GalNAc)) to direct uptake of the oligonucleotide into the liver. See, e.g., WO 2016/100401. Other ligands that can be used include, but are not limited to, mannose-6-phosphate, cholesterol, folate, transferrin, and galactose (for other specific exemplary ligands see, e.g., WO 2012/089352). Typically, when an oligonucleotide is conjugated to a ligand, the oligonucleotide is administered as a naked oligonucleotide, wherein the oligonucleotide is not also formulated in an LNP or other protective coating. In certain embodiments, the naked oligonucleotide contains at least one nucleotide having a glutathione-sensitive moiety, with the 2'-position of the sugar moiety of the remaining nucleotides of the naked oligonucleotide modified, typically with 2'-F or 2'-OMe.

These pharmaceutical compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The pharmaceutical compositions in solid form may be packaged in multiple single dose units, each containing a fixed amount of the above mentioned agent or agents, such as in a sealed package of tablets or capsules. The pharmaceutical compositions in solid form can also be packaged in a container for a flexible quantity, such as in a squeezable tube designed for a topically applicable cream or ointment.

The pharmaceutical compositions of the present disclosure are applied for therapeutic use. Thus, one aspect of the disclosure provides a pharmaceutical composition, which may be used to treat a subject including, but not limited to, a human suffering from a disease or a condition by administering to said subject an effective amount of a pharmaceutical composition of the present disclosure.

In certain embodiments, the present disclosure features the use of a therapeutically effective amount of a pharmaceutical composition as described herein for the manufacture of a medicament for treatment of a patient in need thereof.

VIII. METHODS OF ADMINISTRATION/TREATMENT

The pharmaceutical compositions described herein are typically administered orally or parenterally. Pharmaceutical compositions containing the glutathione-sensitive nucleic acid inhibitor molecules of the invention are typically administered intravenously or subcutaneously. Pharmaceutical compositions containing the glutathione-sensitive nucleotides or nucleosides of the invention are typically administered orally. However, the pharmaceutical compositions disclosed herein may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the pharmaceutical compositions disclosed herein may be useful for the treatment or prevention of symptoms related to a viral infection in a patient in need thereof. One embodiment is directed to a method of treating a viral infection, comprising administering to a subject a pharmaceutical composition comprising a therapeutically effective amount of a glutathione-sensitive nucleic acid inhibitor molecule, nucleotide, or nucleoside, as described herein. In certain embodiments, the pharmaceutical composition comprises a glutathione-sensitive nucleoside or nucleotide, as represented, for example, by Formulas XI and XII, as described previously. Non-limiting examples of such viral infections include HCV, HBV, HPV, HSV or HIV infection.

In certain embodiments, the pharmaceutical compositions disclosed herein may be useful for the treatment or prevention of symptoms related to cancer in a patient in need thereof. One embodiment is directed to a method of treating cancer, comprising administering to a subject a pharmaceutical composition comprising a therapeutically effective amount of a glutathione-sensitive nucleic acid inhibitor molecule, as described herein. Non-limiting examples of such cancers include bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T-cell lymphomas, non-Hodgkin lymphoma, precursor T-lymphoblastic lymphoma/leukemia, peripheral T-cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Typically, the present disclosure features methods of treating liver cancer, liver carcinoma, hepatoma, hepatocellular carcinoma, cholangiocarcinoma and hepatoblastoma by administering a therapeutically effective amount of a pharmaceutical composition as described herein.

In certain embodiments the pharmaceutical compositions disclosed herein may be useful for treatment or prevention of symptoms related to proliferative, inflammatory, autoimmune, neurologic, ocular, respiratory, metabolic, dermatological, auditory, liver, kidney, or infectious diseases. One embodiment is directed to a method of treating a proliferative, inflammatory, autoimmune, neurologic, ocular, respiratory, metabolic, dermatological, auditory, liver, kidney, or infectious disease, comprising administering to a subject a pharmaceutical composition comprising a therapeutically effective amount of a glutathione-sensitive nucleic acid inhibitor molecule, as described herein. Typically, the disease or condition is disease of the liver.

In some embodiments, the present disclosure provides a method for reducing expression of a target gene in a subject comprising administering a pharmaceutical composition to a subject in need thereof in an amount sufficient to reduce expression of the target gene, wherein the pharmaceutical composition comprises a glutathione-sensitive nucleic acid inhibitor molecule as described herein and a pharmaceutically acceptable excipient as also described herein.

In some embodiments, the glutathione-sensitive nucleic acid inhibitor molecule is an RNAi inhibitor molecule as described herein, including a ssRNAi inhibitor molecule or a dsRNAi inhibitor molecule.

The target gene may be a target gene from any mammal, such as a human target gene. Any gene may be silenced according to the instant method. Exemplary target genes include, but are not limited to, Factor VII, Eg5, PCSK9, TPX2, apoB, SAA, TTR, HBV, HCV, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, LDHA, and combinations thereof.

In some embodiments the glutathione-sensitive nucleic acid inhibitor molecule silences a target gene and thus can be used to treat a subject having or at risk for a disorder characterized by unwanted expression of the target gene. For example, in some embodiments, the present glutathione-sensitive nucleic acid inhibitor molecule silences the beta-catenin gene, and thus can be used to treat a subject having or at risk for a disorder characterized by unwanted beta-catenin expression, e.g., adenocarcinoma or hepatocellular carcinoma.

In certain embodiments, the pharmaceutical composition is delivered via systemic administration (such as via intravenous or subcutaneous administration) to relevant tissues or cells in a subject or organism, such as the liver. In other embodiments, the pharmaceutical composition is delivered via local administration or systemic administration. In certain embodiments, the pharmaceutical composition is delivered via local administration to relevant tissues or cells, such as lung cells and tissues, such as via pulmonary delivery.

The therapeutically effective amount of the compounds disclosed herein may depend on the route of administration and the physical characteristics of the patient, such as the size and weight of the subject, the extent of the disease progression or penetration, the age, health, and sex of the subject. As used herein, a therapeutically effective amount means an amount of compound or compounds effective to prevent, alleviate or ameliorate disease or condition symptoms of the subject being treated.

In certain embodiments, the glutathione-sensitive oligonucleotide, nucleotide or nucleoside is administered at a dosage of 20 micrograms to 10 milligrams per kilogram body weight of the recipient per day, 100 micrograms to 5 milligrams per kilogram, 0.25 milligrams to 2.0 milligrams per kilogram, or 0.5 to 2.0 milligrams per kilogram.

A pharmaceutical composition of the instant disclosure may be administered every day, or intermittently. For example, intermittent administration of a compound of the instant disclosure may be administration one to six days per week, one to six days per month, once weekly, once every other week, once monthly, once every other month, or once or twice per year or divided into multiple yearly, monthly, weekly, or daily doses. In some embodiments, intermittent dosing may mean administration in cycles (e.g. daily administration for one day, one week or two to eight consecutive weeks, then a rest period with no administration for up to one week, up to one month, up to two months, up to three months or up to six months or more) or it may mean administration on alternate days, weeks, months or years.

In any of the methods of treatment of the invention, the compounds may be administered to the subject alone as a monotherapy or in combination with additional therapies known in the art.

EXAMPLES

Example 1. Synthesis of Glutathione-Sensitive Compounds

All non-hydrolytic reactions, unless indicated otherwise, were carried out in dry solvents purchased from Sigma-Aldrich Corporation (St. Louis, MO). High Performance Liquid Chromatography (HPLC), except for the amidites, was performed at 60° C. using an Agilent ZORBAX® Eclipse Plus (Agilent Technologies Company, Santa Clara, CA) C18, 21×50 millimeter (mm), 1.8 micron column, 100×4.6 mm, 2.7 micron column with ammonium formate (3 millmolar) as a modifier under otherwise identical conditions. UV traces were recorded at 220 nanometer (nm) and mass spectra were obtained using an Agilent Technologies 6140 Quadrapole LC/MS mass spectrometer in both positive and negative ion mode. Preparative purifications were performed by gradient chromatography on a Teledyne Isco COMBIFLASH® Rf using pre-packed columns (Teledyne Isco, Inc., Lincoln, NE). NMR spectra were recorded on a Varian UNITY® 600, 500 or 400 spectrometers, Varian, Inc. (Palo Alto, CA).

Compound 8b

The below scheme 1 depicts the synthesis of a glutathione-sensitive compound comprising a disulfide bridge: (2R,3R,4R,5R)-5-((bis(4-methoxyphenyl)(phenyl) methoxy)methyl)-4-(((2 cyanoethyl)(diisopropylamino) phosphino)oxy)-2-(2,4-dioxo-3,4-dihydropyrimidin-1(2H)-yl)tetrahydrofuran-3-yl (2-(tert-butyldisulfanyl)phenyl) carbamate (Compound 8b). The glutathione-sensitive moiety of Compound 8b is encompassed by Formula IVe and more specifically is represented by Formula IVe(ix). To demonstrate the feasibility of preparing this compound, a simple model oligomer with eight nucleotides was synthesized. The key intermediate, phosphoramidite 8b, was synthesized according to the procedure shown in the scheme below. In brief, commercially available tert butyl thiol was converted to activated thiosulfonate 2b, which was subsequently reacted with 2-aminothiophenol to obtain disulfide compound 4b. The 4b compound was next treated with triphosgene generated isocyanate intermediate 5b. Without prior isolation, the isocyante 5b compound was "in-situ reacted with 5'-dimethoxytrityl (DMtr)-protected uridine to afford a mixture of 2',3'-protected carbamates. We observed migration of carbamate from the 2'- to the 3'-position during chromatography purification. To avoid this undesired migration, a 1% pyridine solution was used during silica gel purification. After separation of the undesired isomers, compound 7b was subjected to phosphitylation conditions, as typically used with synthesized phosphoramidite. Compound 8b was then purified by silica gel column chromatography as commonly used during the purification of standard cyanoethyl group-containing phosphoramidites. Compound 8b exhibited similar physiochemical behavior, including stability, to standard phosphoramidite compounds.

Scheme 1

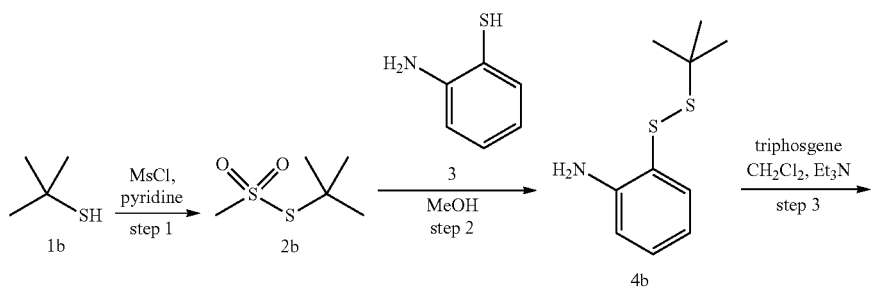

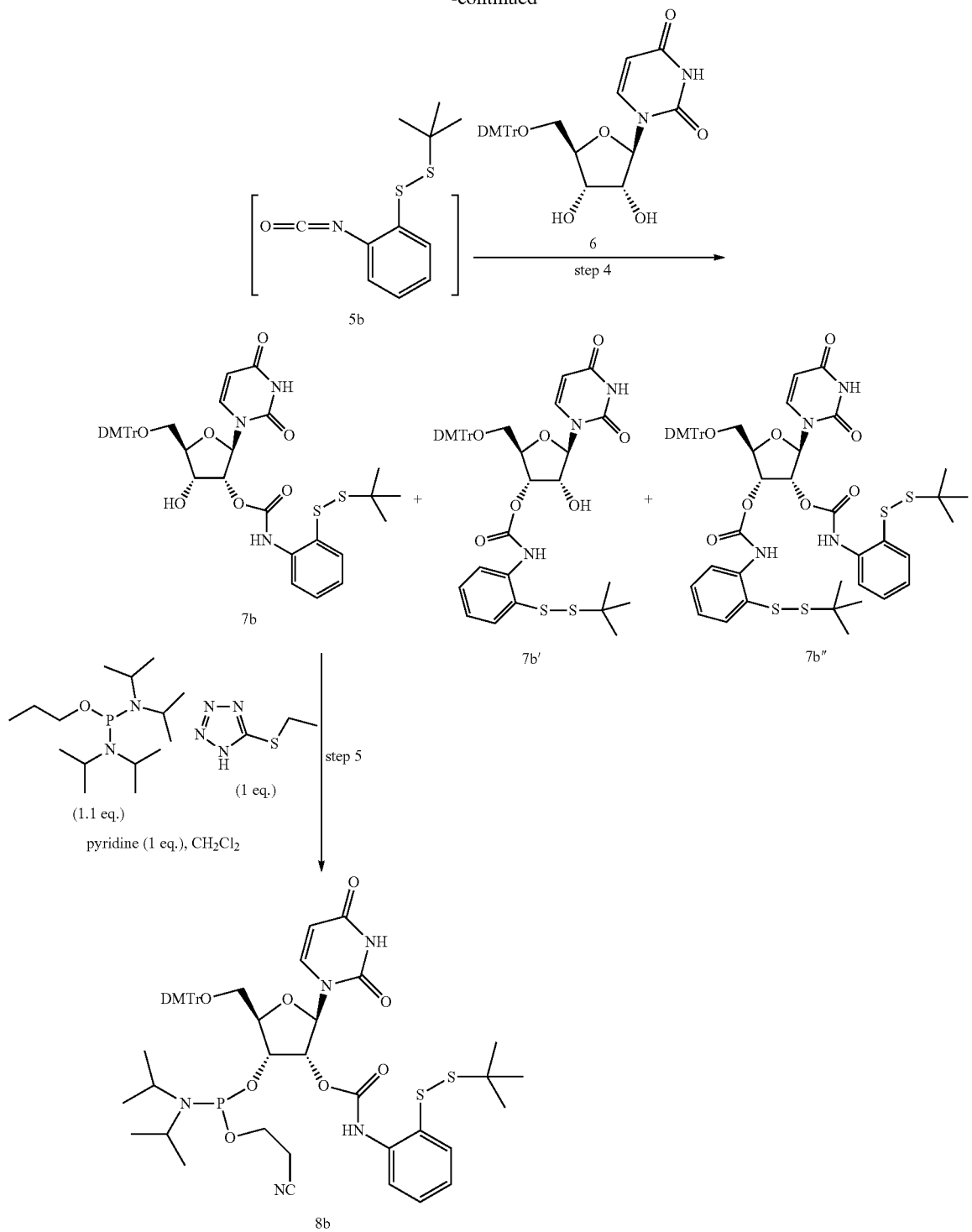

Synthesis of S-tert-butyl methanesulfonothioate (2b)

To a solution of tert-butylthiol (1b) (20 grams (g)), 0.22 mole (mol), 1 equivalent (equiv.) aldehyde (Ald.)) in dry pyridine (100 mL, Ald. anhydrous) was dropwise added methanesulfonyl chloride (17.1 milliliter (mL), 0.22 mol, Ald.). The reaction was stirred at room temperature and monitored by Thin Layer Chromatography (TLC): hexane: EtOAc=6:1; visualized with phosphomolybdic acid (PMA), Retardation factor (Rf)=0.44. After overnight, the reaction was complete and the reaction was diluted with $Et_2O$, then acidified with 4N HCl. The aqueous phase was extracted with $Et_2O$, separated and dried over anhydrous $Na_2SO_4$. After concentrating with a Rotary Evaporator (rotavap), the crude product was purified by ISCO chromatography (ISCO REDISEP® (Teledyne Isco, Inc), 330 g) and eluted with 0% to 100% of EtOAc in hexane (monitored by UV: 254 nm, 280 nm). The desired fractions were combined and evaporated to give a colorless oil of 2b (20 g, 53%); Proton nuclear magnetic resonance (1H NMR) (300 megahertz (MHz), chloroform-d (CDCl3) spectrum is as follows: 3.33 (s, 3H), 1.58 (s, 9H)).

Synthesis of 2-(tert-butyldisulfanyl)aniline (4b)

To a solution of ortho-aminobenzenethiol (3)(12.8 mL, 0.12 mol, 1 equiv. Acros) in MeOH (200 mL, Ald. anhydrous) was added S-tert-butyl methanesulfonothioate 2b (20 g, 0.12 mol, 1 equiv.) and the reaction was stirred at room temperature under $N_2$. The reaction was monitored by TLC & mass spectrometry (MS): hexane:EtOAc=6:1; visualized with PMA, Rf=0.68; MS atmospheric pressure chemical ionization (APCI) [M+1]: 214.0 (100%). After 2 h, the reaction was complete and concentrated by rotavap. The crude product was purified by ISCO chromatography (ISCO REDISEP®, 330 g) and eluted with 0% to 100% of EtOAc in hexane (monitored by UV: 254 nm, 280 nm). The desired fractions were combined and evaporated to give a colorless oil of 4b (25 g, 98%). 1H NMR (300 MHz, CDCl3) spectrum is as follows: 7.50 (dd, J=7.68, 1.38 Hz, 1H), 7.09 (td, J=7.41, 1.38 Hz, 1H), 6.67 (m, 2H), 1.34 (s, 9H). MS: (APCI+) M+1=214.0.

Synthesis of 1-(tert-butyl)-2-(2-isocyanatophenyl)disulfane (5b)

Under 0° C. ice-water bath, to a solution of 2-(tert-butyldisulfanyl)aniline (4b) (10 g, 46.8 mmol, 1 equiv.) in $CH_2Cl_2$ (500 mL, Ald. anhydrous) was added triphosgene (13.9 g, 46.8 mmol, 1 equiv., Acros), followed by the addition of $Et_3N$ (65.3 mL, 0.46 mol, 10 equiv., Ald. anhydrous) and the reaction was stirred at 0° C. for 1 h. The reaction was concentrated by rotavap (water bath: room temp.) and the obtained crude solid was used in the next step directly.

Synthesis of (2R,3R,4R,5R)-5-((bis(4-methoxyphenyl)(phenyl)methoxy)methyl)-2-(2,4-dioxo-3,4-dihydropyrimidin-1(2H)-yl)-4-hydroxytetrahydrofuran-3-yl (2-(tert-butyldisulfanyl)phenyl)carbamate (7b)

Under 0° C. ice-water bath, to a solution of crude 1-(tert-butyl)-2-(2-isocyanatophenyl)disulfane (5b) (crude, 2 equiv.) in $CH_2Cl_2$ (500 mL, Ald. anhydrous) was added 1-((2R,3R,4S,5R)-5-((bis(4-methoxyphenyl)(phenyl)methoxy)methyl)-3,4-dihydroxytetrahydrofuran-2-yl)pyrimidine-2,4(1H,3H)-dione 6 (13 g, 23.78 mmol, 1 equiv, carbosynth) and the reaction was stirred for 1.5 h, allowing 0° C. to room temperature. The reaction was monitored by TLC, hexane:EtOAc=1:2; visualize with PMA. TLC showed the product 7b (Rf=0.38) as well as 7b' (regioisomer, Rf=0.19) and 7b" (dicarbamate, Rf=0.61). After 1.5 h, the reaction was concentrated and mixed with EtOAc (100 mL) and the insoluble salt was filtered. The filtrate was diluted with EtOAc (500 mL), washed with saturated $NaHCO_3$, $H_2O$, Brine and dried over anhydrous $Na_2SO_4$. After concentration by rotavap, the crude product was loaded onto a pre-equilibrated silica-gel column and purified by ISCO chromatography (ISCO REDISEP®, 120 g, pre-equilibrated with 0.5% pyridine/Hexane)[1], and eluted with 0% to 100% of EtOAc in hexane (monitored by UV: 254 nm, 280 nm). The desired fractions were combined and evaporated to give a colorless foam 2.6 g of 7b (14%) with the purity of 94% (HPLC). 1H NMR (300 MHz, DMSO-d6) spectrum is as follows: 11.42 (s, 1H), 9.38 (s, 1H), 7.72 (m, 2H), 7.24-7.38 (m, 13H), 6.88-6.91 (m, 4H), 6.01 (d, J=4.95 Hz, 1H), 5.70 (d, J=5.79 Hz, 1H), 5.37 (dd, J=7.95, 2.19 Hz, 1H), 5.30 (t, J=3.09 Hz, 1H), 4.41 (dd, J=11.01, 5.49 Hz, 1H), 3.73 (s, 6H), 3.21-3.30 (m, 2H), 1.21 (s, 9H). MS: (APCI−) M−1=784.2.

(Step 5): Synthesis of (2R,3R,4R,5R)-5-((bis(4-methoxyphenyl)(phenyl)methoxy)methyl)-4-(((2-cyanoethyl)(diisopropylamino)phosphino)oxy)-2-(2,4-dioxo-3,4-dihydropyrimidin-1(2H)-yl)tetrahydrofuran-3-yl (2-(tert-butyldisulfanyl)phenyl)carbamate (8b)

To a solution of (2R,3R,4R,5R)-5-((bis(4-methoxyphenyl)(phenyl)methoxy)methyl)-2-(2,4-dioxo-3,4-dihydropyrimidin-1(2H)-yl)-4-hydroxytetrahydrofuran-3-yl (2-(tert-butyldisulfanyl)phenyl)carbamate (7b) (1.6 g, 2.03 mmol, 1 equiv.) in $CH_2Cl_2$ (40 mL, Ald. anhydrous) was added pyridine (0.16 mL, 2.03 mmol, 1 equiv, Ald. Anhydrous) and 5-(ethylthio)-1H-tetrazole (265 mg, 2.03 mmol, 1 equiv, Ald.) at room temperature under $N_2$. Then O-cyanoethyl-N,N,N',N'-tetraisopropyl phospharodiamidite (674.9 mg, 2.23 mmol, 1.1 equiv, ChemGenes Corporation, Wilmington, MA) was added. The reaction was stirred at room temp and monitored by TLC: hexane:EtOAc=1:2; visualize with PMA, Rf=0.51. After 2 h, the reaction was complete and the reaction was diluted with $CH_2Cl_2$ (400 mL) and washed with saturated (sat.) $NaHCO_3$, $H_2O$, Brine and dried over anhydrous $Na_2SO_4$. After concentration by rotavap, the crude product was loaded onto a pre-equilibrated silica-gel column and purified by ISCO chromatography (ISCO REDISEP®, 40 g, pre-equilibrated with 1.0% $Et_3N$ in hexane), and eluted with 0% to 100% of EtOAc in hexane (1% $Et_3N$) (monitored by UV: 254 nm, 280 nm). The desired fractions were combined and evaporated to give a colorless foam 1.6 g of 8b (77%) with the purity of 97% (HPLC). 1H NMR (300 MHz, DMSO-d6) spectrum is as follows: 11.47 (s, 1H), 9.45 (m, 1H), 7.74 (m, 2H), 7.25-7.38 (m, 13H), 6.87-6.90 (m, 4H), 6.02 (m, 1H), 5.40-5.49 (m, 2H), 4.62 (m, 1H), 4.21 (m, 1H), 3.73 (s, 6H), 3.48-3.65 (m, 4H), 3.32 (m, 1H), 2.73 (m, 1H), 2.62 (t, J=6.3 Hz, 1H), 1.19 (s, 9H), 0.94-1.12 (m, 12H). 31P NMR (161 MHz, DMSO-d6) 150.44, 150.08. MS: (APCI−) M−1=984.4.

Compound 8d

The below scheme 3 depicts the synthesis of a glutathione-sensitive compound comprising a disulfide bridge: (2R,3R,4R,5R)-5-((bis(4-methoxyphenyl)(phenyl)methoxy)methyl)-4-(((2-cyanoethoxy)(diisopropylamino)phosphino)oxy)-2-(2,4-dioxo-3,4-dihydropyrimidin-1(2H)-yl)tetrahydrofuran-3-yl (2-((tert-butyldisulfanyl)methyl)phenyl)carbamate (Compound 8d). The glutathione-sensitive moiety of Compound 8d is encompassed by Formula IVe and more specifically is represented by Formula IVe(ii). The nucleoside phosphoramidite 8d was synthesized by following the analogous procedure described for the synthesis of 8b. Briefly, commercially available 2-amino benzyl alcohol was transiently protected with a Boc group to afford 1d-2. A Mitsunobu reaction of 1d-2 in the presence of thioacetic acid afforded the thioester intermediate 1d-2. Selective hydrolysis of the thioester with NaOMe/MeOH followed by treatment with S-tert-butyl methanesulfonothioate afforded the compound 3d. After Boc deprotection with trifluoracetic acid (TFA), 4d was converted to isocyanate intermediate 5d, and "in-situ" reacted with 5'-dimethoxytriphenylmethyl (DMTr)-protected uridine to afford mixture of 2'- and 3'-protected carbamates 7d and 7d'. After column chromatography separation, phosphitylation of 7d afforded the required phosphoramidite 8d as colorless foam in 50% yield.

Scheme 3
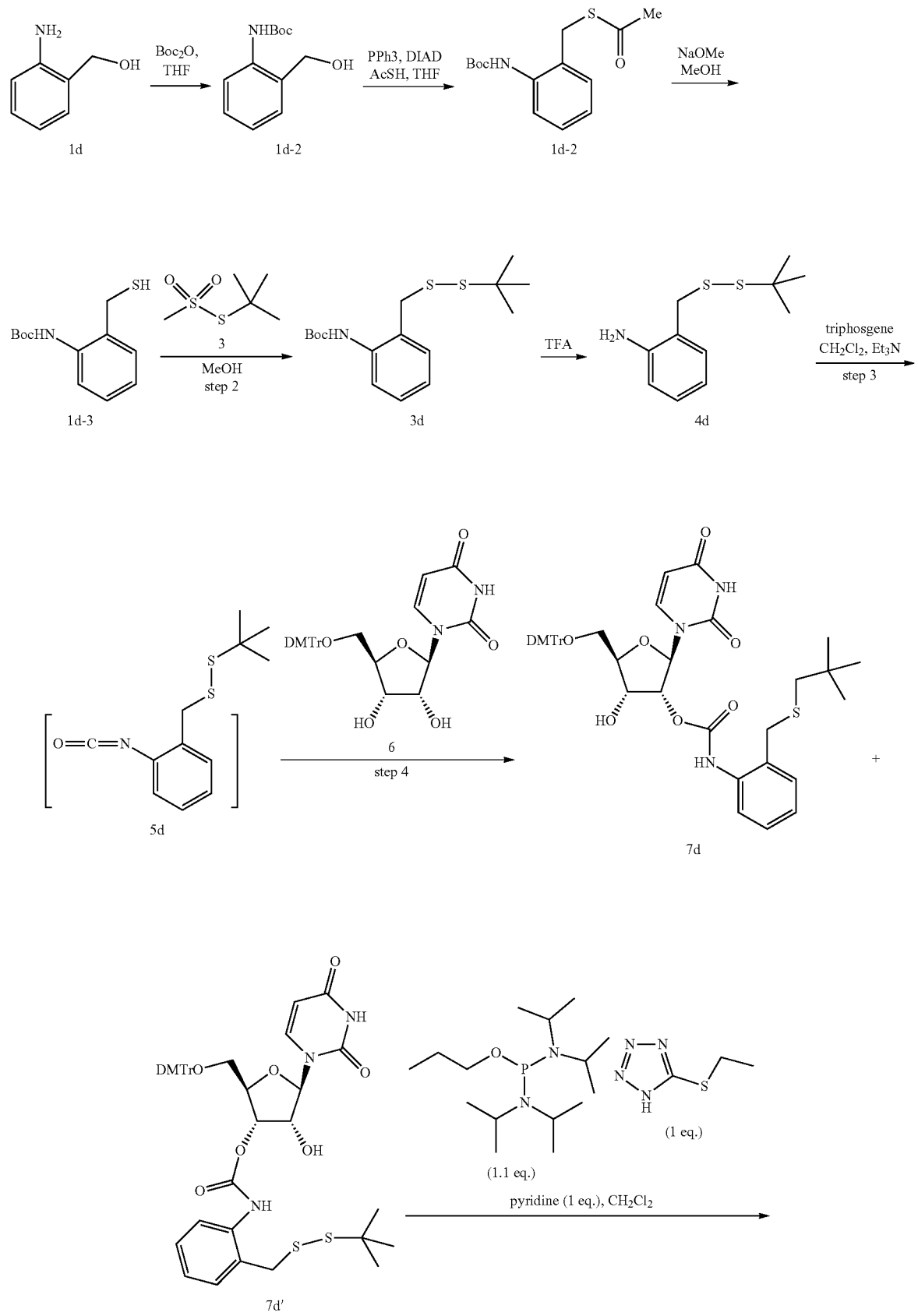

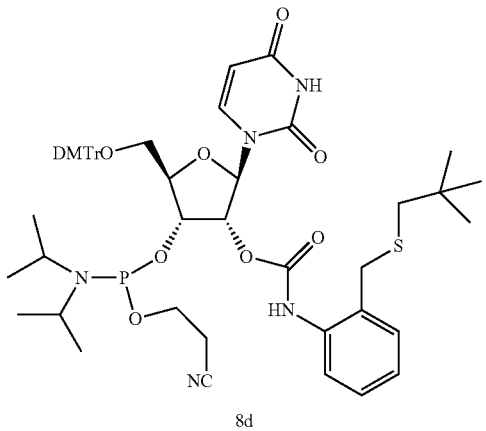

8d (Step 1): Synthesis of tert-butyl (2-(hydroxymethyl)phenyl)carbamate (1d-1)

To a solution of (2-aminophenyl)methanol (1d) (10 g, 81.2 mmol, 1 equiv. Ald.) in tetrahydrofuran (THF) (200 mL, Ald. anhydrous) was added Boc$_2$O (18.6 g, 85.2 mmol, 1.1 equiv. AK scientific). The reaction was stirred at room temperature and monitored by TLC: hexane:EtOAc=6:1, visualize with PMA, Rf=0.2. After overnight, the reaction was complete and the reaction was diluted with EtOAc (500 mL), washed with saturated NaHCO$_3$, H$_2$O, brine and dried over anhydrous Na$_2$SO$_4$. After concentration by rotavap, the crude product was purified by ISCO chromatography (ISCO REDISEP®, 220 g), and eluted with 0% to 100% of EtOAc in hexane (monitored by UV: 254 nm, 280 nm). The desired fractions were combined and evaporated to give a colorless foam 15 g of 1d-1 (82%). 1H NMR (300 MHz, CDCl3) spectrum is as follows: 7.90 (d, J=7.98 Hz, 1H), 7.61 (s, 1H), 7.30 (t, J=7.68 Hz, 1H), 7.16 (d, J=7.41 Hz, 1H), 7.00 (t, J=7.41 Hz, 1H), 4.68 (s, 2H), 1.51 (s, 9H).

(Step 2): Synthesis of S-2-((tert-butoxycarbonyl)amino)benzyl ethanethioate (1d-2)

To a solution of Ph$_3$P (23.6 g, 90.3 mmol, 2.1 equiv. Ald.) in THF (300 mL) was added diisopropyl azodicarboxylate (DIAD) (17.7 mL, 90.3 mmol, 2.1 equiv. Ald.) at 0° C. and the mixture was stirred for 30 min. A mixture of tert-butyl (2-(hydroxymethyl)phenyl)carbamate (1d-1) (9.6 g, 43 mmol, 1 equiv.) and thioacetic acid (6.3 mL, 90.3 mmol, 2.1 equiv. Ald.) in THF (100 mL) was added dropwise to the above reaction mixture. The reaction was stirred, allowing to warm to room temperature and was monitored by TLC: hexane:EtOAc=6:1, visualized with PMA, Rf=0.47. After overnight, the mixture was diluted with EtOAc (500 mL), washed with sat. NaHCO$_3$, H$_2$O, brine and dried over anhydrous Na$_2$SO$_4$. After concentration by rotavap, the crude product was purified by ISCO chromatography (ISCO REDISEP®, 220 g), and eluted with 0% to 100% of EtOAc in hexane (monitored by UV: 254 nm, 280 nm). The desired fractions were combined and evaporated to give a colorless foam 10 g of 1d-2 (88%). 1H NMR (300 MHz, DMSO-d6) spectrum is as follows: 8.64 (s, 1H), 7.19-7.30 (m, 3H), 7.05 (t, J=7.41 Hz, 1H), 4.10 (s, 2H), 2.28 (s, 3H), 1.41 (s, 9H).

(Step 3): Synthesis of tert-butyl (2-(mercaptomethyl)phenyl)carbamate (1d-3)

To a solution of S-2-((tert-butoxycarbonyl)amino)benzyl ethanethioate (1d-2) (11.8 g, 41.9 mmol, 1 equiv.) in MeOH (200 mL) was added NaOMe (2.2 g, 41.9 mmol, 1 equiv. Ald.) and the reaction was stirred at room temperature and was monitored by TLC: hexane:EtOAc=6:1, visualized with PMA, Rf=0.5. After 2 h, the reaction was complete and was acidified with 1N HCl to pH~6, then concentrated by rotavap. The crude product was dissolved in EtOAc (500 mL), washed with H$_2$O, brine and dried over anhydrous Na$_2$SO$_4$. After concentration, the crude product 1d-3 was used directly in the next step.

(Step 4): Synthesis of 2-((tert-butyldisulfanyl)methyl)aniline (3d)

To a solution of tert-butyl (2-(mercaptomethyl)phenyl)carbamate (1d-3)(10 g, 41.9 mmol, 1 equiv.) in MeOH (200 mL, Ald. anhydrous) was added S-tert-butyl methanesulfonothioate 2b (9.2 g, 54.5 mmol, 1.3 equiv.), followed by the addition of Et$_3$N (17.5 mL, 125.8 mmol, 3 equiv. Ald, anhydrous). The reaction was stirred at room temperature under N$_2$ and was monitored by TLC: hexane:EtOAc=6:1, visualize with PMA, Rf=0.6. After 2 h, the reaction was complete and concentrated by rotavap. The crude product was purified by ISCO chromatography (ISCO REDISEP®, 80 g) and eluted with 0% to 100% of EtOAc in hexane (monitored by UV: 254 nm, 280 nm). The desired fractions were combined and evaporated to give a white solid of 3d (5.8 g, 42%). 1H NMR (300 MHz, DMSO-d6) spectrum is as follows: 8.62 (s, 1H), 7.19-7.30 (m, 3H), 7.05 (t, J=7.41 Hz, 1H), 4.02 (s, 2H), 1.41 (s, 9H), 1.21 (s, 9H).

(Step 5): Synthesis of 2-((tert-butyldisulfanyl)methyl)aniline (4d)

2-((tert-butyldisulfanyl)methyl)aniline (3d) (3 g, 9.16 mmol, 1 equiv.) was added into a mixture solution of TFA/CH$_2$Cl$_2$ (15 mL/45 mL) and the reaction was stirred at room temperature for 2 hours. The reaction was concentrated by rotavap (water bath: room temperature) and the obtained crude product 4d was used directly in the next step.

(Step 6): Synthesis of 1-(tert-butyl)-2-(2-isocyanatobenzyl)disulfane (5d)

Under 0° C. ice-water bath, to a solution of 2-(((tert-butyldisulfanyl)methyl)aniline (4d) (crude, 2 g, 8.8 mmol, 1 equiv.) in $CH_2Cl_2$ (100 mL, Ald. anhydrous) was added triphosgene (2.6 g, 8.8 mmol, 1 equiv., Acros), followed by the addition of $Et_3N$ (12.3 mL, 0.09 mol, 10 equiv., Ald. anhydrous) and the reaction was stirred at 0° C. for 1 hour. The reaction was concentrated by rotavap (water bath: room temperature) and the obtained crude solid 5d was used in the next step directly.

(Step 7): Synthesis of (2R,3R,4R,5R)-5-((bis(4-methoxyphenyl)(phenyl)methoxy)methyl)-2-(2,4-dioxo-3,4-dihydropyrimidin-1(2H)-yl)-4-hydroxytetrahydrofuran-3-yl (2-((tert-butyldisulfanyl)methyl)phenyl)carbamate (7d)

Under 0° C. ice-water bath, to a solution of crude 1-(tert-butyl)-2-(2-isocyanatobenzyl)disulfane (5d) (crude, 2 equiv.) in $CH_2Cl_2$ (100 mL, Ald. anhydrous) was added 1-((2R,3R,4S,5R)-5-((bis(4-methoxyphenyl)(phenyl)methoxy)methyl)-3,4-dihydroxytetrahydrofuran-2-yl)pyrimidine-2,4(1H,3H)-dione 6 (2.4 g, 4.39 mmol, 1 equiv, carbosynth) and the reaction was stirred, allowing 0° C. to room temperature. The reaction was monitored by TLC, hexane:EtOAc=1:4, visualize with PMA. TLC showed the product 7d (Rf=0.35) as well as 7d' (regioisomer, Rf=0.18) and 7d" (dicarbamate, Rf=0.71). After overnight, the reaction was concentrated and mixed with EtOAc (100 mL) and the insoluble salt was filtered. The filtrate was diluted with EtOAc (500 mL), washed with sat. $NaHCO_3$, $H_2O$, brine and dried over anhydrous $Na_2SO_4$. After concentration by rotavap, the crude product was loaded onto a pre-equilibrated silica-gel column and purified by ISCO chromatography (ISCO REDISEP®, 80 g, pre-equilibrated with 0.5% pyridine/Hexane)[1], and eluted with 0% to 100% of EtOAc in hexane (monitored by UV: 254 nm, 280 nm). The desired fractions were combined and evaporated to give a colorless foam 339 mg of 7d (10%) with the purity of 79.3% (HPLC)[2,3]. 1H NMR (300 MHz, DMSO-d6) spectrum is as follows: 11.45 (s, 1H), 9.27 (s, 1H), 7.73 (d, J=8.25 Hz, 1H), 7.23-7.40 (m, 13H), 6.88-6.96 (m, 4H), 6.04 (d, J=4.65 Hz, 1H), 5.72 (d, J=5.49 Hz, 1H), 5.38 (d, J=7.98 Hz, 1H), 5.26 (t, J=5.22 Hz, 1H), 4.45 (dd, J=10.44, 5.22 Hz, 1H), 4.05 (m, 1H), 3.72 (s, 6H), 3.32 (m, 1H), 3.26 (m, 1H), 1.21 (s, 9H).

(Step 8): Synthesis of (2R,3R,4R,5R)-5-((bis(4-methoxyphenyl)(phenyl)methoxy)methyl)-4-(((2-cyanoethoxy)(diisopropylamino)phosphino)oxy)-2-(2,4-dioxo-3,4-dihydropyrimidin-1(2H)-yl)tetrahydrofuran-3-yl (2-((tert-butyldisulfanyl)methyl)phenyl)carbamate (8d)

To a solution of (2R,3R,4R,5R)-5-((bis(4-methoxyphenyl)(phenyl)methoxy)methyl)-2-(2,4-dioxo-3,4-dihydropyrimidin-1(2H)-yl)-4-hydroxytetrahydrofuran-3-yl (2-((tert-butyldisulfanyl)methyl)phenyl)carbamate (7d) (239 mg, 0.30 mmol, 1 equiv) in $CH_2Cl_2$ (10 mL, Ald. anhydrous) was added pyridine (0.02 mL, 0.30 mmol, 1 equiv, Ald. Anhydrous) and 5-(ethylthio)-1H-tetrazole (38.9 mg, 0.30 mmol, 1 equiv, Combi-Blocks) at room temperature under $N_2$[1]. Then O-cyanoethyl-N,N,N',N'-tetraisopropyl phospharodiamidite (99.1 mg, 0.33 mmol, 1.1 equiv, ChemGenes Corporation) was added. The reaction was stirred at room temperature and monitored by TLC: hexane:EtOAc=1:4, visualize with PMA, Rf=0.69. After 6 h, the reaction showed the expect product as the major spot and the reaction was diluted with $CH_2Cl_2$ (200 mL) and washed with sat. $NaHCO_3$, $H_2O$, brine and dried over anhydrous $Na_2SO_4$. After concentration by rotavap, the crude product was loaded onto a pre-equilibrated silica-gel column and purified by ISCO chromatography (ISCO REDISEP®, 24 g, pre-equilibrated with 1.0% $Et_3N$ in hexane), and eluted with 0% to 100% of EtOAc in hexane (1% $Et_3N$) (monitored by UV: 254 nm, 280 nm). The desired fractions were combined and evaporated to give a colorless foam 151 mg of 8d (50%) with a purity of 94.4% (HPLC)[2]. 1H NMR (300 MHz, DMSO-d6) spectrum is as follows: 11.49 (s, 1H), 9.41 (m, 1H), 7.71 (m, 1H), 7.13-7.40 (m, 14H), 6.87-6.90 (m, 4H), 6.05 (m, 1H), 5.41-5.45 (m, 2H), 4.68 (m, 1H), 4.25 (m, 1H), 4.08 (m, 1H), 3.98 (m, 1H), 3.72 (s, 6H), 3.52-3.65 (m, 4H), 3.34 (m, 1H), 2.63 (m, 1H), 2.53 (m, 1H), 1.21 (s, 9H), 0.96-1.12 (m, 12H). 31P NMR (161 MHz, DMSO-d6) 150.45, 150.34. MS: (APCI−) M−1=999.4.

Compound 8h

The below scheme 4 depicts the synthesis of a glutathione-sensitive compound comprising a disulfide (Compound 8h): ethyl N-((((2R,3R,4R,5R)-5-((bis(4-methoxyphenyl)(phenyl)methoxy)methyl)-4-(((2-cyanoethoxy)(diisopropylamino)phosphaneyl)oxy)-2-(2,4-dioxo-3,4-dihydropyrimidin-1(2H)-yl)tetrahydrofuran-3-yl)oxy)carbonyl)-S-(tert-butylthio)-L-cysteinate. The glutathione-sensitive moiety of Compound 8h is encompassed by Formula IVd and more specifically is represented by Formula IVd(i).

Scheme 4
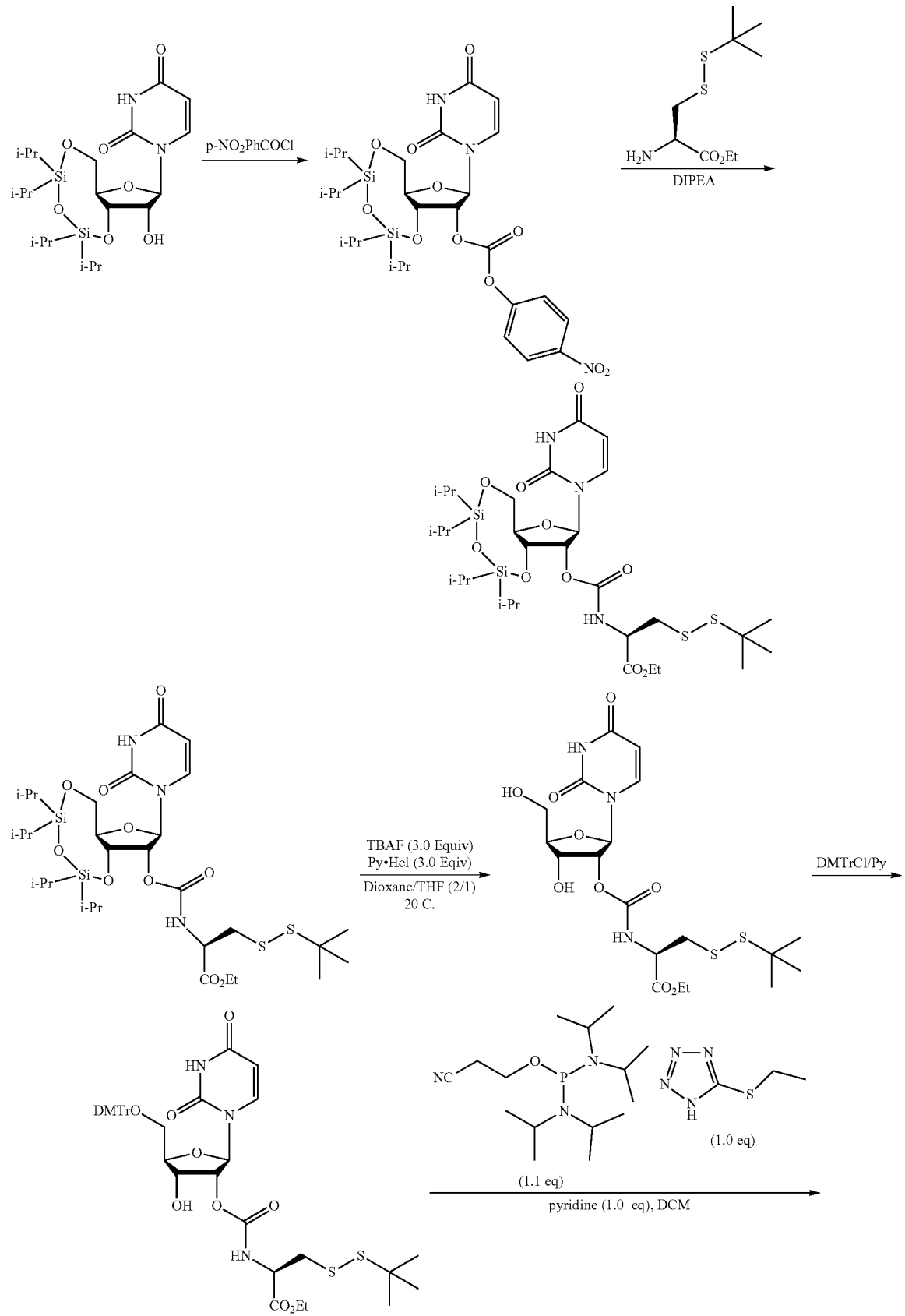

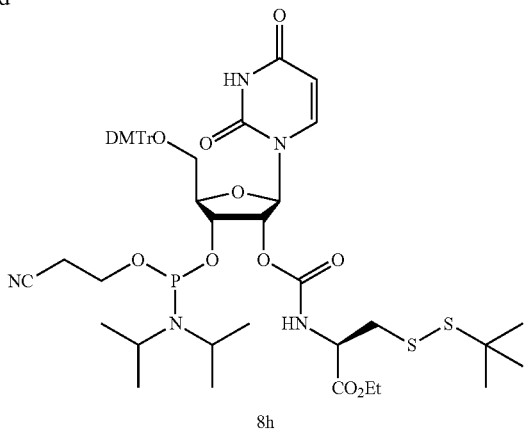

8h

Compound 8i

The below scheme 5 depicts the synthesis of a glutathione-sensitive compound comprising a sulfone (Compound 8i): (2R,3R,4R,5R)-5-((bis(4-methoxyphenyl)(phenyl)methoxy)methyl)-4-(((2-cyanoethoxy) (diisopropylamino)phosphaneyl)oxy)-2-(2,4-dioxo-3,4-dihydropyrimidin-1(2H)-yl)tetrahydrofuran-3-yl (2-(phenylsulfonamido)ethyl)carbamate. The glutathione-sensitive moiety of Compound 8i is encompassed by Formula IVb and more specifically is represented by Formula IVb(ii), wherein R is hydrogen.

Scheme 5

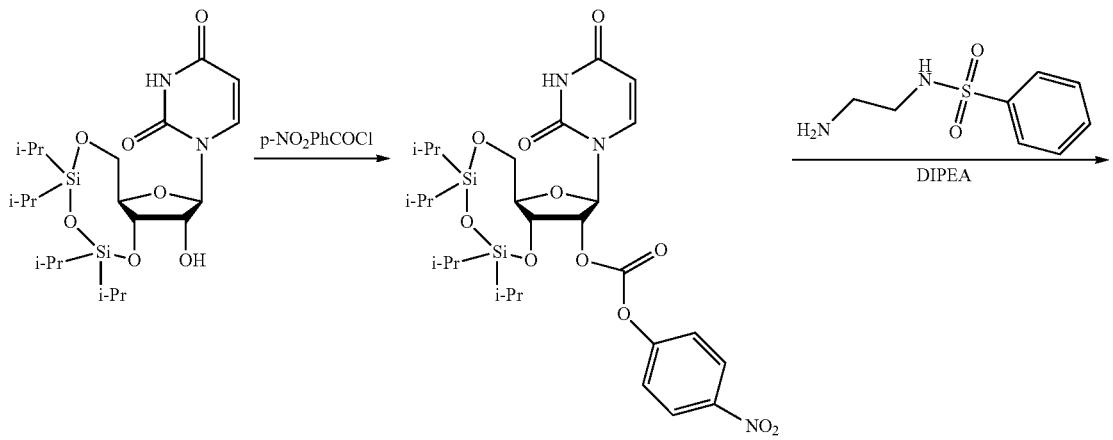

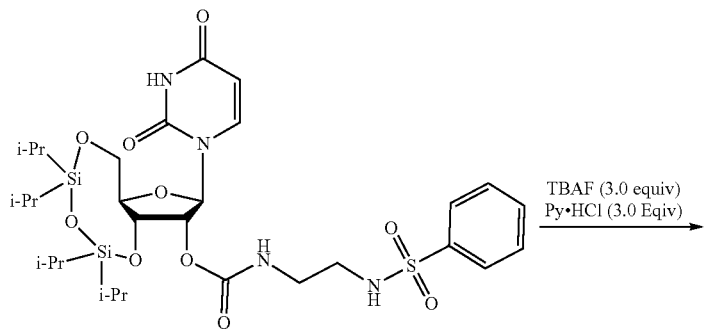

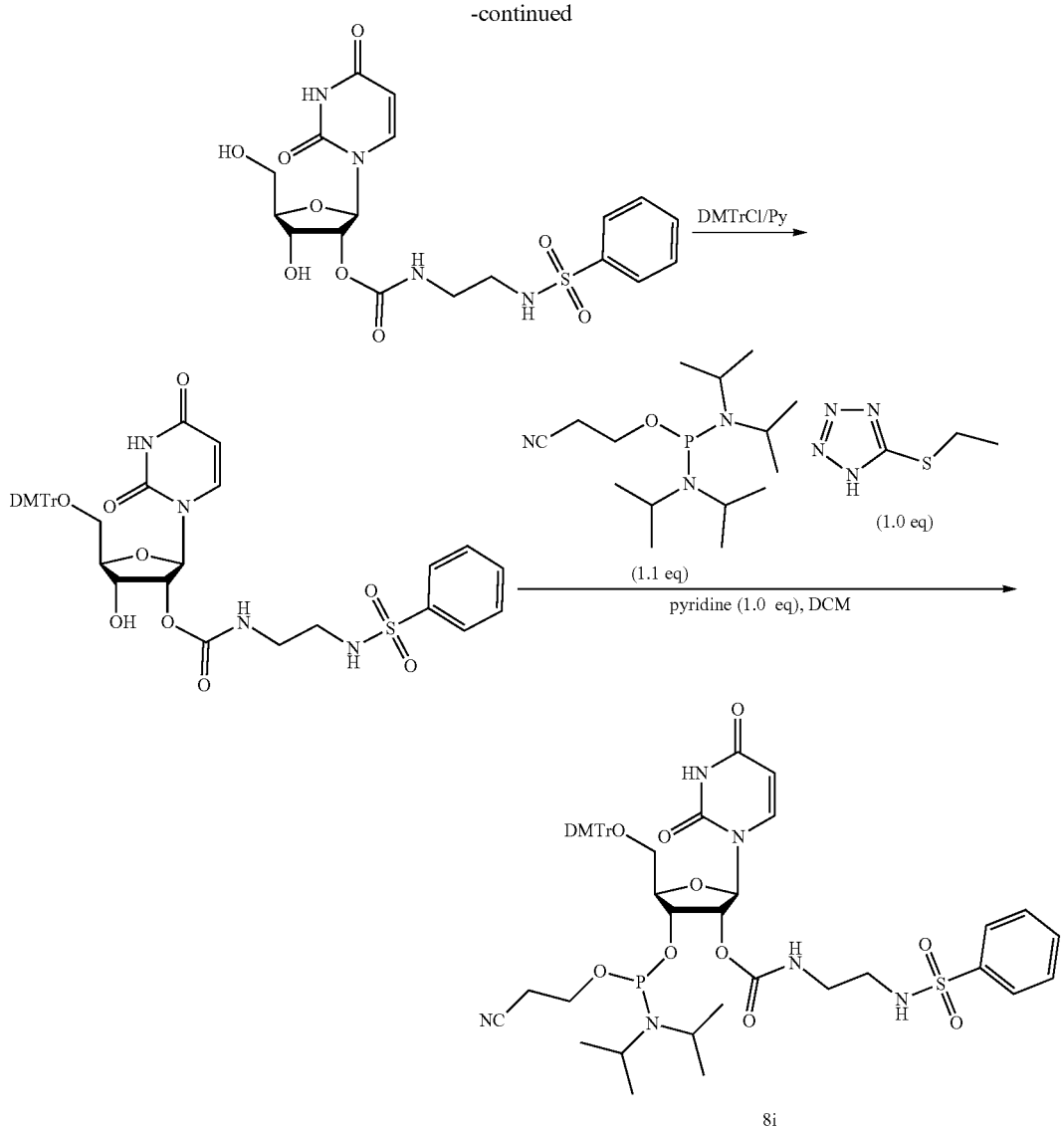

Example 2. Synthesis of Glutathione-Sensitive Oligonucleotides

Oligonucleotides were synthesized on a commercial oligo synthesizer. Test Compounds 1 and 2 (FIG. 1B) were synthesized using 2'-modified nucleoside phosphoramidites, i.e., 2'-F and 2'-OMe modified nucleoside phosphoramidites, and 2'-glutathione-sensitive nucleoside phosphoramidites. Test Compounds 1 and 2 contained one nucleotide having a reversible, glutathione-sensitive modification at the 2'-carbon, while the remaining nucleotides contained irreversible 2'-F or 2'-OMe modifications.

Oligonucleotide synthesis was carried out on a solid support in the 3' to 5' direction. The standard oligonucleotide synthesis protocol was employed. The coupling time was 300 seconds with 5-ethylthio-1H-tetrazole (ETT) as an activator. Iodine solution was used for phosphite triester oxidation. Synthesized oligonucleotides were treated with concentrated aqueous ammonium at 55° C. for 10 hours. After removal of ammonia in the suspensions, CPG's were removed by filtration. After the addition of triethylammonium acetate (TEAA), the crude oligonucleotides were analyzed and purified by strong anion exchange high performance liquid chromatography (SAX-HPLC). The obtained oligonucleotide solutions were pooled and concentrated and were desalted with water. Finally, oligonucleotides were lyophilized to a powder.

An oligonucleotide guide strand was synthesized for each of the two test compounds. One guide strand had a single 2'-glutathione-sensitive nucleoside located at nucleotide position 1 (i.e., the 5'-terminal nucleotide). The other guide strand had a single 2'-glutathione-sensitive nucleoside located at nucleotide position 14. The two guide strands contained the same nucleotide sequence that was complementary to a target mRNA sequence. Accordingly, the two oligonucleotide guide strands for Test Compound 1 and 2 were identical except for the nucleotide position of the 2'-glutathione-sensitive nucleoside moiety.

The above-described process was then repeated to prepare complementary oligonucleotide passenger strands, which did not contain a glutathione-sensitive moiety. The passenger strands were further modified by conjugating a phosphoramidite to a polyethylene glycol-GalNAc ligand via a spacer. The GalNAc terminated polyethylene glycol was conjugated via click chemistry to the 2'-carbon of four nucleotides of the tetraloop structure in the passenger strand using methods known in the art (see, e.g., WO 2016/100401).

Duplexes were formed by mixing each of the two complementary strands (guide and passenger) in a 1:1 molar ratio to obtain two dsRNAi inhibitor molecules: Test Compound 1 and Test Compound 2. See FIG. 1B. Test Compound 1 contains a 22-base pair guide strand having a 2'-glutathione-sensitive moiety at nucleotide positon 1 and a 36-base pair passenger strand without any glutathione-sensitive moiety, where the passenger strand contains four nucleotides in the tetraloop that are each conjugated to a polyethylene glycol-GalNAc ligand (see FIG. 1B). Test Compound 1 also had a free hydroxyl group (5'-OH) at the 5'-carbon at the 5'-end of the guide strand. Except for the glutathione-sensitive nucleotide at nucleotide position 1 of the guide strand, the remaining nucleotides in Test Compound 1 were irreversibly modified with either 2'-F or 2'-OMe.

Test Compound 2 contains a 22-base pair guide strand having a 2'-glutathione-sensitive moiety at nucleotide positon 14 and a 36-base pair passenger strand without any glutathione-sensitive moiety, where the passenger strand contains four nucleotides in the tetraloop that are each conjugated to a polyethylene glycol-GalNAc ligand (see FIG. 1B). Except for the glutathione-sensitive nucleotide at nucleotide position 14 of the guide strand, the remaining nucleotides in Test Compound 2 were irreversibly modified with either 2'-F or 2'-OMe.

It has been reported that bulky 2'-modified nucleosides are generally not well tolerated at nucleotide position 14 of double stranded RNAi inhibitor molecules (Zheng et al., FASEB Journal, 2013, 27(2):1-10), and that small functional moieties, such as 2'-F or 2'-OMe, are preferably used to modify nucleosides at position 14. In Test Compound 2, the bulky 2'-glutathione-sensitive moiety at position 14 is cleaved by glutathione in the cytosol to yield a much smaller hydroxyl group at the 2'-carbon, which also happens to be the natural substituent for a ribonucleotide at that carbon position. Thus, it was expected that Test Compound 2 would have little to no RNA inhibition activity unless the glutathione-sensitive moiety was released from Test Compound 2. As such, Test Compound 2 provides a test for in vivo removal of the glutathione-sensitive moiety.

Two control double stranded RNAi inhibitor molecules (Control Compound A and Control Compound B) were also prepared as described above except that none of the nucleotides in the control compounds included a glutathione-sensitive moiety. See FIG. 1A. All of the nucleotides in the control compounds were irreversibly modified with 2'-F or 2'-OMe in the same pattern as the Test Compounds (other than the position modified with the glutathione-sensitive moiety). Control Compound A was synthesized with natural phosphate (5'-$PO_4^{2-}$) at the 5'-carbon of the 5'-terminal nucleotide of the guide strand, whereas Control Compound B contained a free hydroxyl group (5'-OH) at the 5'-carbon of the 5'-terminal nucleotide of the guide strand. The guide strands of Control Compounds A and B contained the same nucleotide sequence and, therefore, recognized the same target mRNA sequence as Test Compounds 1 and 2.

Example 3. Release Kinetics of 2'-Reversibly Modified Nucleoside and Oligonucleotide A reversibly-modified nucleoside (uridine) containing a glutathione-sensitive moiety at the 2'-carbon, as shown below in Scheme 7, was prepared. Release studies of the 2'-glutathione-sensitive uridine were conducted by dissolving the modified nucleoside in PBS buffer containing a 500-fold excess of glutathione (5 mM glutathione) at pH 7.5. The progress of the disulfide release studies was monitored by RP-HPLC. RP-HPLC showed two new peaks corresponding to the intermediate species "int. A" and "int. B", which are depicted in Scheme 7 below. The intermediate species were slowly converted to the desired uridine and the benzothiazolone release product, as shown in Scheme 7 below.

Figure 2:
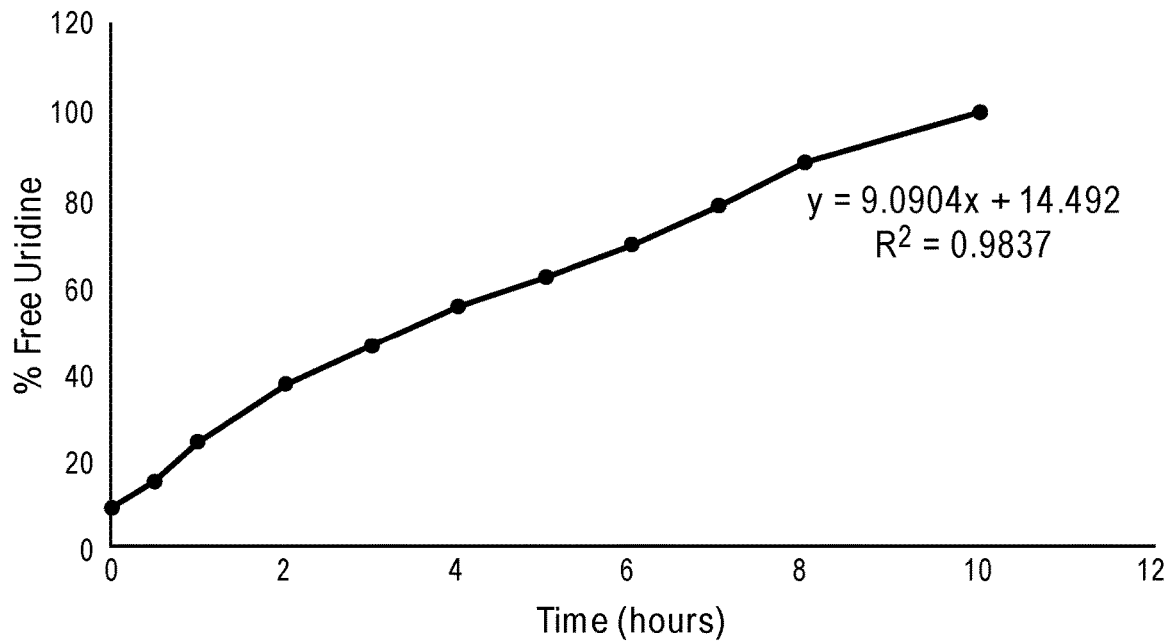
FIG. 2 depicts the release rate of uridine from a reversibly-modified uridine having a glutathione-sensitive moiety at the 2'-carbon in accordance with the present disclosure, following incubation with glutathione, as described in Example 3.

As shown in Scheme 7 below, the release mechanism for the 2'-glutathione-sensitive uridine proceeds through a two-step reaction. The first step is a disulfide exchange reaction after exposure to glutathione, which is rapid, and results in full conversion to the glutathione adducts within 30-60 minutes. The initial disulfide cleavage produces two intermediates "int. A" and "int. B." The second step is rapid intramolecular cyclization via O→S acyl transfer reaction to release benzothiazolone from the nucleoside, leaving a hydroxyl group at the 2'-position of the nucleoside. The reaction kinetic data for benzothiazolone formation supported the biphasic profile of uridine formation. The half-life (t½) for cyclization and release of benzothiazolone (resulting in free uridine) was approximately 4 hours. See FIG. 2.

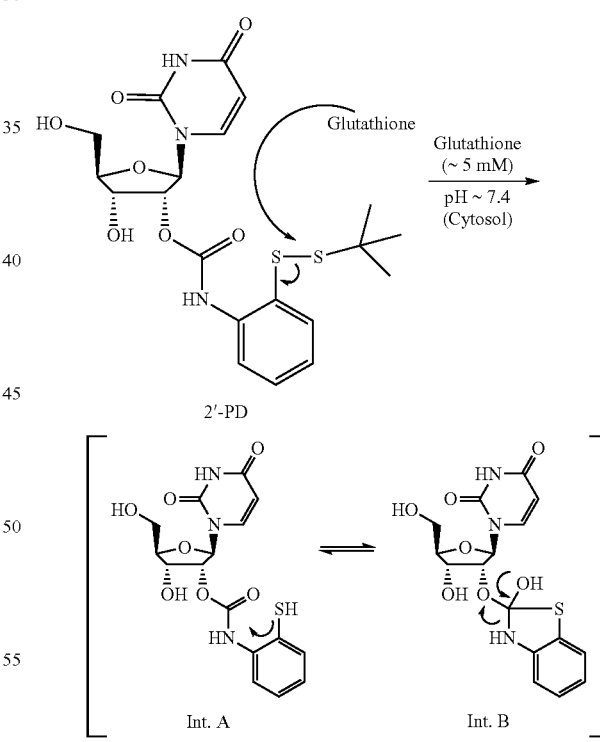

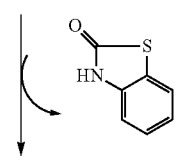

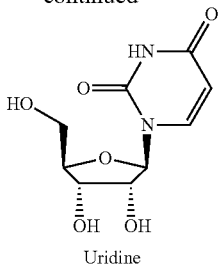

Uridine

Figure 3:
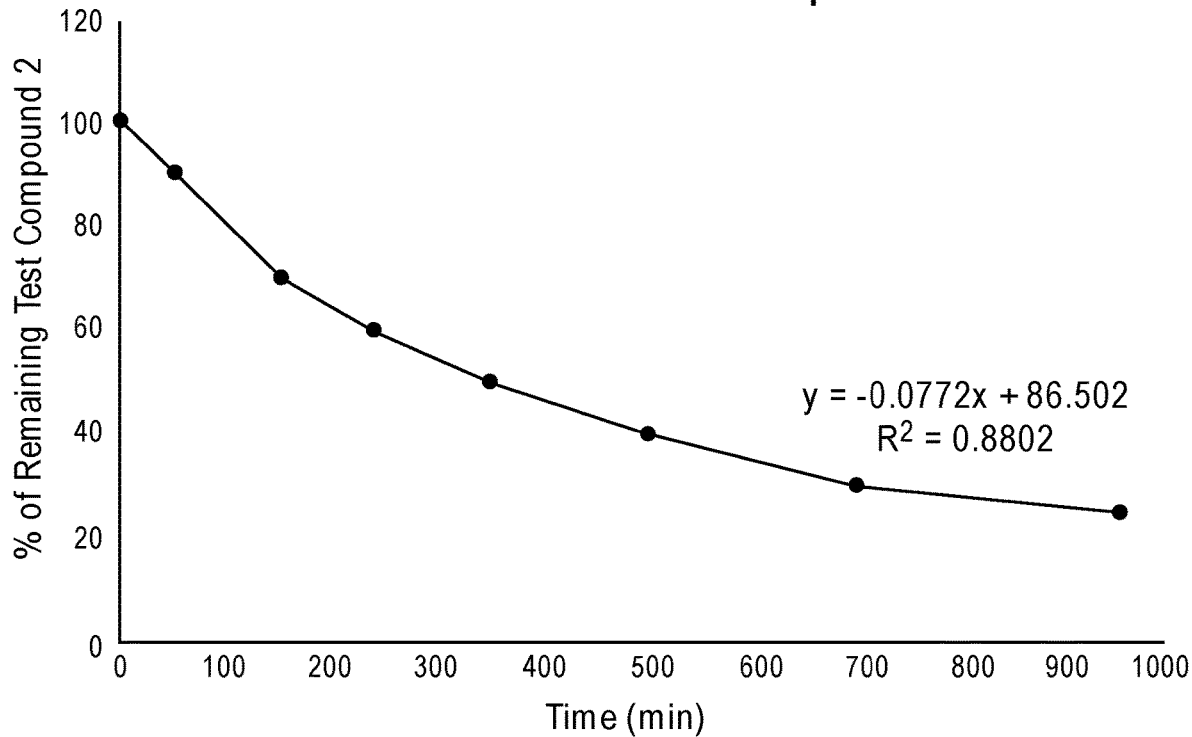
FIG. 3 depicts the rate of disappearance of Test Compound 2 following incubation with glutathione, as described in Example 3.

The release rate was also determined for a glutathione-sensitive oligonucleotide (i.e., Test Compound 2), as shown in FIG. 3, which shows a time course of the percentage of Test Compound 2 remaining. 500 equivalents of glutathione (21 mg) was added to the Test Compound 2 (1 mg) at pH 7.5 in 10 mM phosphate buffer (volume of 10 mL). The rate of Test Compound 2 disappearance was monitored by RP-HPLC. As is evident in FIG. 3, the reaction is bi-phasic. The half-life ($t_{1/2}$) for cyclization and release of the glutathione-sensitive moiety from Test Compound 2 was approximately 6.5 hours (about 400 minutes). See FIG. 3.

Example 4. In Vitro Potency of Test Compound 1

Murine Hepatocytes

The ability of Test Compound 1 to knockdown expression of a target mRNA was tested in vitro. As noted above, the test oligonucleotides and control oligonucleotides recognize the same target sequence. Test Compound 1 and Control Compounds A and B were reverse transfected into murine hepatocytes using LIPOFECTAMINE® RNAiMax (Thermo Fisher Scientific Inc., Rockville, MD) in a 96 well plate as per manufacturer's protocol. The final concentration of the test and control oligonucleotides ranged from 1000 pM to 0.06 pM. 12000 cells/well were added to the plate. The plate was incubated at 37° C. for 48 hours. At the end of 48 hours, the cells were lysed by adding 30 μl of ISCRIPT™ lysis buffer per well. 22 μl of the lysate was transferred to a fresh plate and used to make cDNA as per the manufacturer's protocol. Quantitative PCR was performed with the target sequence normalized to human SFR69 gene (hSFRS9-F569 (HEX)) at 55° C. Graphs were plotted using GraphPad Prism (GraphPad Software Inc., La Jolla, CA), and the $IC_{50}$ values were calculated.

Figure 4:
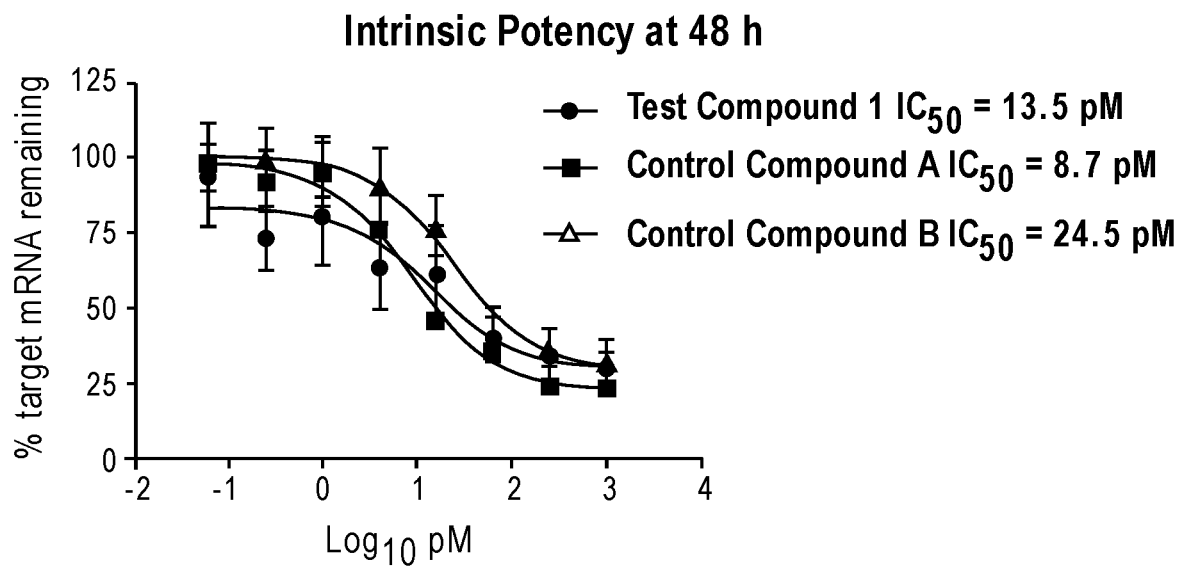
FIG. 4 depicts the potency (including $IC_{50}$) of Test Compound 1 in comparison to the control compounds (Compound A and Compound B), as measured by the knockdown of target mRNA 48 hours after transfection of the compounds into murine hepatocytes, as described in Example 4.

FIG. 4 depicts the potency of different concentrations of Test Compound 1 in the lipid transfection assay after 48 hours. Control Compound A (having a 5'-natural phosphate at the 5'-terminal nucleotide of the guide strand) had an $IC_{50}$ of about 8.7 pM, whereas Control Compound B (having a 5'-hydroxyl at the 5'-terminal nucleotide of the guide strand) was less effective at reducing expression of the target mRNA, with an $IC_{50}$ of about 24.5 pM. For Test Compound 1, the $IC_{50}$ was about 13.5 pM. This $IC_{50}$ value of Test Compound 1 was more comparable to Control Compound A, suggesting that the 5'-hydroxyl at the 5'-terminal nucleotide of the guide strand of Test Compound 1 was phosphorylated by a kinase in the cytosol. It is expected that release of the glutathione-sensitive moiety at the 2'-carbon at nucleoside position 1 of the guide strand of Test Compound 1 in the cytosol makes the 5'-hydroxyl more amenable to kinase phosphorylation, which in turn should facilitate Ago2-mediated RISC loading of the guide strand for target mRNA knockdown.

Monkey Hepatocytes

Figure 5:
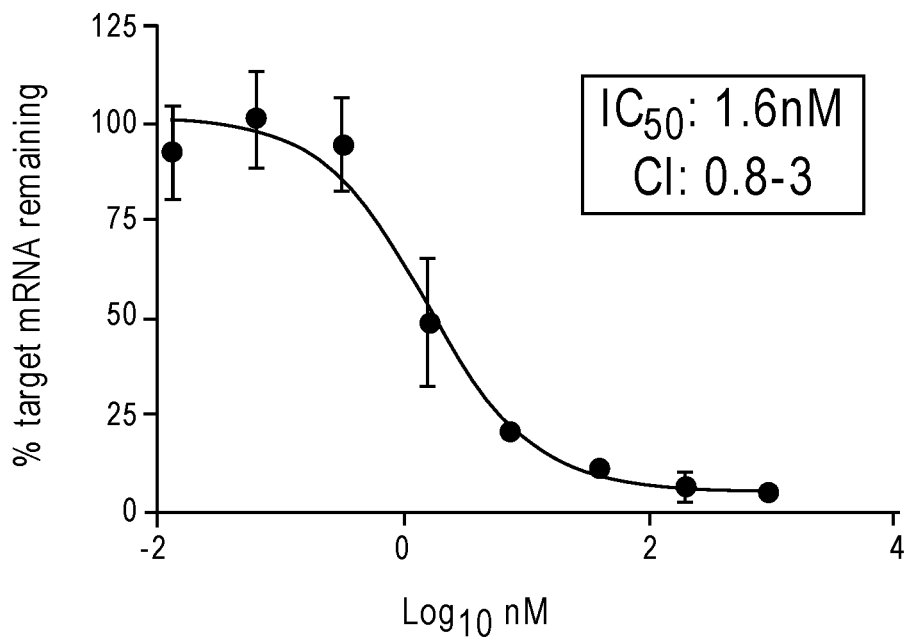
FIG. 5 depicts the potency (including $IC_{50}$) of Test Compound 1 in monkey hepatocytes, as measured by the knockdown of target mRNA 24 hours after transfection, as described in Example 4.

Primary monkey hepatocytes were obtained from Life Technologies Corporation (Carlsbad, CA) and thawed and plated as per manufacturer's protocol in CORNING® BIO-COAT™ 96 well plates. After 4-6 hours of plating, the media was replaced with 90 μl of Williams E incubation media per well. Test Compound 1 was serially diluted starting with a concentration of 1 μM to 12.8 μM (5-fold reduction). 10 μl of Test Compound 1 was added to the respective wells in the absence of LIPOFECTAMINE® (Thermo Fisher Scientific, Inc.). The plate was incubated at 37° C. and knockdown of an RNA target was tested at 24 hours. At the end of 24 hours, target RNA was extracted and purified using SV96 Total RNA Isolation System (Promega, Madison, WI) as per the manufacturer's protocol. cDNA was prepared using the High-Capacity cDNA Reverse Transcription Kit (Applied Biosystems Corporation). Quantitative PCR was carried out at 60° C. with the target sequence normalized to Homo sapiens peptidyl prolyl isomerase B PPIB. Graphs were plotted using the GraphPad Prism software (GraphPad Software Inc.) and the $IC_{50}$ values were calculated. FIG. 5 shows the potency at 24 hours of different concentrations of Test Compound 1 delivered to primary monkey hepatocytes in the absence of any lipid transfection agent. Test Compound 1 had an $IC_{50}$ of 1.6 nM at 24 hours.

Example 5. In Vivo Potency and Duration of Effect for Test Compounds 1 and 2

Test Compound 1 and Test Compound 2 were diluted in PBS to a 1 mg/kg working solution. On the same day as the PBS dilution, CD-1 female mice were injected subcutaneously with a single 1 mg/kg dose of Test Compound 1, Test Compound 2, or a control PBS solution. Post-dosing (3, 10, 21 and 28 days) animals were exsanguinated by cardiac puncture after euthanasia in $CO_2$. The left medial lobe of the liver was removed and a 1-4 mm punch was removed and placed into a 96 well plate on dry ice. After all samples were collected, RNA and cDNA were prepared for quantitative PCR (qPCR). All samples were prepared in triplicate and qPCR was performed using the CFX384 TOUCH™ Real-Time PCR Detection System (BioRad Laboratories, Inc., Hercules, CA). All samples were then normalized to the PBS treated control animals and blotted using GraphPad Prism software.

Figure 6:
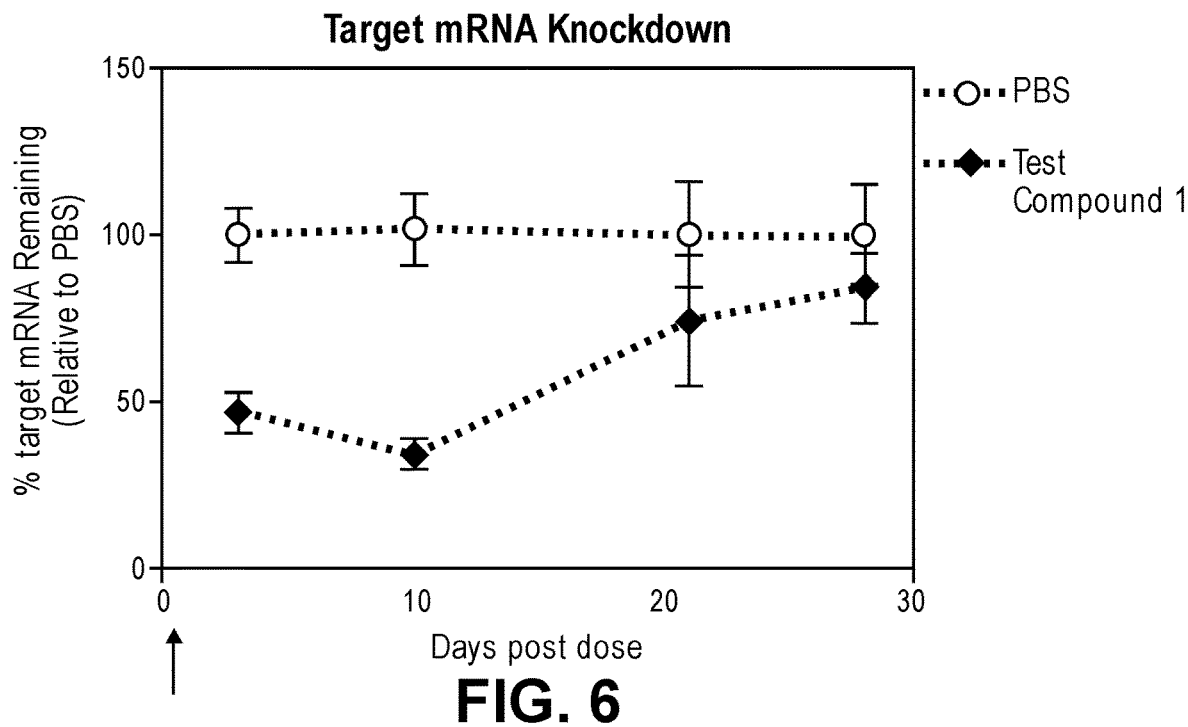
FIG. 6 depicts the potency in mice, as measured by the knockdown of target mRNA, and duration of effect following the in vivo administration of Test Compound 1 in comparison to a control PBS injection, as described in Example 5.

FIG. 6 depicts an in vivo duration study of Test Compound 1. Subcutaneous injection of Test Compound 1 at 1 mg/kg resulted in more than 50% knockdown of target RNA at day 3. Increased levels of target RNA knockdown were observed at day 10, suggesting slow release of the glutathione-sensitive moiety to generate an oligonucleotide substrate that is more amenable to kinase phosphorylation and subsequent Ago-2 mediated RISC loading for target gene knockdown. These results indicate that conjugating a glutathione-sensitive moiety to the 2'-carbon of the nucleoside at position 1 of the guide strand of a dsRNAi inhibitor molecule can stabilize the dsRNAi inhibitor molecule during transit to the cytosol of the cell and facilitate effective knockdown of target RNA in the cytosol, where the glutathione-sensitive moiety of the oligonucleotide is removed in the presence of glutathione.

Figure 7:
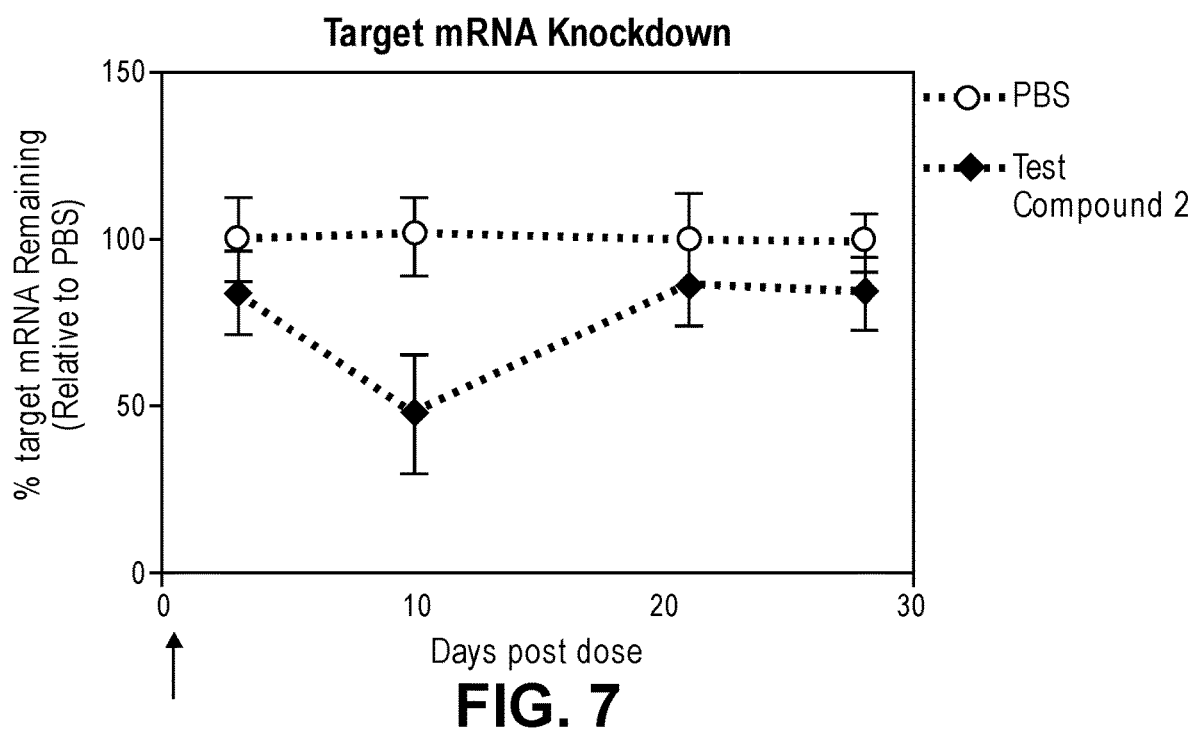
FIG. 7 depicts the potency in mice, as measured by the knockdown of target mRNA, and duration of effect following the in vivo administration of Test Compound 2 in comparison to a control PBS injection, as described in Example 5.

FIG. 7 depicts an in vivo duration study of Test Compound 2. As noted above, Test Compound 2 is modified with a glutathione-sensitive moiety at the 2'-carbon at nucleoside position 14 of the guide strand (see FIG. 1B), a nucleotide position that generally does not tolerate bulky modifications at the 2'-carbon. Thus, it was expected that Test Compound 2 would have little to no RNA knockdown effect unless the bulky, glutathione-sensitive moiety was released from Test Compound 2. As shown in FIG. 7, subcutaneous injection of Test Compound 2 at 1 mg/kg resulted in about 50% knockdown of target RNA by day 10, suggesting slow in vivo release of the glutathione-sensitive moiety in the cytosol to generate a natural 2'-OH in place of the reversible, glutathione-sensitive moiety at nucleotide position 14 of the guide strand.

We claim:

1. A glutathione-sensitive oligonucleotide, wherein the glutathione-sensitive oligonucleotide comprises at least one nucleotide represented by Formula I:

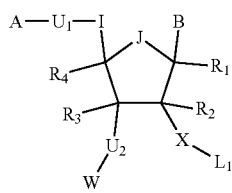

I wherein X is O, S, Se or NR', wherein R' is hydrogen, halogen, an aliphatic, an aryl, a heteroaryl or a heterocycle;

wherein $R_1$, $R_2$, $R_3$ and $R_4$ are each independently hydrogen, halogen, OH, $C_1$-$C_6$ alkyl, $C_1$-$C_6$ haloalkyl or wherein two of $R_1$, $R_2$, $R_3$ and $R_4$ are taken together to form a 5-8 membered ring, wherein the ring optionally contains a heteroatom;

wherein J is O, S, NR', CR'R", wherein each of R' and R" is independently hydrogen, halogen, an aliphatic, aryl or heteroaryl;

wherein B is hydrogen, a natural nucleobase, a modified nucleobase or a universal nucleobase;

wherein $U_2$ is absent or O, S, NR', or CR'R", wherein R' and R" are each independently hydrogen, an aliphatic, an aryl, a heteroaryl, a heterocycle or a cycloalkyl;

wherein W is hydrogen, a phosphate group, an internucleotide linking group attaching the at least one nucleotide represented by Formula I to a nucleotide or an oligonucleotide, a halogen, OR', SR', NR'R", an aliphatic, an aryl, a heteroaryl, a cycloalkyl, a heterocycle, wherein R' and R" are each independently hydrogen, halogen, an aliphatic, an aryl, a heteroaryl, a heterocycle or are taken together to form a heterocyclic ring;

wherein I is absent or O, S, NR', or CR'R", wherein R' and R" are each independently hydrogen, an aliphatic, an aryl, a heteroaryl, a heterocycle and a cycloalkyl;

wherein $U_1$ is absent, hydrogen, an internucleotide linking group attaching the at least one nucleotide represented by Formula I to a nucleotide or an oligonucleotide, or O, S, NR' or CR'R", wherein R' and R" are each independently hydrogen, an aliphatic, an aryl, a heteroaryl, a heterocycle and a cycloalkyl and wherein at least one of $U_1$ or W is an internucleotide linking group attaching the at least one nucleotide represented by Formula I to a nucleotide or an oligonucleotide and provided that if $U_1$ is an internucleotide linking group, A is absent;

wherein I and $U_1$ can be combined to form CR'—CR" alkyl, CR'—CR" alkenyl, CR'—CR" alkynyl, an aliphatic, an aryl, a heteroaryl, a heterocycle or taken together to form cycloalkyl or heterocyclic ring;

wherein A is absent, a hydrogen, a phosphate group, a phosphate mimic or a phosphoramidate; and wherein L is a glutathione-sensitive moiety selected from a glutathione-sensitive moiety represented by:

Formula II

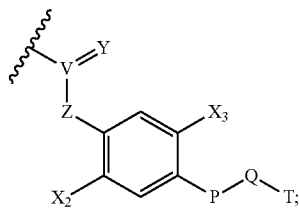

II

Formula III

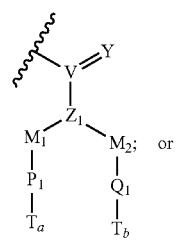

III wherein Y is O, S, Se, or NR', wherein R' is hydrogen, halogen, an aliphatic, an aryl, a heteroaryl, or a heterocycle;

wherein Z is O, S, NR', or CR'R", wherein R' and R" are each independently hydrogen, halogen, $CH_3$, an aliphatic, an aryl, a heteroaryl, a heterocycle, or R' and R" are taken together to form a heterocyclic ring;

wherein $Z_1$ is N or CR', wherein R' is hydrogen, halogen, an aliphatic, an aryl, a heteroaryl, a heterocycle;

wherein V is C or SO;

wherein $X_2$ and $X_3$ are independently hydrogen, halogen, nitro, amino, acyl, an aliphatic, $OR_{10}$, $COR_{10}$, $CO_2R_{10}$, or $NQ_1Q_2$; wherein $R_{10}$ is independently hydrogen, an aliphatic, a hydroxyl or alkoxy substituted aliphatic, an arylaliphatic, a hydroxyl or alkoxy substituted aryl, or an alkoxy substituted heterocyclic;

wherein G and E can be each independently absent or $CH_2$, CHR', CR'R", NH, or NR', wherein R' and R" are each independently hydrogen, halogen, an aliphatic, an aryl, a heteroaryl, a heterocycle or R' and R" are taken together to form a heterocyclic ring;

wherein P and Q are taken together to form a disulfide bridge or a sulfonyl group;

wherein $P_1$ and $Q_1$ are taken together to form a disulfide bridge or a sulfonyl group or wherein $P_1$ and $Q_1$ are each independently a disulfide bridge or a sulfonyl group;

wherein when $P_1$ and $Q_1$ form a disulfide bridge, $M_1$, $M_2$, $P_1$, and $Q_1$ can form a 4-9 membered ring, wherein the ring can be aromatic or cycloalkyl, wherein the aromatic or cycloalkyl ring can optionally contain a heteroatom;

wherein T is an aliphatic, an aryl, or T is a ligand optionally connected via a spacer to P or Q;

wherein $T_a$ and $T_b$ are each independently absent or $CH_3$, an aliphatic, an aryl, a heteroaryl, a heterocycle or a ligand optionally connected via any spacer to $P_1$ or $Q_1$;

wherein $M_1$ and $M_2$ are each independently an aliphatic, an aromatic, a heteroaryl, or a cycloalkyl;

wherein $M_3$ and $M_4$ are each independently hydrogen, an aliphatic, an aromatic, a heteroaryl, a cycloalkyl or COOR, wherein R is hydrogen, $CH_3$, or an aliphatic, or $M_3$ and $M_4$ can be taken to form a 4-9 membered ring, wherein the ring can be aromatic or cycloalkyl, wherein the aromatic or cycloalkyl ring can optionally contain a heteroatom;

wherein K is C, CH, or an aliphatic; and wherein n is 0-5.

2. The glutathione-sensitive oligonucleotide of claim 1, wherein:

a) L is represented by Formula II, wherein Y is O; wherein Z is NR'; wherein R' is hydrogen or an aliphatic; and wherein V is C;

b) L is represented by Formula II, wherein Y is O; wherein Z is NR'; wherein R' is hydrogen or an aliphatic; wherein V is C; and wherein $X_2$ and $X_3$ are independently hydrogen, halogen, nitro or amino;

c) L is represented by Formula III, wherein Y is O, S or NH; wherein $Z_1$ is N or CH; and wherein V is C;

d) L is represented by Formula III, wherein Y is O, S or NH; wherein $Z_1$ is N or CH; wherein V is C; and wherein $M_1$ and $M_2$ are $C_2$ to $C_6$ alkyl or are taken together with $P_1$ and $Q_1$ to form a 5-8 membered ring, wherein the ring is cycloalkyl;

e) L is represented by Formula IIIa:

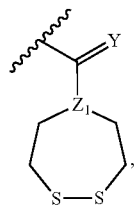

IIIa wherein Y is O, S or NH; and wherein $Z_1$ is N or CR', wherein R' is hydrogen, halogen, an aliphatic, an aryl, a heteroaryl, or a heterocycle;

f) L is represented by Formula IIIb:

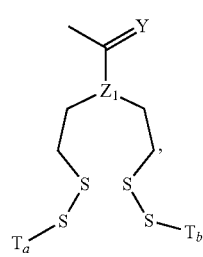

IIIb wherein Y is O, S or NH; and wherein $Z_1$ is N or CR', wherein R' is hydrogen, halogen, an aliphatic, an aryl, a heteroaryl, or a heterocycle; and $T_a$ and $T_b$ are each independently absent or $CH_3$, an aliphatic, an aryl, a heteroaryl, a heterocycle or a ligand optionally connected via spacer to a sulfur atom;

g) L is represented by Formula IIIa(i) or IIIb(i):

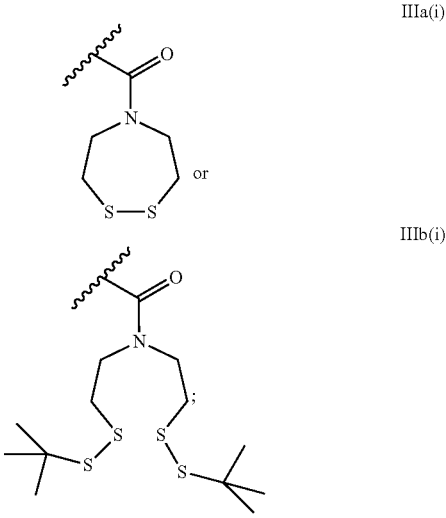

h) L is represented by Formula IV, wherein Y is O, S or NH; wherein Z is NH or N—$CH_3$; wherein V is C; and wherein G is $CH_2$ and E is absent or wherein E is $CH_2$ and G is absent;

i) L is represented by Formula IV, wherein Y is O, S or NH; wherein Z is NH or N—$CH_3$; wherein V is C; wherein G is $CH_2$ and E is absent or wherein E is $CH_2$ and G is absent; and wherein $M_3$ and $M_4$ are independently $C_2$ to $C_6$ alkyl or taken together to form a 5-8 membered ring, wherein the ring is cycloalkyl;

j) L is represented by Formula IVa:

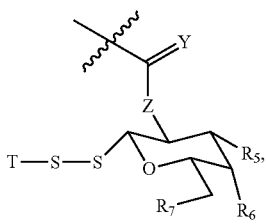

IVa wherein Y is O, S, or NH; wherein Z is O, S or NH; wherein $R_5$, $R_6$, and $R_7$ are each independently OAcyl, NHR', NR', or CR'R", wherein R' and R" are each independently hydrogen, halogen, an aliphatic, an aryl, a heteroaryl, a heterocyclic, or can be taken together to form a heterocyclic ring; and wherein T is a branched or unbranched $C_2$-$C_6$ alkyl or a ligand optionally connected via spacer to a sulfur atom;

k) L is represented by Formula IVb:

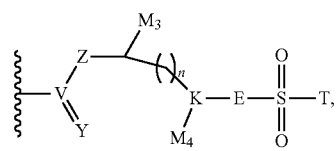

IVb wherein Y is O, S, or NH; Z is O, S or NH; V is C; $M_3$ and $M_4$ are hydrogen; K is CH or an aliphatic; E is NH or NR', wherein R' is an aliphatic; n is 0-5; and T is $C_2$ to $C_6$ alkyl, an aryl, or T is a ligand optionally connected via a spacer to a sulfur atom;

l) L is represented by Formula IVc:

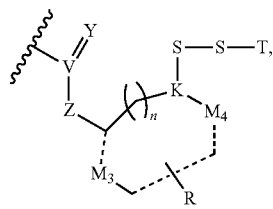

IVc wherein Y is O, S, or NH; Z is O, S, or NR', wherein R' is hydrogen, halogen, $CH_3$, an aliphatic, an aryl, a heteroaryl, or a heterocycle; V is C; $M_3$ and $M_4$ are taken together to form a 5-8 membered ring, wherein the ring is a cycloalkyl, optionally substituted with a heteroatom; K is a branched or unbranched $C_2$ to $C_6$ alkyl; n is 0-5; T is a $C_2$ to $C_6$ alkyl, an aryl, or T is a ligand optionally connected via a spacer; and wherein R is hydrogen, $CH_3$, an aliphatic, an aryl, a heteroaryl, a cycloalkyl, a heterocycle or R is a targeting ligand optionally connected via a spacer;

m) L is represented by Formula IVd:

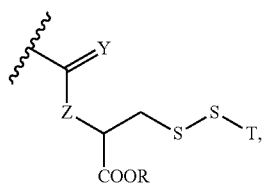

IVd wherein Y is O, S, or NH; Z is O, S, NH, or $NCH_3$; T is a $C_2$ to $C_6$ alkyl, an aryl, or T is a ligand optionally connected via a spacer to a sulfur atom; and R is hydrogen, $CH_3$ or a $C_2$ to $C_6$ alkyl;

n) L is represented by Formula IVe:

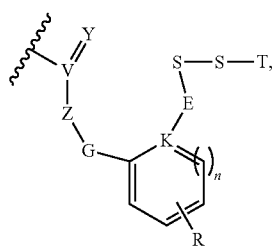

IVe wherein Y is O, S, or NH; Z is O, S, or NR', wherein R' is hydrogen, halogen, $CH_3$, an aliphatic, an aryl, a heteroaryl, or a heterocycle; V is C or SO; G and E can be each independently absent, or $CH_2$, CHR', CR'R", NH, NR', wherein R' and R" are each independently hydrogen, halogen, an aliphatic, an aryl, a heteroaryl, a heterocycle or R' and R" are taken together to form a heterocyclic ring; K is C or CH; n is 0-5; T is a $C_2$ to $C_6$ alkyl, an aryl, or T is a ligand optionally connected via a spacer; and wherein R is hydrogen, $CH_3$, an aliphatic, an aryl, a heteroaryl, a cycloalkyl, a heterocycle or R is a targeting ligand optionally connected via a spacer;

o) L is represented by Formula IVe, wherein Z is NH or N—$CH_3$; and wherein one or both of G and E are absent, $CH_2$, or CR'R", wherein R' and R" are independently hydrogen or an aliphatic; or p) L is represented by Formula IVa(i), IVe(vi), IVe(vii) or IVe(viii):

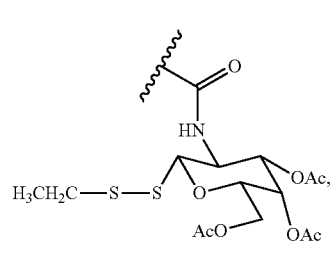

IVa(i)

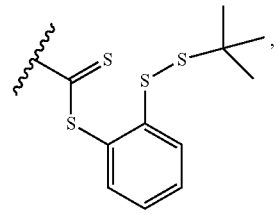

IVe(vi)

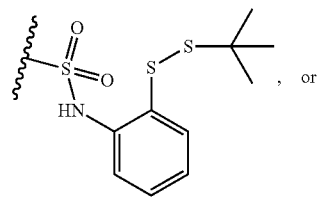

IVe(vii)

, or

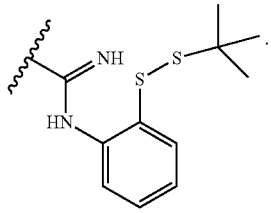

IVe(viii)

3. The glutathione-sensitive oligonucleotide according to claim 1, wherein the oligonucleotide is a double-stranded oligonucleotide comprising a first strand and a second strand.

4. The glutathione-sensitive oligonucleotide according to claim 3, wherein the double stranded oligonucleotide is a double-stranded RNAi inhibitor molecule and the first strand comprises a sense strand and the second strand comprises an antisense strand and optionally:
  wherein the double stranded RNAi inhibitor molecule comprises a region of complementarity between the sense strand and the antisense strand of about 15 to 45 nucleotides;
  wherein the region of complementarity between the sense strand and the antisense strand is 20 to 30, 21 to 26, 19 to 24, or 19 to 21 nucleotides;

wherein the at least one nucleotide represented by Formula I is located on the antisense strand; and/or wherein the at least one nucleotide represented by Formula I is located on the sense strand.

5. The glutathione-sensitive oligonucleotide according to claim 4, wherein the at least one nucleotide represented by Formula I is located at nucleotide position 1 of the antisense strand; at nucleotide position 14 of the antisense strand; or at a nucleotide position at or adjacent to the Ago2 cleavage site of the sense strand.

6. The glutathione-sensitive oligonucleotide according to claim 4, wherein the double stranded RNAi inhibitor molecule contains a tetraloop.

7. The glutathione-sensitive oligonucleotide according to claim 1, wherein the oligonucleotide is a single stranded oligonucleotide.

8. The glutathione-sensitive oligonucleotide according to claim 7, wherein the single stranded oligonucleotide is a single stranded nucleic acid inhibitor molecule and optionally:
   wherein the single stranded oligonucleotide is a conventional antisense oligonucleotide, a ribozyme, a microRNA, an antagomir, or an aptamer; or
   wherein the single stranded RNAi inhibitor molecule is about 14-50, 16-30, 18-22, or 20-22 nucleotides in length.

9. The glutathione-sensitive oligonucleotide according to claim 1, wherein the glutathione-sensitive oligonucleotide contains 1-5 nucleotides represented by Formula I, and optionally wherein every nucleotide of the glutathione-sensitive oligonucleotide is modified and wherein every nucleotide that is not modified with the glutathione-sensitive moiety is modified with an irreversible modification.

10. The glutathione-sensitive oligonucleotide according to claim 1, further comprising a delivery agent, wherein the delivery agent facilitates transport of the glutathione-sensitive oligonucleotide across an outer membrane of a cell and optionally:
   wherein the delivery agent is selected from the group consisting of carbohydrates, peptides, lipids, vitamins and antibodies; or
   wherein the delivery agent is selected from the group consisting of N-Acetylgalactosamine (GalNAc), mannose-6-phosphate, galactose, oligosaccharide, polysaccharide, cholesterol, polyethylene glycol, folate, vitamin A, vitamin E, lithocholic acid and a cationic lipid.

11. A pharmaceutical composition comprising the glutathione-sensitive oligonucleotide according to claim 1 and a pharmaceutically acceptable carrier.

12. A method for reducing expression of a target gene in a subject comprising administering the glutathione-sensitive oligonucleotide as claimed in claim 1, or a pharmaceutical composition comprising said glutathione-sensitive oligonucleotide, to a subject in need thereof in an amount sufficient to reduce expression of the target gene.

13. A nucleoside phosphoramidite, wherein the nucleoside phosphoramidite is represented by Formula VIII:

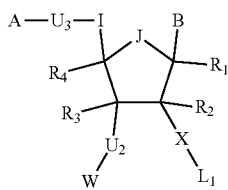

VIII wherein $L_1$ is a glutathione-sensitive moiety;

wherein $A_1$ is absent, hydrogen, a phosphate group, a phosphate mimic, a phosphoramidate, a phosphoramidite, a protecting group, or a solid support;

wherein $W_1$ is a phosphoramidite, a protecting group, a solid support, hydrogen, halogen, OR', SR', NR'R", an aliphatic, an aryl, a heteroaryl, a cycloalkyl, or a heterocycle, wherein R' and R" are each independently hydrogen, halogen, an aliphatic, an aryl, a heteroaryl, a heterocycle or are taken together to form a heterocyclic ring;

wherein $U_3$ is a hydrogen or O, S, NR' or CR'R", wherein R' and R" are each independently hydrogen, an aliphatic, an aryl, a heteroaryl, a heterocycle or a cycloalkyl;

wherein at least $A_1$ is a phosphoramidite and $U_3$ is O or at least $W_1$ is a phosphoramidite and $U_2$ is O;

wherein X is O, S, Se or NR', wherein R' is hydrogen, halogen, an aliphatic, an aryl, a heteroaryl or a heterocycle;

wherein $R_1$, $R_2$, $R_3$ and $R_4$ are each independently hydrogen, halogen, OH, $C_1$-$C_6$ alkyl, $C_1$-$C_6$ haloalkyl or wherein two of $R_1$, $R_2$, $R_3$ and $R_4$ are taken together to form a 5-8 membered ring, wherein the ring optionally contains a heteroatom;

wherein J is O, S, NR', or CR'R", wherein each of R' and R" is independently hydrogen, halogen, an aliphatic, an aryl or a heteroaryl;

wherein B is hydrogen, an aliphatic, a natural nucleobase, a modified nucleobase or a universal nucleobase;

wherein $U_2$ is absent or O, S, NR', or CR'R", wherein R' and R" are each independently hydrogen, an aliphatic, an aryl, a heteroaryl, a heterocycle or a cycloalkyl;

wherein I is absent or is O, S, NR', or CR'R", wherein R' and R" are each independently hydrogen, an aliphatic, an aryl, a heteroaryl, a heterocycle and a cycloalkyl;

wherein I and $U_3$ can be combined to form CR'—CR" alkyl, CR'—CR" alkenyl, CR'—CR" alkynyl, an aliphatic, an aryl, a heteroaryl, a heterocycle or taken together to form cycloalkyl or heterocyclic ring; and optionally wherein the glutathione-sensitive moiety ($L_1$) comprises a disulfide bridge or a sulfonyl group or wherein the glutathione-sensitive moiety ($L_1$) is represented by Formula II, Formula III, or Formula IV:

Formula II

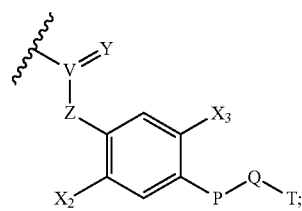

II

Formula III

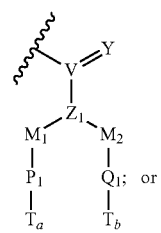

III

; or

Formula IV

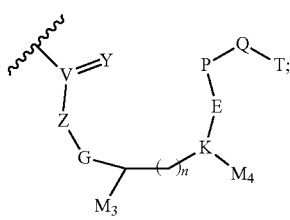

wherein Y is O, S, Se, or NR', wherein R' is hydrogen, halogen, an aliphatic, an aryl, a heteroaryl, or a heterocycle;
wherein Z is O, S, NR', or CR'R", wherein R' and R" are each independently hydrogen, halogen, $CH_3$, an aliphatic, an aryl, a heteroaryl, a heterocycle, or R' and R" are taken together to form a heterocyclic ring;
wherein $Z_1$ is N or CR', wherein R' is hydrogen, halogen, an aliphatic, an aryl, a heteroaryl, a heterocycle;
wherein V is C or SO;
wherein $X_2$ and $X_3$ are independently hydrogen, halogen, nitro, amino, acyl, an aliphatic, $OR_{10}$, $COR_{10}$, $CO_2R_{10}$, or $NQ_1Q_2$; wherein $R_{10}$ is independently hydrogen, an aliphatic, a hydroxyl or alkoxy substituted aliphatic, an arylaliphatic, a hydroxyl or alkoxy substituted aryl, or an alkoxy substituted heterocyclic;
wherein G and E can be each independently absent or $CH_2$, CHR', CR'R", NH, or NR', wherein R' and R" are each independently hydrogen, halogen, an aliphatic, an aryl, a heteroaryl, a heterocycle or R' and R" are taken together to form a heterocyclic ring;
wherein P and Q are taken together to form a disulfide bridge or a sulfonyl group;
wherein $P_1$ and $Q_1$ are taken together to form a disulfide bridge or a sulfonyl group or wherein $P_1$ and $Q_1$ are each independently a disulfide bridge or a sulfonyl group;
wherein when $P_1$ and $Q_1$ form a disulfide bridge, $M_1$, $M_2$, $P_1$, and $Q_1$ can form a 4-9 membered ring, wherein the ring can be aromatic or cycloalkyl, wherein the aromatic or cycloalkyl ring can optionally contain a heteroatom;
wherein T is an aliphatic, an aryl, or T is a ligand optionally connected via a spacer to P or wherein $T_a$ and $T_b$ are each independently absent or $CH_3$, an aliphatic, an aryl, a heteroaryl, a heterocycle or a ligand optionally connected via any spacer to $P_1$ or $Q_1$;
wherein $M_1$ and $M_2$ are each independently an aliphatic, an aromatic, a heteroaryl, or a cycloalkyl;
wherein $M_3$ and $M_4$ are each independently hydrogen, an aliphatic, an aromatic, a heteroaryl, a cycloalkyl or COOR, wherein R is hydrogen, $CH_3$, or an aliphatic, or $M_3$ and $M_4$ can be taken to form a 4-9 membered ring, wherein the ring can be aromatic or cycloalkyl, wherein the aromatic or cycloalkyl ring can optionally contain a heteroatom;
wherein K is C, CH, or an aliphatic; and
wherein n is 0-5.

14. A nucleoside phosphoramidite according to claim 13, wherein:
a) the glutathione-sensitive moiety ($L_1$) is represented by Formula IIIa:

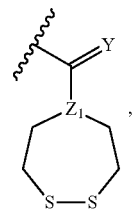

wherein Y is O, S or NH; and wherein $Z_1$ is N or CR', wherein R' is hydrogen, halogen, an aliphatic, an aryl, a heteroaryl, or a heterocycle;
b) the glutathione-sensitive moiety ($L_1$) is represented by Formula IIIb:

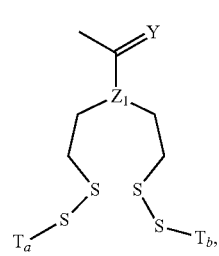

wherein Y is O, S or NH; and wherein $Z_1$ is N or CR', wherein R' is hydrogen, halogen, an aliphatic, an aryl, a heteroaryl, or a heterocycle; and $T_a$ and $T_b$ are each independently absent or $CH_3$, an aliphatic, an aryl, a heteroaryl, a heterocycle or a ligand optionally connected via spacer to a sulfur atom;
c) the glutathione-sensitive moiety ($L_1$) is represented by Formula IIIa(i) or IIIb(i):

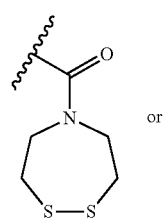

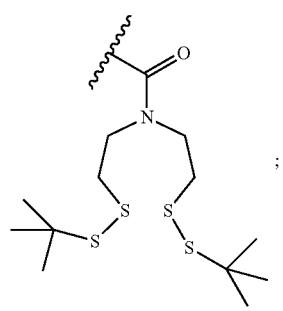

d) the glutathione-sensitive moiety ($L_1$) is represented by Formula IVa:

IVa

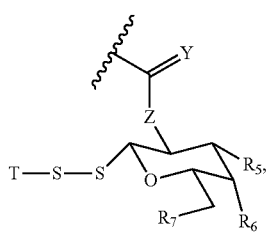

wherein Y is O, S, or NH; wherein Z is O, S or NH; wherein $R_5$, $R_6$, and $R_7$ are each independently OAcyl, NHR', NR', or CR'R", wherein R' and R" are each independently hydrogen, halogen, an aliphatic, an aryl, a heteroaryl, a heterocyclic, or can be taken together to form a heterocyclic ring; and wherein T is a branched or unbranched $C_2$-$C_6$ alkyl or a ligand optionally connected via spacer to a sulfur atom;

e) the glutathione-sensitive moiety ($L_1$) is represented by Formula IVb:

IVb

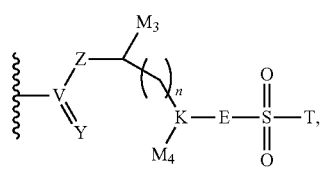

wherein Y is O, S, or NH; Z is O, S or NH; V is C; $M_3$ and $M_4$ are hydrogen; K is CH or an aliphatic; E is NH or NR', wherein R' is an aliphatic; n is 0-5; and T is $C_2$ to $C_6$ alkyl, an aryl, or T is a ligand optionally connected via a spacer to a sulfur atom;

f) the glutathione-sensitive-moiety ($L_1$) is represented by Formula IVc:

IVc

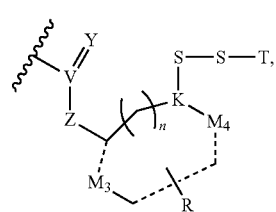

wherein Y is O, S, or NH; Z is O, S, or NR', wherein R' is hydrogen, halogen, $CH_3$, an aliphatic, an aryl, a heteroaryl, or a heterocycle; V is C: $M_3$ and $M_4$ are taken together to form a 5-8 membered ring, wherein the ring is a cycloalkyl, optionally substituted with a heteroatom; K is a branched or unbranched $C_2$ to $C_6$ alkyl; n is 0-5; T is a $C_2$ to $C_6$ alkyl, an aryl, or T is a ligand optionally connected via a spacer; and wherein R is hydrogen, $CH_3$, an aliphatic, an aryl, a heteroaryl, a cycloalkyl, a heterocycle or R is a targeting ligand optionally connected via a spacer;

g) the glutathione-sensitive moiety ($L_1$) is represented by Formula IVd:

IVd

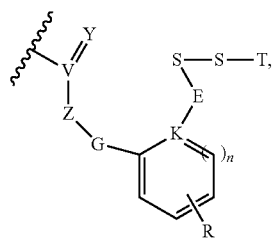

wherein Y is O, S, or NH; Z is O, S, NH, or $NCH_3$; T is a $C_2$ to $C_6$ alkyl, an aryl, or T is a ligand optionally connected via a spacer to a sulfur atom; and R is hydrogen, $CH_3$ or a $C_2$ to $C_6$ alkyl;

h) the glutathione-sensitive moiety ($L_1$) is represented by Formula IVe:

IVe

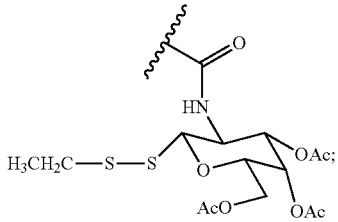

wherein Y is O, S, or NH; Z is O, S, or NR', wherein R' is hydrogen, halogen, $CH_3$, an aliphatic, an aryl, a heteroaryl, or a heterocycle; V is C or SO: G and E can be each independently absent, or $CH_2$, CHR', CR'R", NH, NR', wherein R' and R" are each independently hydrogen, halogen, an aliphatic, an aryl, a heteroaryl, a heterocycle or R' and R" are taken together to form a heterocyclic ring; K is C or CH: n is 0-5; T is a $C_2$ to $C_6$ alkyl, an aryl, or T is a ligand optionally connected via a spacer; and wherein R is hydrogen, $CH_3$, an aliphatic, an aryl, a heteroaryl, a cycloalkyl, a heterocycle or R is a targeting ligand optionally connected via a spacer;

i) the glutathione-sensitive moiety ($L_1$) is represented by Formula IVa(i);

IVa(i)

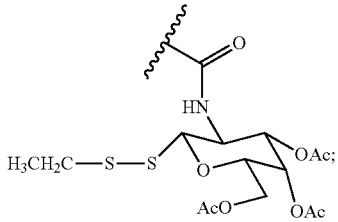

d) the glutathione-sensitive moiety ($L_1$) is represented by Formula IVe(vi), IVe(vii), or IVe(viii);

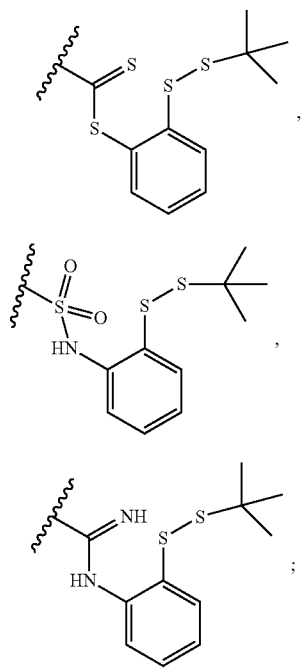

IVe(vi)

IVe(vii)

IVe(viii)

k) J is O; B is a natural nucleobase; $U_2$ is O; I is $CH_2$; WI is a phosphoramidite; $A_1$ is a protecting group, hydrogen, or solid support; and $U_3$ is O;

l) J is O; B is a natural nucleobase; $U_2$ is O; I is $CH_2$; WI is a phosphoramidite; $A_1$ is a protecting group, hydrogen, or solid support; $U_3$ is O; X is O; and $R_1$, $R_2$, $R_3$ and $R_4$ are hydrogen;

m) J is O; B is a natural nucleobase; $U_2$ is O; I is $CH_2$; WI is a protecting group, hydrogen or solid support; $A_1$ is a phosphoramidite, and $U_3$ is O;

n) J is O; B is a natural nucleobase; $U_2$ is O; I is $CH_2$; WI is a protecting group, hydrogen or solid support; $A_1$ is a phosphoramidite, $U_3$ is O; X is O; and $R_1$, $R_2$, $R_3$ and $R_4$ are hydrogen; or o) $U_2$ is O; $W_1$ is a phosphoramidite; and $A_1$ is a is absent, hydrogen, a phosphate group, a phosphate mimic, a phosphoramidate, a protecting group, or a solid support.

15. The nucleoside phosphoramidite according to claim 13, wherein the phosphoramidite has the formula —P(OR$^x$)—N(R$^y$)$_2$, wherein R$^x$ is selected from the group consisting of methyl, 2-cyanoethyl and benzyl, wherein each of R$^y$ is selected from the group consisting of ethyl and isopropyl.

16. A method for preparing a glutathione-sensitive oligonucleotide comprising:
(a) attaching a nucleoside to a solid support via a covalent linkage;
(b) coupling the nucleoside phosphoramidite according to claim 13 to a hydroxyl group on the nucleoside of step (a) to form a phosphorus nucleoside linkage therebetween, wherein any uncoupled nucleoside on the solid support is capped with a capping reagent;
(c) oxidizing said phosphorus nucleoside linkage with an oxidizing reagent; and
(d) repeating steps (b) to (d) iteratively with one or more subsequent nucleoside phosphoramidites according to claim 13 or one or more subsequent nucleoside phosphoramidites that do not contain a glutathione-sensitive moiety, to form the glutathione-sensitive oligonucleotide; and (f) optionally removing said glutathione-sensitive oligonucleotide from said solid support.

17. A glutathione-sensitive nucleoside or nucleotide, wherein the glutathione-sensitive nucleoside or nucleotide is represented by Formula XI:

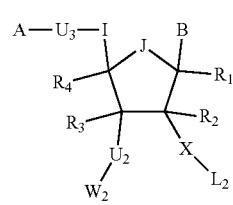

XI wherein $L_2$ is a glutathione-sensitive moiety represented by Formula II, III or IV, or is absent if one of $A_2$ or $W_2$ is the glutathione-sensitive moiety represented by Formula II, III or IV;

wherein if $L_2$ is a glutathione-sensitive moiety, X is O, S, Se, or NR', wherein R' is hydrogen, halogen, an aliphatic, an aryl, a heteroaryl or a heterocycle or if $L_2$ is absent, X is H, OH, SH, $NH_2$, halogen, alkoxy, alkyl, alkenyl, alkynyl, alkylthio, alkylamino or dialkylamino wherein one or more methylenes in the alkyl, alkenyl, and alkynyl may be interrupted with one or more of O, S, S(O), $SO_2$, N(R'), C(O), N(R')C(O)O, OC(O)N(R'), aryl, heteroaryl, heterocyclic or cycloalkyl, O, S, Se or NHR', wherein R' is hydrogen, halogen, an aliphatic, an aryl, a heteroaryl or a heterocycle;

wherein $R_1$, $R_2$, $R_3$ and $R_4$ are each independently hydrogen, halogen, OH, $C_1$-$C_6$ alkyl, $C_1$-$C_6$haloalkyl or wherein two of $R_1$, $R_2$, $R_3$ and $R_4$ are taken together to form a 5-8 membered ring, wherein the ring optionally contains a heteroatom;

wherein J is O, S, NR', or CR'R", wherein each of R' and R" is independently hydrogen, halogen, an aliphatic, aryl or heteroaryl;

wherein B is hydrogen, a natural nucleobase, a modified nucleobase or a universal nucleobase;

wherein $U_2$ is absent or O, S, NR', or CR'R", wherein R' and R" are each independently hydrogen, an aliphatic, an aryl, a heteroaryl, a heterocycle or a cycloalkyl;

wherein $W_2$ is a glutathione-sensitive moiety represented by Formula II, III, or IV;

hydrogen, halogen, OR', SR', NR'R", an aliphatic, an aryl, a heteroaryl, a cycloalkyl, a heterocycle, wherein R' and R" are each independently hydrogen, halogen, an aliphatic, an aryl, a heteroaryl, a heterocycle or are taken together to form a heterocyclic ring;

wherein I is absent or is O, S, NR', or CR'R", wherein R' and R" are each independently hydrogen, an aliphatic, an aryl, a heteroaryl, a heterocycle and a cycloalkyl;

wherein $U_3$ is hydrogen, or O, S, NR' or CR'R", wherein R' and R" are each independently hydrogen, an aliphatic, an aryl, a heteroaryl, a heterocycle and a cycloalkyl;

wherein I and $U_3$ can be combined to form CR'—CR" alkyl, CR'—CR" alkenyl, CR'—CR" alkynyl, an aliphatic, an aryl, a heteroaryl, a heterocycle or taken together to form cycloalkyl or heterocyclic ring; and wherein $A_2$ is absent, hydrogen, a phosphate group, a phosphate mimic, a phosphoramidate, or a glutathione-sensitive moiety represented by Formula II, III, or IV:

Formula II

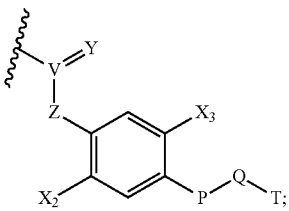

Formula III

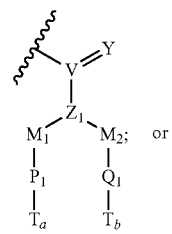

Formula IV

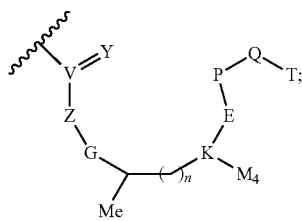

wherein Y is O, S, Se, or NR', wherein R' is hydrogen, halogen, an aliphatic, an aryl, a heteroaryl, or a heterocycle;

wherein Z is O, S, NR', or CR'R", wherein R' and R" are each independently hydrogen, halogen, $CH_3$, an aliphatic, an aryl, a heteroaryl, a heterocycle, or R' and R" are taken together to form a heterocyclic ring;

wherein $Z_1$ is N or CR', wherein R' is hydrogen, halogen, an aliphatic, an aryl, a heteroaryl, a heterocycle;

wherein V is C or SO;

wherein $X_2$ and $X_3$ are independently hydrogen, halogen, nitro, amino, acyl, an aliphatic, $OR_{10}$, $COR_{10}$, $CO_2R_{10}$, or $NQ_1Q_2$; wherein $R_{10}$ is independently hydrogen, an aliphatic, a hydroxyl or alkoxy substituted aliphatic, an arylaliphatic, a hydroxyl or alkoxy substituted aryl, or an alkoxy substituted heterocyclic;

wherein G and E can be each independently absent or $CH_2$, CHR', CR'R", NH, or NR', wherein R' and R" are each independently hydrogen, halogen, an aliphatic, an aryl, a heteroaryl, a heterocycle or R' and R" are taken together to form a heterocyclic ring;

wherein P and Q are taken together to form a disulfide bridge or a sulfonyl group;

wherein $P_1$ and $Q_1$ are taken together to form a disulfide bridge or a sulfonyl group or wherein $P_1$ and $Q_1$ are each independently a disulfide bridge or a sulfonyl group;

wherein when $P_1$ and $Q_1$ form a disulfide bridge, $M_1$, $M_2$, $P_1$, and $Q_1$ can form a 4-9 membered ring, wherein the ring can be aromatic or cycloalkyl, wherein the aromatic or cycloalkyl ring can optionally contain a heteroatom;

wherein T is an aliphatic, an aryl, or T is a ligand optionally connected via a spacer to P or wherein $T_a$ and $T_b$ are each independently absent or $CH_3$, an aliphatic, an aryl, a heteroaryl, a heterocycle or a ligand optionally connected via any spacer to $P_1$ or $Q_1$;

wherein $M_1$ and $M_2$ are each independently an aliphatic, an aromatic, a heteroaryl, or a cycloalkyl;

wherein $M_3$ and $M_4$ are each independently hydrogen, an aliphatic, an aromatic, a heteroaryl, a cycloalkyl or COOR, wherein R is hydrogen, $CH_3$, or an aliphatic, or $M_3$ and $M_4$ can be taken to form a 4-9 membered ring, wherein the ring can be aromatic or cycloalkyl, wherein the aromatic or cycloalkyl ring can optionally contain a heteroatom;

wherein K is C, CH, or an aliphatic; and wherein n is 0-5.

18. The glutathione-sensitive nucleoside or nucleotide according to claim 17, wherein:

a) J is O; X is O; $L_2$ is a glutathione-sensitive moiety represented by Formula II, III, or IV; $W_2$ is hydrogen, halogen, OR', SR', NR'R", an aliphatic, an aryl, a heteroaryl, a cycloalkyl, or a heterocycle, wherein R' and R" are each independently hydrogen, halogen, an aliphatic, an aryl, a heteroaryl, a heterocycle or are taken together to form a heterocyclic ring; and $A_2$ is absent, hydrogen, a phosphate group, a phosphate mimic, or a phosphoramidate;

b) J is O; X is O; $L_2$ is a glutathione-sensitive moiety represented by Formula II, III, or IV; $R_1$, $R_2$, $R_3$, and $R_4$ are hydrogen; $U_2$ is oxygen; $W_2$ is hydrogen; I is $CH_2$; $U_3$ is O; and $A_2$ is hydrogen or a phosphate group;

c) J is O; $R_1$, $R_2$, $R_3$, and $R_4$ are hydrogen; B is a natural nucleobase; $U_2$ is O; X is O; I is $CH_2$, $A_2$ is absent, a hydrogen, a phosphate group, or a phosphate mimic; $U_3$ is O or an internucleotide linking group attaching the glutathione-sensitive nucleoside or nucleotide to a nucleotide or an oligonucleotide; and $W_2$ is hydrogen or an internucleotide linking group attaching the glutathione-sensitive nucleoside or nucleotide to a nucleotide or an oligonucleotide, wherein at least one of $U_3$ or $W_2$ is an internucleotide linking group attaching the glutathione-sensitive nucleoside or nucleotide to an oligonucleotide and provided that if $U_3$ is an internucleotide linking group, $A_2$ is absent; and wherein the glutathione-sensitive oligonucleotide is a double-stranded RNAi inhibitor molecule comprising a sense strand and an antisense strand;

d) J is O; $R_1$, $R_2$, $R_3$, and $R_4$ are hydrogen; B is a natural nucleobase; $U_2$ is O; X is O; I is $CH_2$, $U_3$ is O or an internucleotide linking group attaching the glutathione-sensitive nucleoside or nucleotide to a nucleotide or an oligonucleotide; $A_2$ is hydrogen and $W_2$ is an internucleotide linking group attaching the glutathione-sensitive nucleoside or nucleotide to an oligonucleotide and wherein the glutathione-sensitive nucleoside or nucleotide is located at nucleotide position 1 of an antisense strand of a double-stranded RNAi inhibitor molecule;

e) J is O; $R_1$, $R_2$, $R_3$, and $R_4$ are hydrogen; B is a natural nucleobase; $U_2$ is O; X is O; I is $CH_2$; $A_2$ is absent; $W_2$ is a internucleotide linking group attaching the glutathione-sensitive nucleoside or nucleotide to a first oligonucleotide; and $U_3$ is a internucleotide linking group attaching the glutathione-sensitive nucleoside or nucleotide to a second oligonucleotide; and wherein the glutathione-sensitive nucleoside or nucleotide is located at nucleotide position 14 of an antisense strand of a double-stranded RNAi inhibitor molecule; or f) J is O; $R_1$, $R_2$, $R_3$, and $R_4$ are hydrogen; B is a natural nucleobase; $U_2$ is O; X is O; I is $CH_2$; $A_2$ is absent, a hydrogen, a phosphate group, or a phosphate mimic; $U_3$ is O or an internucleotide linking group attaching the glutathione-sensitive nucleoside or nucleotide to a nucleotide or an oligonucleotide; $W_2$ is hydrogen or an internucleotide linking group attaching the glutathione-sensitive nucleoside or nucleotide to a nucleotide or an oligonucleotide, wherein at least one of $U_3$ or $W_2$ is an internucleotide linking group attaching the glutathione-sensitive nucleoside or nucleotide to an oligonucleotide and provided that if $U_3$ is an internucleotide linking group, $A_2$ is absent; and wherein the glutathione-sensitive oligonucleotide is a double-stranded RNAi inhibitor molecule comprising a sense strand and an antisense strand.

* * * * *

UNITED STATES PATENT AND TRADEMARK OFFICE
CERTIFICATE OF CORRECTION

PATENT NO. : 12,037,358 B2  
APPLICATION NO. : 17/836209  
DATED : July 16, 2024  
INVENTOR(S) : Weimin Wang et al.

Page 1 of 1

It is certified that error appears in the above-identified patent and that said Letters Patent is hereby corrected as shown below:

In the Claims

At Column 96, Line 29, Claim 1: Formula IV is missing

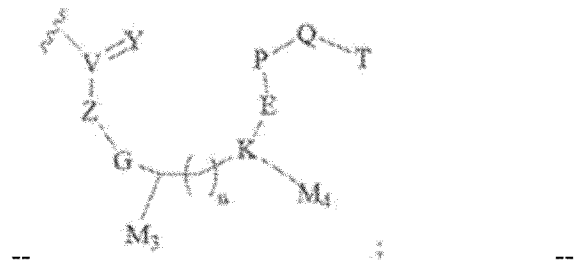

At Column 101, Line 65, Claim 13: in the formula, "W" should be --$W_1$--

At Column 107, Line 30, Claim 14: "WI" should be --$W_1$--

At Column 107, Line 33, Claim 14: "WI" should be --$W_1$--

At Column 107, Line 37, Claim 14: "WI" should be --$W_1$--

At Column 107, Line 40, Claim 14: "WI" should be --$W_1$--

Signed and Sealed this  
Seventeenth Day of September, 2024

Katherine Kelly Vidal  
*Director of the United States Patent and Trademark Office*